(12) United States Patent
Donofrio et al.

(10) Patent No.: US 8,301,263 B2
(45) Date of Patent: Oct. 30, 2012

(54) THERAPY MODULE CROSSTALK MITIGATION

(75) Inventors: William T. Donofrio, Andover, MN (US); Paul G. Krause, Shoreview, MN (US); Gerald P. Arne, Long Lake, MN (US); John E. Burnes, Coon Rapids, MN (US); David J. Peichel, Minneapolis, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 849 days.

(21) Appl. No.: 12/363,180

(22) Filed: Jan. 30, 2009

(65) Prior Publication Data

US 2010/0114189 A1    May 6, 2010

Related U.S. Application Data

(60) Provisional application No. 61/110,066, filed on Oct. 31, 2008.

(51) Int. Cl.
*A61N 1/00* (2006.01)
(52) U.S. Cl. .................. 607/60; 607/2; 607/31; 607/32
(58) Field of Classification Search ................ 607/2, 31, 607/60
See application file for complete search history.

(56) References Cited

U.S. PATENT DOCUMENTS

| | | | |
|---|---|---|---|
| 4,374,382 A | 2/1983 | Markowitz |
| 4,886,064 A | 12/1989 | Strandberg |
| 4,987,897 A | 1/1991 | Funke |
| 5,113,859 A | 5/1992 | Funke |
| 5,117,824 A | 6/1992 | Keimel et al. |
| 5,261,400 A | 11/1993 | Bardy |
| 5,292,338 A | 3/1994 | Bardy |
| 5,545,186 A | 8/1996 | Olson et al. |
| 5,755,736 A | 5/1998 | Gillberg et al. |
| 5,792,212 A | 8/1998 | Weijand |
| 5,899,928 A | 5/1999 | Sholder et al. |
| 6,134,470 A | 10/2000 | Hartlaub |

(Continued)

FOREIGN PATENT DOCUMENTS

WO    2007047681 A2    4/2007

(Continued)

OTHER PUBLICATIONS

International Preliminary Report on Patentability from international application No. PCT/2009/062650, dated May 12, 2011, 7 pp.

(Continued)

*Primary Examiner* — Carl H Layno
*Assistant Examiner* — Paula J Stice
(74) *Attorney, Agent, or Firm* — Michael C. Soldner

(57) ABSTRACT

A first implantable medical device (IMD) implanted within a patient may communicate with a second IMD implanted within the patient by encoding information in an electrical stimulation signal. The delivery of the electrical stimulation signal may provide therapeutic benefits to the patient. The second IMD may sense the electrical stimulation signal, which may be presented as an artifact in a sensed cardiac signal, and process the sensed signal to retrieve the encoded information. The second IMD may modify its operation based on the received therapy information. Crosstalk between the first and second IMDs may be reduced using various techniques described herein. For example, the first IMD may generate the electrical stimulation signal to include a spread spectrum energy distribution or a predetermined signal signature. The second IMD may effectively remove a least some of the signal artifact in a sensed cardiac signal based on the predetermined signal signature.

24 Claims, 20 Drawing Sheets

U.S. PATENT DOCUMENTS

| | | |
|---|---|---|
| 7,387,610 B2 | 6/2008 | Stahmann et al. |
| 7,634,317 B2 | 12/2009 | Ben-David et al. |
| 2001/0001126 A1 | 5/2001 | Cammilli et al. |
| 2005/0149133 A1 | 7/2005 | Libbus et al. |
| 2005/0197680 A1 | 9/2005 | DelMain et al. |
| 2006/0031378 A1 | 2/2006 | Vallapureddy et al. |
| 2006/0095080 A1 | 5/2006 | Libbus et al. |
| 2006/0241699 A1 | 10/2006 | Libbus et al. |
| 2007/0088394 A1 | 4/2007 | Jacobson |
| 2007/0239229 A1 | 10/2007 | Masoud et al. |
| 2007/0260283 A1 | 11/2007 | Li |
| 2008/0015659 A1 | 1/2008 | Zhang et al. |
| 2008/0021507 A1 | 1/2008 | Libbus et al. |
| 2008/0046052 A1 | 2/2008 | Werder et al. |
| 2008/0125826 A1 | 5/2008 | Belalcazar et al. |
| 2008/0147140 A1 | 6/2008 | Ternes et al. |
| 2008/0167696 A1 | 7/2008 | Cates et al. |

FOREIGN PATENT DOCUMENTS

| | | |
|---|---|---|
| WO | 2010013170 A1 | 2/2010 |

OTHER PUBLICATIONS

U.S. Appl. No. 61/110,053, filed Oct. 31, 2008, entitled "Communication Between Implantable Medical Devices", by Krause et al.

U.S. Appl. No. 12/636,215, filed Jan. 30, 2009, entitled "Communication Between Implantable Medical Devices", by Krause et al.

U.S. Appl. No. 61/110,066, filed Oct. 31, 2008, entitled "Therapy Module Crosstalk Mitigation", by Donofrio et al.

International Search Report and Written Opinion for corresponding PCT/US2009/062550, 12 pages, mail date Mar. 29, 2010.

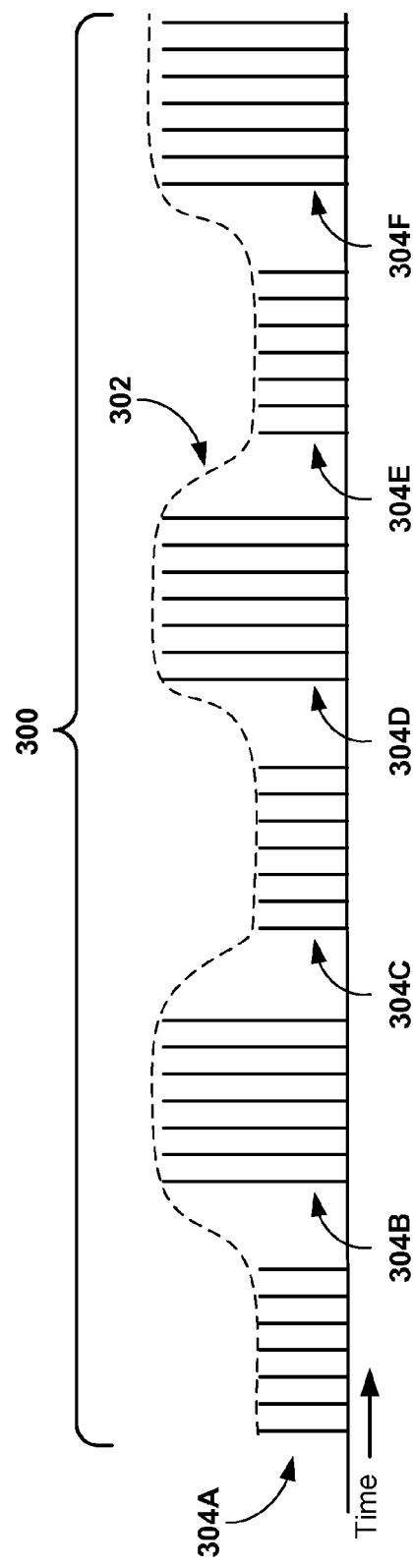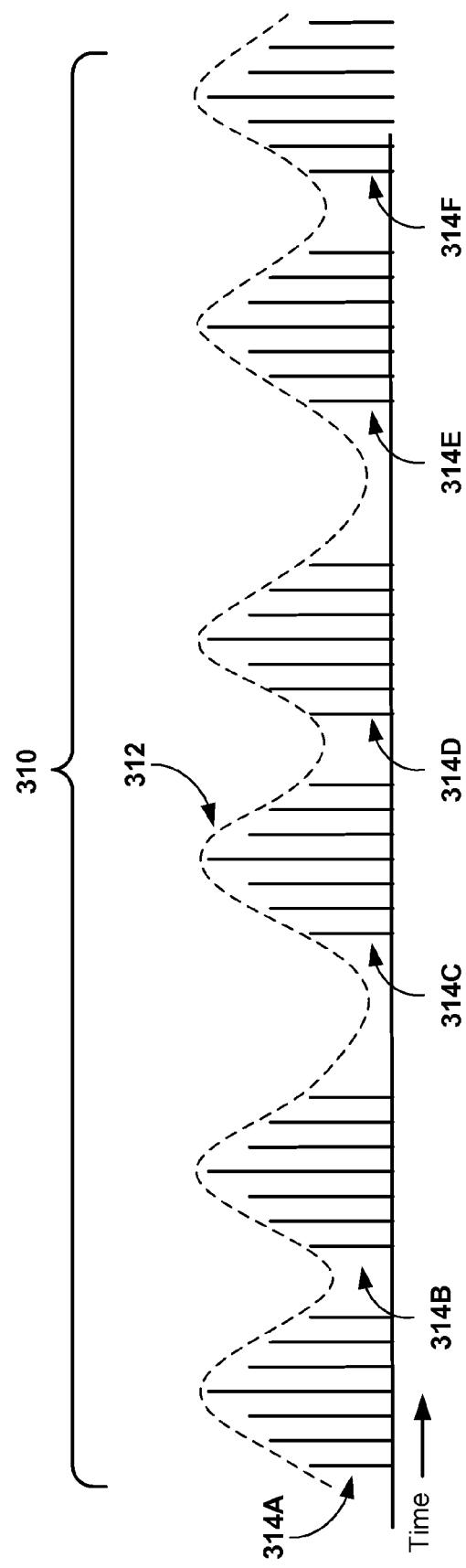

THERAPY MODULE CROSSTALK MITIGATION

This application claims the benefit of U.S. Provisional Application No. 61/110,066, entitled, "THERAPY MODULE CROSSTALK MITIGATION," and filed on Oct. 31, 2008, the entire content of which is incorporated herein by reference.

TECHNICAL FIELD

The disclosure relates to therapy systems and, more particularly, therapy systems including at least two therapy delivery devices.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an IMD housing as an alternative or in addition to electrodes or sensors deployed on one or more leads.

For example, implantable cardiac devices, such as cardiac pacemakers or implantable cardioverter defibrillators, provide therapeutic electrical stimulation to the heart by delivering electrical therapy signals such as pulses or shocks for pacing, cardioversion or defibrillation pulses via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver cardioversion or defibrillation therapy to a patient's heart upon detecting ventricular fibrillation. Some medical device systems that include a neurostimulator in addition to implantable cardiac device have also been proposed.

SUMMARY

In general, the disclosure is directed toward therapy systems that deliver electrical stimulation therapy to a tissue site, such as a nonmyocardial tissue site (e.g., tissue proximate a nerve) or a nonvascular cardiac tissue site (e.g., a cardiac fat pad), within a patient and cardiac rhythm management therapy to a heart of a patient. In some examples, the therapy system may include a first implantable medical device (IMD) that delivers electrical stimulation to the tissue site within a patient, such as a tissue site proximate a nerve (e.g., a vagus nerve or a spinal cord) or another tissue site, and a second IMD that delivers cardiac rhythm management therapy, such as at least one of pacing, cardioversion or defibrillation therapy to a heart of the patient. The ICD may deliver any combination of pacing, cardioversion, and defibrillation pulses. The first and second implantable medical devices are not physically connected each other. The first IMD may be referred to as an implantable neurostimulator (INS) or an electrical stimulator, and the second IMD may be referred to as an implantable cardiac device (ICD). In other examples, the therapy system may include an implantable medical device that includes a first therapy module that delivers stimulation therapy to a nonmyocardial tissue site within a patient and a second therapy module that delivers at least one of pacing, cardioversion or defibrillation therapy to the heart of the patient, where the first and second therapy modules are disposed in a common housing.

Techniques that may be implemented to communicate information between the first and second IMDs are described herein. In some examples, the first and second IMDs may communicate with each other by encoding therapy information in a stimulation signal, which may be transmitted to the other device through tissue of the patient. The information may be encoded in a stimulation signal by, for example, varying one or more signal parameters, e.g., a slew rate, the frequency, phase, duty cycle, and, in the case of stimulation pulses, the pulse rate and pulse width. The encoded information may provide information regarding the therapy being delivered by the INS, such as the duration of the therapy and/or the type of therapy. The encoded information may also include information regarding the operation of the INS, such as information that indicates when the INS is being recharged. In some examples, the receiving device may modify its operation based on the received therapy information.

In addition, techniques for minimizing interference between the first and second IMDs or between the different therapy modules of a common medical device are described herein. In some examples, the first IMD may randomly or pseudo-randomly vary one or more signal parameters to generate a stimulation signal that has a spread spectrum energy distribution. Consequently, the signal artifact present on an electrical signal sensed by the second IMD may appear as wideband noise in the sensed signal. The second IMD may employ signal processing techniques well known in the art to suppress the wideband noise. These examples facilitate the removal of a signal artifact from the signal sensed by the ICD and, thus, may provide improved performance for therapy systems that include an INS and ICD.

In one aspect, the disclosure is directed to a method comprising generating an electrical stimulation signal with a first IMD implanted within a patient, encoding information in the electrical stimulation signal with the first IMD, and delivering the electrical stimulation signal to tissue within the patient, where delivering the electrical stimulation signal comprises transmitting the information to a second IMD implanted within the patient.

In another aspect, the disclosure is directed to a method comprising sensing an electrical stimulation signal with an electrode electrically connected to a first IMD implanted within a patient, where the electrical stimulation signal is generated by a second IMD implanted within the patient and encoded with information by the second IMD, and processing the electrical stimulation signal with the first IMD to retrieve the information.

In another aspect, the disclosure is directed to a method comprising generating an electrical stimulation signal with a first IMD, encoding information in the electrical stimulation signal with the first IMD, sensing the electrical stimulation signal with an electrode electrically connected to a second IMD, and processing the sensed electrical stimulation signal with the second IMD to retrieve the information.

In another aspect, the disclosure is directed to a system comprising a stimulation generator that generates an electrical stimulation signal, and a processor that controls the stimulation generator to encode information in the electrical stimulation signal and deliver the electrical stimulation signal to a patient.

In another aspect, the disclosure is directed to a system comprising an electrode electrically connected to a first IMD implanted within a patient, a sensing module that senses an electrical stimulation signal with the electrode, where the electrical stimulation signal is generated by a second IMD implanted within the patient and encoded with information, and a processor that processes the electrical stimulation signal to retrieve the information.

In another aspect, the disclosure is directed to a system comprising a first IMD that generates an electrical stimulation signal and encodes information in the electrical signal, and a second IMD that senses the electrical stimulation signal and processes the electrical stimulation signal to retrieve the information. The first and second IMD are implanted within a patient.

In another aspect, the disclosure is directed to a system comprising means for generating an electrical stimulation signal with a first IMD implanted within a patient, means for encoding information in the electrical stimulation signal with the first IMD, and means for delivering the electrical stimulation signal to tissue within a patient, where delivering the electrical stimulation signal comprises transmitting the information to a second IMD implanted within the patient.

In another aspect, the disclosure is directed to a system comprising means for sensing an electrical stimulation signal with an electrode electrically connected to a first IMD implanted within a patient, where the electrical stimulation signal is generated by a second IMD implanted within the patient and encoded with information by the second IMD, and means for processing the electrical stimulation signal with the first IMD to retrieve the information.

In another aspect, the disclosure is directed to a system comprising means for generating an electrical stimulation signal with a first IMD, means for encoding information in the electrical stimulation signal, means for sensing the electrical stimulation signal with an electrode electrically connected to a second IMD, and means for processing the sensed electrical stimulation signal to retrieve the information.

In another aspect, the disclosure is directed to a method comprising generating an electrical stimulation signal that has a predetermined signature with a first therapy module that delivers electrical stimulation therapy to a patient, where the predetermined signature is characterized by at least one of a duty cycle or a signal envelope of the electrical stimulation signal, delivering the electrical stimulation signal to tissue of the patient via a first set of electrodes electrically connected to the first therapy module, sensing electrical activity within the patient with a second set of electrodes electrically connected to a second therapy module, where the electrical activity includes a physiological signal of the patient and a signal artifact from the delivery of the electrical stimulation signal by the first therapy module, generating a sensed electrical signal based on the sensed electrical activity, and processing the sensed electrical signal to remove at least part of the signal artifact based on the predetermined signature.

In another aspect, the disclosure is directed to a method comprising sensing electrical activity within a patient with a second therapy module, where the electrical activity includes a physiological signal of the patient and a signal artifact from a delivery of an electrical stimulation signal to the patient by an IMD, the electrical stimulation signal comprising a predetermined signature that is characterized by at least one of a duty cycle or a signal envelope of the electrical stimulation signal, generating a sensed electrical signal based on the sensed electrical activity, and processing the sensed electrical signal to remove at least part of the signal artifact based on the predetermined signature of the electrical stimulation signal.

In another aspect, the disclosure is directed to a system comprising a first set of electrodes, a second set of electrodes, a first therapy module that generates and delivers an electrical stimulation signal having a predetermined signature to tissue of a patient via the first set of electrodes, where the predetermined signature is characterized by at least one of a duty cycle or a signal envelope of the electrical stimulation signal, a second therapy module that senses electrical activity within the patient via the second set of electrodes, where the electrical activity includes a physiological signal and a signal artifact from the delivery of the electrical stimulation signal by the first therapy module, and where the second therapy module generates a sensed electrical signal based on the electrical activity, and a processor that processes the sensed electrical signal to remove at least part of the signal artifact based on the predetermined signature.

In another aspect, the disclosure is directed to a system comprising means for generating an electrical stimulation signal that has a predetermined signature, where the predetermined signature is characterized by at least one of a duty cycle or a signal envelope of the electrical stimulation signal, means for delivering the electrical stimulation signal to tissue of the patient via a first set of electrodes electrically connected to the first therapy module, means for sensing electrical activity within the patient with a second set of electrodes electrically connected to a second therapy module, where the electrical activity includes a physiological signal of the patient and a signal artifact from the delivery of the electrical stimulation signal by the first therapy module, means for generating a sensed electrical signal based on the sensed electrical activity, and means for processing the sensed electrical signal to remove at least part of the signal artifact on the predetermined signature.

In another aspect, the disclosure is directed to a method comprising at least one of randomly or pseudo-randomly varying a value of at least one signal parameter to generate an electrical stimulation signal comprising a spread spectrum energy distribution, and delivering the electrical stimulation signal to tissue of a patient.

In another aspect, the disclosure is directed to a method comprising sensing electrical activity within a patient via a set of electrodes electrically connected to a first therapy module, where the electrical activity includes a physiological signal of the patient and a signal artifact from delivery of an electrical stimulation signal by a second therapy module, and where the electrical stimulation signal comprises a spread spectrum energy distribution, generating a sensed electrical signal based on the sensed electrical activity, and processing the sensed electrical signal to monitor cardiac activity of the patient.

In another aspect, the disclosure is directed to a system comprising a first set of electrodes, a second set of electrodes, a stimulation generator that generates and delivers an electrical stimulation signal comprising a spread spectrum energy distribution to a patient via the first set of electrodes, a sensing module that senses electrical activity of the patient via the second set of electrodes and generates an electrical signal based on the electrical activity, where the electrical activity includes a physiological signal of the patient and a signal artifact from delivery of the electrical stimulation signal by the stimulation generator, and a processor that processes the sensed electrical signal to monitor cardiac activity of the patient In another aspect, the disclosure is directed to a system comprising means for generating an electrical stimulation signal, means for delivering the electrical stimulation signal to tissue of a patient, means for sensing electrical activity within the patient, where the electrical activity includes a physiological signal of the patient and a signal artifact from the delivery of the electrical stimulation signal, means for generating a sensed electrical signal based on the sensed electrical activity, and means for processing the sensed electrical signal to monitor cardiac activity of the patient.

In another aspect, the disclosure is directed to a computer-readable medium containing instructions. The instructions cause a programmable processor to perform any part of the techniques described herein.

The details of one or more examples of the disclosure are set forth in the accompanying drawings and the description below. Other features, objects, and advantages of the disclosure will be apparent from the description and drawings, and claims provided below.

BRIEF DESCRIPTION OF DRAWINGS

FIGS. 12A, 12B, 13A, and 13B illustrate example stimulation waveforms that facilitate removal of the resulting signal artifact at the ICD.

DETAILED DESCRIPTION

The disclosure describes techniques that may be employed by a first implantable medical device (IMD) to communicate with a second IMD, where the first and second IMDs are implanted within a common patient. For example, the first IMD may encode information in a stimulation signal delivered to a patient, and the second IMD may sense the stimulation signal and decode the signal to receive the information. The second IMD may also implement the communication techniques described herein to communicate with the first IMD.

Figure 1:
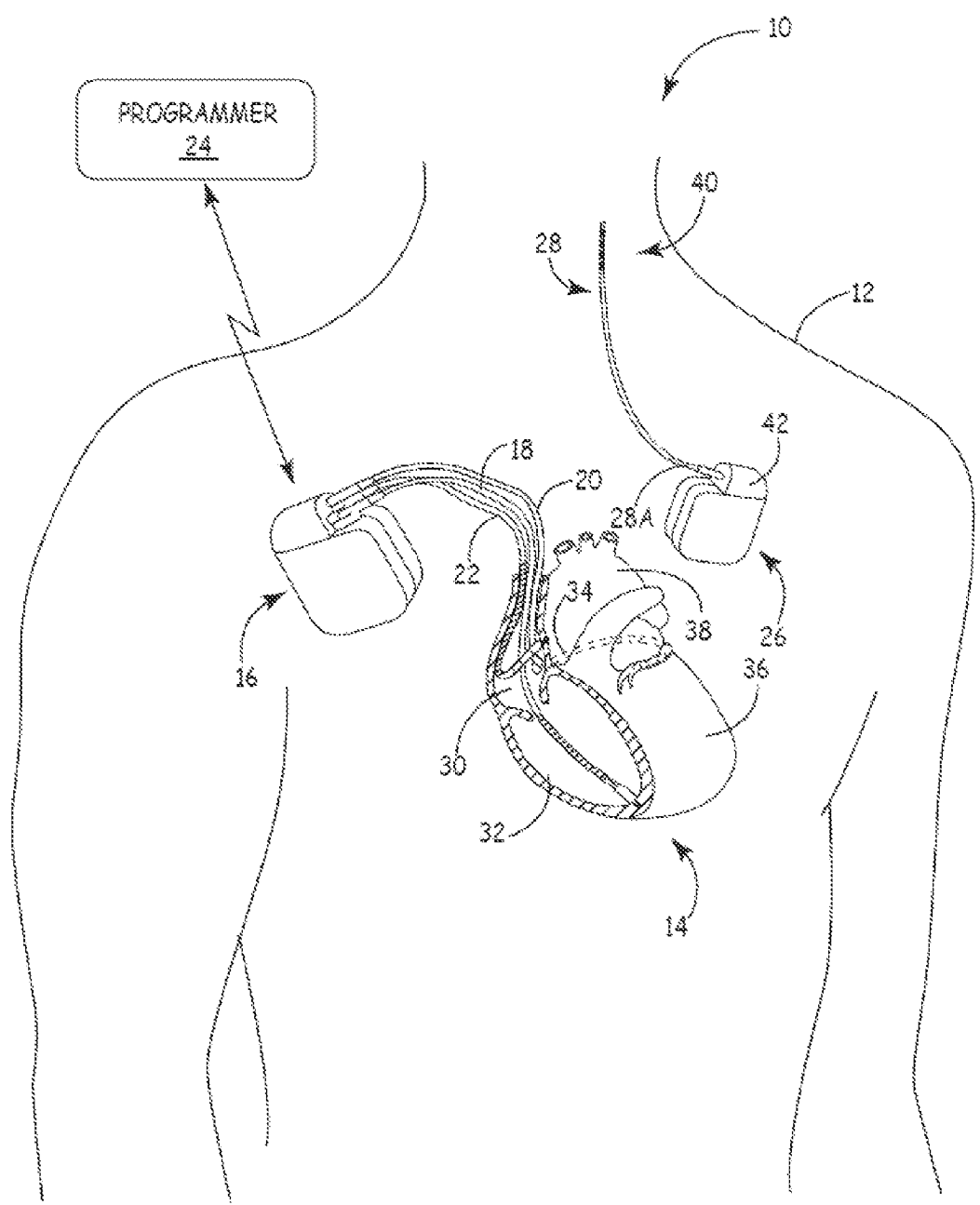
FIG. 1 is a conceptual diagram illustrating an example therapy system that includes an implantable neurostimulator (INS) and an implantable cardiac device (ICD) in accordance with various examples described in this disclosure.

As described with respect to FIG. 1, the first IMD may comprise an implantable electrical stimulator that provides electrical stimulation therapy to a nonmyocardial tissue site (e.g., a tissue proximate a nerve of a patient or a tissue site outside of vasculature and not proximate a nerve), or a nonvascular cardiac tissue site (e.g., a cardiac fat pad). The second IMD may comprise a cardiac rhythm management device (i.e., an implantable cardiac device (ICD)) that senses electrical cardiac signals of a heart of the patient and, in some examples, provides at least one of pacing, cardioversion or defibrillation therapy to the heart of the patient.

Also described herein are techniques for reducing electrical crosstalk between first and second IMDs implanted within a patient, and, in some cases, between first and second therapy modules of a common medical device. The electrical crosstalk may be at least partially attributable to electrical stimulation signals generated and delivered by one IMD and sensed by the other IMD. The electrical crosstalk may be presented as an artifact present in an electrical signal sensed by a first IMD, where the artifact may be at least partially attributable to the stimulation signals generated by the second IMD. In this way, the artifact may be referred to as a "stimulation artifact" or a "signal artifact." It may be desirable to minimize electrical crosstalk in order to minimize the possibility that interference from the electrical stimulation signals delivered by an electrical stimulator does not interfere with the proper detection of cardiac signals by an ICD. For example, if an ICD senses electrical stimulation signals generated and delivered by an electrical stimulator, such as an implantable neurostimulator (INS), and mischaracterizes the electrical stimulation signals as cardiac signals, the ICD may inappropriately detect an arrhythmia. This may result in the inappropriate delivery of pacing, cardioversion, and/or defibrillation therapy to the patient.

FIG. 1 is a conceptual diagram illustrating an example therapy system 10 that provides therapy to patient 12. Therapy system 10 includes ICD 16, which is coupled to leads 18, 20, and 22, and programmer 24. ICD 16 may be, for example, an IMD that sense electrical cardiac activity of heart 14 via electrodes coupled to one or more of leads 18, 20, and 22. In some examples, ICD 16 may also comprise at least one of an implantable pacemaker, cardioverter, and/or defibrillator that delivers cardiac rhythm management therapy to heart 14 via electrodes coupled to one or more of leads 18, 20, and 22. In some examples, ICD 16 may deliver pacing pulses, but not cardioversion or defibrillation pulses, while in other examples, ICD 16 may deliver cardioversion or defibrillation pulses, but not pacing pulses. In addition, in further examples, ICD 16 may deliver pacing, cardioversion, and defibrillation therapy to heart 14. In various examples, ICD 16 may deliver pacing that includes one or both of anti-tachycardia pacing (ATP) and cardiac resynchronization therapy (CRT).

Therapy system 10 further comprises implantable electrical stimulator 26, which is coupled to lead 28. Electrical stimulator 26 may also be referred to as an INS 26. INS 26 may be any suitable implantable medical device (IMD) that includes a signal generator that generates electrical stimulation signals that may be delivered to a tissue site of patient 12, e.g., tissue proximate a vagus nerve, a spinal cord or heart 14 of patient 12.

In some examples, the tissue site may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

In some examples, delivery of electrical stimulation to a tissue site proximate a nerve or a nonmyocardial tissue site that may not be proximate a nerve may help modulate an autonomic nervous system of patient 12. In some examples, INS 26 delivers electrical stimulation therapy to a nerve of patient 12 via a lead implanted within vasculature (e.g., a blood vessel) of patient 12. In addition, in some examples, INS 26 delivers electrical stimulation that is delivered to peripheral nerves that innervate heart 14, or fat pads on heart 14 that may contain nerve bundles. The fat pads may be referred to as a nonvascular cardiac tissue site.

In the example shown in FIG. 1, electrodes of lead 28 are positioned outside the vasculature of patient 12 and positioned to deliver electrical stimulation to a vagus nerve (not shown) of patient 12. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature.

In the example shown in FIG. 1, the components of ICD 16 and INS 26 are enclosed in separate housings, such that ICD 16 and INS 26 are physically separate devices. In other examples, as described with respect to FIG. 19, the functionality of ICD 16 and INS 26 may be performed by an implantable medical device (IMD) that includes both a cardiac therapy module that generates and delivers at least one of a pacing, cardioversion or defibrillation signal to patient 12 and an electrical stimulation therapy module that generates and delivers electrical stimulation to a target tissue site within patient 12.

Leads 18, 20, 22 extend into the heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As described in further detail with reference to FIG. 3, in other examples, ICD 16 may deliver stimulation therapy to heart 14 by delivering stimulation to an extravascular tissue site in addition to or instead of delivering stimulation via electrodes of intravascular leads 18, 20, 22.

ICD 16 may sense electrical signals attendant to the depolarization and repolarization of heart 14 via electrodes (not shown in FIG. 1) coupled to at least one of the leads 18, 20, 22. In some examples, ICD 16 provides pacing pulses to heart 14 based on the electrical signals sensed within heart 14. These electrical signals sensed within heart 14 may also be referred to as cardiac signals or electrical cardiac signals. The configurations of electrodes used by ICD 16 for sensing and pacing may be unipolar or bipolar. ICD 16 may also provide defibrillation therapy and/or cardioversion therapy via electrodes located on at least one of the leads 18, 20, 22. ICD 16 may detect arrhythmia of heart 14, such as fibrillation of ventricles 32 and 36, and deliver defibrillation therapy to heart 14 in the form of electrical pulses. In some examples, ICD 16 may be programmed to deliver a progression of therapies, e.g., pulses with increasing energy levels, until a fibrillation of heart 14 is stopped. ICD 16 detects fibrillation employing one or more fibrillation detection techniques known in the art.

In the example of FIG. 1, INS 26 has been implanted in patient 12 proximate to a target stimulation site 40, such as a tissue site proximate a vagus nerve. For example, INS 26 may be subcutaneously or submuscularly implanted in the body of a patient 12 (e.g., in a chest cavity, lower back, lower abdomen, or buttocks of patient 12). INS 26 provides a programmable stimulation signal (e.g., in the form of electrical pulses or a continuous signal) that is delivered to target stimulation site 40 by implantable medical lead 28, and more particularly, via one or more stimulation electrodes carried by lead 28. In some examples, lead 28 may also carry one or more sense electrodes to permit INS 26 to sense electrical signals from target stimulation site 40. Stimulation and sense electrodes carried by lead 28 are generally referred to as electrodes 46 throughout this disclosure. Furthermore, in some examples, INS 26 may be coupled to two or more leads, e.g., for bilateral or multi-lateral stimulation.

In the example illustrated in FIG. 1, lead 28 includes four electrodes 46. In other examples, lead 28 may carry any suitable number of electrodes, such as fewer than four electrodes or greater than four electrodes (e.g., eight or sixteen electrodes). Electrodes 46 may comprise ring electrodes. In other examples, electrodes 46 may be arranged in a complex electrode array that includes multiple non-contiguous electrodes at different angular positions about the outer circumference of lead 28, as well as different levels of electrodes spaced along a longitudinal axis of lead 28. The configuration, type, and number of electrodes 46 illustrated in FIG. 1 are merely exemplary. In other examples, INS 26 may be coupled to any suitable number of leads with any suitable number and configuration of electrodes. Moreover, lead 28 may comprise a shape other than a cylindrical shape. As an example, lead 28 may comprise a paddle-shaped portion that carries electrodes 46.

Proximal end 28A of lead 28 may be both electrically and mechanically coupled to connector 42 of INS 26 either directly or indirectly (e.g., via a lead extension). In particular, conductors disposed in the lead body may electrically connect stimulation electrodes (and sense electrodes, if present) of lead 28 to INS 26.

Delivery of electrical stimulation by INS 26 to one or more target tissues sites proximate to a nerve, nerve site, cardiac fat pad, or an extravascular target tissue site that is not proximate a nerve may provide cardioprotective benefits to patient 12. An extravascular tissue site may be outside of heart 14 and outside of arteries, veins, or other vasculature of patient 12. For example, delivery of electrical stimulation to a tissue site proximate a nerve of patient 12 may help treat heart failure. In addition, delivery of electrical stimulation to a tissue site proximate a nerve of patient 12 to modulate an autonomic nervous system of patient 12 may help reduce or eliminate cardiovascular conditions such as bradycardia, tachycardia, unhealthy cardiac contractions, ischemia, inefficient heart pumping, inefficient collateral circulation of heart 14 or cardiac muscle trauma. Delivery of electrical stimulation by INS 26 may augment antitachycardia pacing by ICD 16 or provide back-up therapy to ICD 16. For example, if ICD 16 is unavailable to provide therapy to patient 12, e.g., due to a low power level, INS 26 may deliver therapy to patient 12 to help terminate or prevent a cardiac event (e.g., tachycardia).

The electrical stimulation signals generated and delivered by INS 26 may be referred to as neurostimulation signals. However, in some examples, INS 26 may deliver electrical stimulation to a target tissue site 40 that is not proximate to a nerve. For example, in some examples, INS 26 may deliver electrical stimulation to a peripheral nerve field site, whereby electrodes 46 are implanted in a region where patient 12 experiences pain, but may not be proximate a nerve. The pain may be related to stimulation delivered by ICD 16 or a patient condition, such as angina or chronic back pain. As other examples, INS 26 may deliver electrical stimulation to a muscle, muscle group, organ, or other sites that may not be proximate a nerve. Thus, while "neurostimulation" signals are referred to herein, the disclosure is also applicable to examples in which INS 26 delivers electrical stimulation to other tissue sites, which may be intravascular or extravascular.

In the example shown in FIG. 1, lead 28 connected to INS 26 is positioned to provide electrical stimulation therapy of a parasympathetic nerve, such as a vagus nerve, of patient 12. Stimulation of a parasympathetic nerve of patient 12 may help slow intrinsic rhythms of heart 14, which may facilitate antitachyarrhythmia therapy (e.g., antitachycardia pacing, cardioversion or defibrillation) delivered by ICD 16. In this way, neurostimulation by INS 26 may help control a heart rate of patient 12.

In some examples, depending upon the neurostimulation target, the delivery of electrical stimulation by INS 26 may also mitigate perceptible discomfort generated from the delivery of pacing pulses or cardioversion/defibrillation shocks by ICD 16. For example, if INS 26 delivers electrical stimulation to spinal cord 44 (FIG. 2) of patient 12, the neurostimulation may produce paresthesia, which may help reduce the discomfort felt by patient 12 from the delivery of stimulation by ICD 16.

In other examples, electrodes 46 of lead 28 may be positioned to deliver electrical stimulation to any other suitable nerve, organ, muscle or muscle group in patient 12, which may be selected based on, for example, a therapy program selected for a particular patient. In some examples, INS 26 may deliver electrical stimulation to other parasympathetic nerves, baroreceptors, the carotid sinus or a cardiac branch of the vagal trunk of patient 12 in order to facilitate the delivery of therapy by ICD 16. Another example configuration of therapy system 10 is described below with respect to FIG. 2, in which INS 26 is positioned to deliver electrical stimulation to the spinal cord of patient 12.

INS 26 may deliver electrical stimulation to patient 12 substantially continuously or periodically. In some examples, INS 26 may deliver electrical stimulation to patient 12 based on the timing of electrical stimulation by ICD 16, such as prior to the delivery of electrical stimulation (e.g., antitachycardia pacing) by ICD 16, during the delivery of electrical stimulation by ICD 16, subsequent to the delivery of electrical stimulation by ICD 16 or any combination of the aforementioned times.

ICD 16 and INS 26 may communicate with each other in order for INS 26 to time the delivery of electrical stimulation based on the delivery of stimulation pulses by ICD 16, where the stimulation pulses may be pacing pulses or cardioversion/defibrillation pulses. ICD 16 and INS 26 may communicate directly or indirectly (e.g., via an intermediate device, such as programmer 24) using any suitable communication technique. Examples communication techniques that may be implemented to facilitate communication between ICD 16 and INS 26 are described below with reference to FIGS. 7-9 and 15-18.

ICD 16 may sense electrical noise and interpret the electrical noise as electrical cardiac signals (e.g., an electrocardiogram (ECG) or electrogram (EGM) signal). This may cause ICD 16 to oversense the heart rhythms, and, in some cases, erroneously detect an arrhythmia based on the electrical noise. For example, a processor of ICD 16 may identify electrical noise as a heart rhythm, and detect the presence of a tachyarrhythmia episode or event (e.g., a heart cycle measured between successive R-waves that has a duration less than a threshold value) based on the electrical noise. A tachyarrhythmia episode may include more than one tachyarrhythmia event. Depending on the source of the electrical noise, the electrical noise may present itself as a relatively fast rhythm, which the processor may interpret as one or more tachyarrhythmia events, which may then be used to detect a tachyarrhythmia episode. ICD 16 may detect the presence of a tachyarrhythmia episode by determining whether a certain number of intervals of a particular number of total intervals have a certain duration, e.g., whether a certain number of intervals are considered tachyarrhythmia events.

Oversensing of the heart rhythms may result in inappropriate withholding or delivery of electrical stimulation to heart 14. For example, oversensing may cause ICD 16 to detect a tachycardia or fibrillation episode when heart 14 is in a normal sinus rhythm, which may result in the inappropriate delivery of a high voltage defibrillation shock.

Undersensing of the heart rhythms may also result in inappropriate delivery of pacing therapy to heart 14. ICD 16 may undersense the heart rhythms when the electrical noise masks the actual electrical cardiac signals. For example, the electrical noise may cause a sense amplifier of ICD 16 that is used to sense electrical cardiac signals to be less sensitive. In this case, the electrical noise may have a sufficiently large amplitude, e.g., larger than the amplitude of the electrical cardiac signal, that ICD 16 calibrates its detection algorithm to detect signals having an amplitude larger than that of the electrical cardiac signal. As a result, ICD 16 may undersense the electrical cardiac signal and determine that the R-R intervals present a relatively slow rhythm. Consequently, undersensing may result in inappropriate delivery of electrical stimulation to heart 14.

In another example, ICD 16 may undersense the electrical cardiac signals when heart 14 is not, in fact, in a normal sinus rhythm, and the electrical noise interferes with the electrical cardiac signals in a way that causes ICD 16 to interpret the combined signal of electrical noise and irregular electrical cardiac signal as a normal sinus rhythm. In this case, undersensing may result in inappropriate withholding of electrical stimulation to heart 14.

Electrical noise that ICD 16 characterizes as heart rhythms may be attributable to different sources. The stimulation signal generated by INS 26 and delivered to the tissue site 40 of patient 12 may be coupled to ICD 16 through tissue of patient 12. Thus, in some cases, ICD 16 may sense the electrical stimulation signals (or "neurostimulation signals") generated by and delivered to target tissue site 40 by INS 26. As previously described, ICD 16 senses electrical activity of patient 12 via the electrodes carried by leads 18, 20, and 22. The electrical activity includes an electrical cardiac signal that is produced by the electrical activity of heart 14 and an artifact resulting from the stimulation signal output by INS 26. The artifact may be referred to as "electrical noise" or "interference," and the presence of electrical noise between INS 26 and ICD 16 may be referred to as "crosstalk."

As previously indicated, ICD 16 may control the delivery of electrical stimulation to heart 14 based on electrical cardiac signals (e.g., EGM signals) sensed within heart 14. A sensing integrity issue may arise when ICD 16 senses the electrical stimulation signals generated by INS 26 and mischaracterizes the stimulation signals as cardiac signals. For example, if ICD 16 detects an arrhythmia of heart 14 based on electrical signals generated by INS 26 rather than true electrical cardiac signals, ICD 16 may unnecessarily deliver electrical stimulation (e.g., pacing pulses or defibrillation/cardioversion shocks) to heart 14. As another example, if the electrical noise causes ICD 16 to be less sensitive, ICD 16 may unnecessarily deliver electrical stimulation to heart 14, e.g., when ICD 16 detects a heart rhythm slower than normal.

Therapy system 10 may implement various techniques described herein to reduce the amount of crosstalk between INS 26 and ICD 16. In some examples, one or more sensing parameters of ICD 16 may be modified in response to receiving input that indicates INS 26 is actively delivering electrical stimulation signals to patient 12. For example, ICD 16 may implement a different filter to filter out the electrical stimulation signals delivered by INS 26 from the electrical signals sensed by ICD 16. Filtering out the electrical stimulation signals from INS 26 based on the known characteristics of the electrical stimulation signals may help minimize a possibility that ICD 16 senses the electrical stimulation signals and mischaracterizes them as cardiac signals.

Filtering may be applied in response to receiving information from INS 26 that indicates INS 26 is delivering therapy may be useful because filtering the sensed electrical signals may affect normal cardiac sensing or EGM processing of ICD 16. That is, filtering a sensed signal may inadvertently result in filtering of the cardiac signal component, such that the cardiac sensing or EGM processing is less effective. Thus, selectively applying the filter when the noise from delivery of stimulation by INS 26 is known to be occurring.

INS 26 and ICD 16 are configured to communicate with each other. Accordingly, ICD 16 may receive input from INS 26 that indicates INS 26 is actively delivering electrical stimulation signals to patient 12. INS 26 may transmit information to ICD 16 indicating INS 26 is delivering therapy, and one or more therapy parameters, such as the duration of therapy or one or more electrical stimulation parameter values with which INS 26 generates the electrical stimulation signals. INS 26 may also transmit information to ICD 16 indicating INS 26 is being recharged because recharging INS 26 may also introduce electrical noise that may be mischaracterized by ICD 16. In some examples, as described in further detail below with reference to FIG. 15, INS 26 may transmit the information by encoding the information in a stimulation signal that is delivered to tissue site 40 of patient 12. Example stimulation waveforms that may be used for transmitting information to ICD 16 are shown in FIGS. 10A-10D and described below.

INS 26 may encode the therapy information by varying the value of one or more stimulation parameters, such as the slew rate, frequency (e.g., pulse rate), signal duration (e.g., pulse width), phase (e.g., positive and negative voltages), or duty cycle in a known manner, such that ICD 16 may sense the stimulation signals and extract information therefrom based on the known stimulation parameter values. In some examples, INS 26 varies the value of the one or more stimulation parameters within a predetermined range of values determined to provide efficacious therapy to patient 12.

In some examples, INS 26 may encode information in a stimulation signal by varying signal parameters on a burst-by-burst basis. For example, INS 26 may generate the stimulation signal as a series of bursts of pulses or pulse trains and vary one or more signal parameters for each the bursts of pulses. In some examples, each pulse in particular burst of pulses may be generated using the same stimulation parameter values, but the pulses of subsequent bursts may be generated using different stimulation parameter values. Using this technique, INS 26 may encode information in the stimulation signal by associating particular burst shapes with information, where a burst shape may be defined by the stimulation parameter values (or "signal parameter values") used to generate the pulses. For example, different burst shapes may be associated with specific instructions for ICD 16 or with different alphanumeric indicators, such as letters or numbers, and a plurality of burst shapes (symbols) may be arranged to form words or other indicators that are assigned a unique meaning or, more specifically, unique information relating to the stimulation therapy delivered by INS 26.

In some examples, the alphanumeric indicator encoded in the stimulation signal from INS 26 may be associated with an instruction in the memory of ICD 16. Thus, upon extracting the alphanumeric indicator from the sensed electrical stimulation signal from INS 26, ICD 16 may reference a memory to determine what information was encoded in the stimulation signal. For example, ICD 16 may reference a memory to determine an operating modification associated with the alphanumeric indicator. As described in further detail below, the operating modification may include a modification to a sensing parameter of ICD 16, such as a type of filter used to sense cardiac signals.

In another example, INS 26 may encode information in the stimulation signal by generating an electrical stimulation signal having one or more burst shapes that are associated with information, such as one or more alphanumeric indicators. A particular arrangement of multiple bursts of pulses may be associated with one or more alphanumeric indicators or with a specific instruction for ICD 16. This may be referred to as burst pattern encoding because information is encoded using different "patterns" of burst shapes, where a burst pattern includes more than one burst of pulses.

As another example, INS 26 may encode information in the stimulation signal by varying one or more signal parameter values on a pulse-by-pulse basis. This technique may provide for a more robust stimulation technique compared to the burst pattern encoding technique because each pulse in the burst may be generated according to a different set of signal parameters. INS 26 may encode information in the stimulation signal by associating particular pulse shapes with an alphanumeric identifier or patterns in pulse shapes with alphanumeric identifiers, and may arrange the alphanumeric identifiers to form words or other indicators that have a unique predetermined meaning. ICD 16 may decode the stimulation signal using the same coding scheme with which INS 26 encoded the stimulation signal. In other examples, INS 26 may encode information in the stimulation signal by associating particular pulse shapes with respective instructions for ICD 16, such as an instruction relating to a modification to a sensing parameter. In this manner, INS 26 may be configured to encode information in stimulation signals using well known techniques in the art of telecommunication.

Although INS 26 is primarily described herein as generating pulse waveforms, INS 26 may also generate continuous time signals, such as sine waves, and vary stimulation parameters including a slew rate, a signal amplitude, a signal frequency, and a signal phase in order to encode information in the signal.

ICD 16 and INS 26 may also communicate with each other via stimulation signals, but without encoding information in the stimulation signal. For example, ICD 16 may communicate with INS 26 by delivering a defibrillation pulse to heart 14. In this example, the defibrillation pulse itself may be considered information that the INS 26 receives. INS 26 may suspend the delivery of neurostimulation upon receiving or sensing the defibrillation pulse, or may begin delivering neurostimulation that provides therapeutic benefits after a predetermined period of time has passed following the defibrillation pulse.

Examples of information that INS 26 may encode in a stimulation signal include, but are not limited to, therapy information, operational information, diagnostic information, and message information. Therapy information may include a duration and type of therapy, as well as signal parameter values of the neurostimulation signals. For example, therapy information may include a duration of a therapy session in which INS 26 will be actively delivering electrical stimulation signals and/or the type of therapy delivered by INS 26. INS 26 may encode information indicating the duration of the therapy session by encoding information relating to a stop time of the therapy delivery, a start time and a stop time of the therapy delivery, a total duration of time of the therapy delivery or the time remaining in the current therapy session. As another example, INS 26 may encode the type of therapy by specifying the particular therapy program with which INS 26 is generating the stimulation signals (e.g., by identifying the therapy program by an alphanumeric identifier and transmitting the identifier to ICD 16), or by specifying the therapy program parameters.

In another example, INS 26 may encode operational information in a stimulation signal. Operational information may include information that specifies the operational mode of INS 26. For example, the operational information may indicate that INS 26 is being recharged or is actively delivering stimulation signals to patient 14. INS 26 may encode the type of operation by identifying the type of operation by an alphanumeric identifier and transmitting the identifier to ICD 16.

In an additional example, INS 26 may encode diagnostic information in a stimulation signal. Diagnostic information may include information about the status of INS 26 or its leads. For example, the diagnostic information may include measured lead impedance values. The lead impedance values may be used for detecting lead-related conditions (e.g., a fractured conductor, a compromised electrical insulation, and the like). In some examples, INS 26 may transmit lead impedance values on a periodic basis, e.g., a daily basis, and ICD 16 may generate a combined INS 26/ICD 16 lead impedance trend. This may allow a clinician to interrogate only one device, e.g., ICD 16, to retrieve system specific diagnostic information.

In a further example, INS 26 may encode transmission information that includes message information and/and acknowledgement information. INS 26 may encode message information at one of or both of the beginning and end of a stimulation signal. The message information may include a header that indicates the beginning of the message and a footer than indicates the end of the message. In this way, ICD 16 may use the header to locate the beginning of the therapy, operational, and/or diagnostic information and the footer to confirm that the message has been transmitted properly. INS 26 may encode acknowledgement information in a stimulation signal in examples in which ICD 16 transmits information to INS 26. The acknowledgement information may indicate to INS 26 that the information transmitted by INS 26 has been received by ICD 16. Accordingly, ICD 16 may transmit acknowledgement information to INS 26 in response to receiving one or more of therapy information, operational information, and diagnostic information.

In examples in which ICD 16 transmits information to INS 26, ICD 16 may encode therapy information in a stimulation signal. The therapy information may indicate to INS 26 that ICD 16 is delivering therapy and, may also indicate the type of therapy. For example, the therapy information may indicate prospective delivery a stimulation pulse by that ICD 16 to allow that INS 26 to suspend delivery neurostimulation or take another appropriate action to synchronize therapy delivery to the operation of ICD 16. As another example, the therapy information may indicate the type and duration of therapy to be delivered by ICD 16, so that INS 26 can begin delivering neurostimulation therapy that benefits the cardiac therapy after ICD 16 has finished delivering cardiac therapy. As an additional example, INS 26 may be configured to recognize a defibrillation pulse delivered by ICD 16 so that a defibrillation pulse itself indicates to INS 26 to stop delivering neurostimulation. In such examples, INS 26 may transmit acknowledgement information to ICD 16 upon receiving therapy information from ICD 16, and ICD 16 may begin to deliver therapy after receiving acknowledgement information from INS 26.

Again, techniques well known in the art of telecommunications may be used to encode this information, e.g., therapy information, operational information, diagnostic information, and message information in stimulation signals generated by INS 26. Similarly, techniques well known in the art of telecommunications may be used to encode therapy information in stimulation signals generated by ICD 16.

ICD 16 may be configured to sense the electrical stimulation signal generated by INS 26 and process the signal to retrieve the encoded information. For example, ICD 16 may include signal processing circuitry for detecting the signal artifact in the sensed signal and decoding the information. ICD 16 may then use the decoded information to modify its operation. For example, if the information encoded in the stimulation signal specifies the duration of a therapy session during which INS 26 will deliver electrical stimulation, ICD 16 may suspend the delivery of pacing, cardioversion or defibrillation signals to patient 12 in order to prevent delivering therapy in response to a cardiac arrhythmia that is detected based on the electrical stimulation signal delivered by INS 26, rather than a true cardiac signal. In another example, ICD 16 may invoke additional signal processing methods while INS 26 delivers therapy, where the additional signal processing methods utilize more complex techniques for monitoring the cardiac signal so as not to deliver unnecessary stimulation therapy to heart 14. The additional signal processing techniques may involve processing the sensed signal to remove the signal artifact resulting from the stimulation. In an example in which the therapy information specifies the type of therapy delivered by INS 26, ICD 16 may modify its operation accordingly, for example by changing pacing and/or therapy parameters based on the received information.

Although interdevice communication has generally been described as one-way from INS to ICD 16, ICD 16 and INS 26 may also be configured for two-way communication. ICD 16 may encode therapy information in a pacing, cardioversion or defibrillation signal that is coupled to INS 26 through tissue of patient 14 and INS 26 may be configured to retrieve the information from the sensed electrical activity.

Therapy system 10 may implement various techniques described herein to reduce the amount of crosstalk between INS 26 and ICD 16. As one example, INS 26 may be configured to generate a stimulation signal characterized by a predetermined signature. INS 26 may vary one or more signal parameters, e.g., slew rate, frequency (e.g., pulse rate), signal duration (e.g., pulse width), phase, and duty cycle, to generate the stimulation signal with the signature. In examples in which INS 26 generates the stimulation signal as a plurality of bursts of pulses, the signature may comprise a plurality of bursts of pulses. In examples in which INS 26 generates the stimulation signal as a substantially continuous series of pulses or substantially continuous waveform, the signature may be characterized by a signal envelope that traces the outline of the amplitude of the stimulation signal for a given period of time. ICD 16 may be configured to process a sensed electrical signal to substantially remove the signal artifact attributable to the delivery of stimulation signals by INS 26. For example, ICD 16 may include one or more filters designed to at least partially remove the signal artifact from the sensed signal. ICD 16 may analyze the processed signal, i.e., the signal with the reduced artifact, to monitor cardiac events and deliver cardiac rhythm management therapy.

As an additional example, INS 26 may be configured to generate a stimulation signal that has a narrow band energy spectrum centered at a predetermined frequency. The predetermined frequency may be selected as a frequency that does not generally interfere with the cardiac signal. Accordingly, ICD 16 may be configured to process the sensed signal to substantially remove the signal artifact from the sensed signal, for example, by applying a narrowband notch filter centered at the predetermined frequency to the sensed signal.

As another example, INS 26 may be configured to vary one or more signal parameters to mitigate the artifact present in electrical signals sensed by ICD 16. In particular, INS 26 may randomly or pseudo-randomly vary one or more signal parameters, e.g., slew rate, frequency (pulse rate), pulse width, phase, and duty cycle, to generate a stimulation signal with a spread spectrum energy distribution. The spread spectrum energy distribution of the stimulation signal may cause the resulting signal artifact to appear as wideband noise in the sensed signal at ICD 16. For example, the wideband noise may be spread over a frequency range of approximately 2.5 Hz to approximately 100 Hz, although other frequency ranges are contemplated. ICD 16 may employ signal processing techniques known in the art to substantially remove or suppress wideband noise. For example, Wiener filtering or adaptive noise cancellation schemes (e.g., a least means square approach) may be used to filter the wideband noise from a sensed signal. A Wiener filter may reduce the amount of noise present in a sensed signal by comparison with an estimation of the desired noiseless signal.

Alternatively, the resulting "wideband noise" may be such that ICD 16 may employ well known signal processing techniques for monitoring cardiac activity. In other words, ICD 16 may not need to be configured to include additional processing features for removing the resulting "wideband noise."

Programmer 24 of therapy system 10 may include a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with ICD 16 and/or INS 26. For example, the user may interact with programmer 24 to retrieve physiological or diagnostic information from ICD 16 and/or INS 26. A user may also interact with programmer 24 to program ICD 16 and INS 26, e.g., select values for operational parameters of ICD 16 and INS 26, respectively.

For example, the user may use programmer 24 to retrieve information from ICD 16 regarding the rhythm of heart 14, trends therein over time, or tachyarrhythmia episodes. As another example, the user may use programmer 24 to retrieve information from ICD 16 regarding other sensed physiological parameters of patient 12, such as electrical depolarization/repolarization signals from the heart (referred to as EGM), intracardiac or intravascular pressure, activity, posture, respiration, or thoracic impedance. As another example, the user may use programmer 24 to retrieve information from ICD 16 regarding the performance or integrity of ICD 16 or other components of system 10, such as leads 18, 20, and 22, or a power source of ICD 16.

The user may use programmer 24 to program a therapy progression, select electrodes used to deliver defibrillation pulses, select waveforms for the defibrillation pulse, or select or configure a fibrillation detection algorithm for ICD 16. The user may also use programmer 24 to program aspects of therapy provided by ICD 16, such as cardioversion or pacing therapies. In some examples, the user may activate certain features of ICD 16 by entering a single command via programmer 24, such as depression of a single key or combination of keys of a keypad or a single point-and-select action with a pointing device.

As another example, the user may use programmer 24 to retrieve information from INS 26 regarding the performance or integrity of INS 26 or lead 28, or a power source of INS 26. With the aid of programmer 24 or another computing device, a user may select values for therapy parameters for controlling therapy delivery by INS 26. The values for the therapy parameters may be organized into a group of parameter values referred to as a "therapy program" or "therapy parameter set." "Therapy program" and "therapy parameter set" are used interchangeably herein.

In the case of electrical stimulation, the therapy parameters for INS 26 may include an electrode combination and an amplitude, which may be a current or voltage amplitude, and, if INS 26 delivers electrical pulses, a pulse width and a pulse rate for stimulation signals to be delivered to patient 12. The therapy parameters may also include phase of the signal or a duty cycle of the signal. The therapy parameters may also be modulated to vary the rise and fall time of a soft start/stop signal. A soft/start stop signal is a signal in which the amplitude is gradually increased at the onset of therapy from a low value to a maximum value and subsequently gradually decreased back to the low value. Thus, INS 26 may encode information in a stimulation signal by varying one or more of the low amplitude value, the maximum amplitude value, and the rise and fall times between the low and maximum value. An electrode combination may include a selected subset of one or more electrodes 46 located on implantable lead 28 coupled to INS 26. The electrode combination may also refer to the polarities of the electrodes in the selected subset. By selecting particular electrode combinations, a clinician may target particular anatomic structures within patient 12. In addition, by selecting values for signal parameters such as, amplitude, pulse width, pulse rate, phase, and duty cycle, the physician can attempt to generate an efficacious therapy for patient 12 that is delivered via the selected electrode subset.

Programmer 24 may communicate with ICD 16 and INS 26 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the ICD 16 and INS 26 implant sites in order to improve the quality or security of communication between ICD 16 or INS 26, respectively, and programmer 24.

Figure 2:
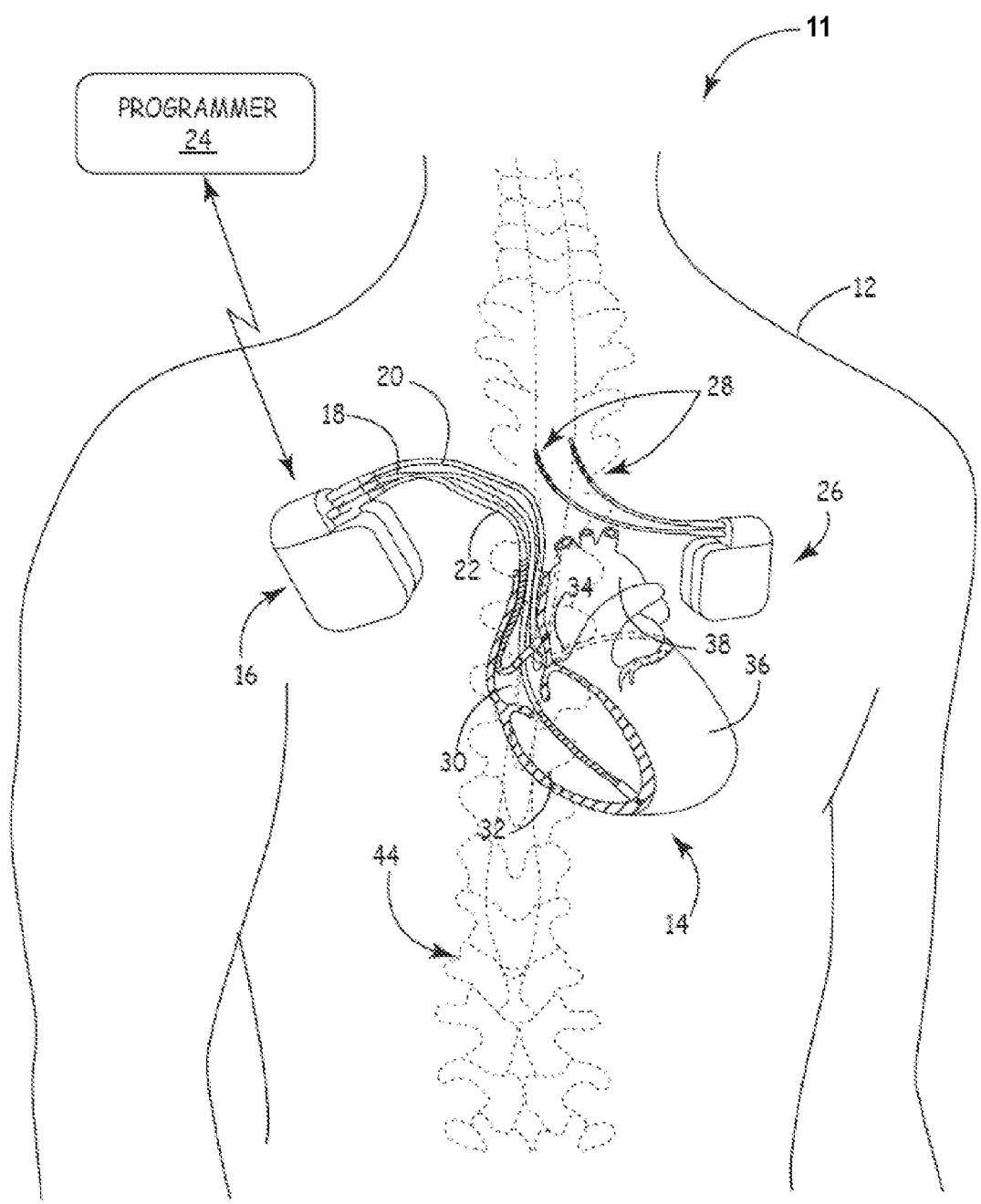
FIG. 2 is a conceptual diagram illustrating another example configuration of the therapy system of FIG. 1.

FIG. 2 is a conceptual diagram illustrating another example of therapy system 11. As shown in FIG. 2, INS 26 and lead 28 may be positioned to deliver electrical stimulation to spinal cord 44 of patient 12. Stimulation of spinal cord 44 or nerves branching therefrom by INS 26 may help prevent or mitigate occurrences of tachyarrhythmias and may reduce the level of aggressiveness of the cardiac therapy, such as pacing, cardioversion or defibrillation, delivered by ICD 16. In this way, ICD 16 and INS 26 may operate in conjunction with each other to help prevent arrhythmias of heart 14 of patient 12, as well as to terminate detected arrhythmias.

In the example shown in FIG. 2, in therapy system 11, INS 26 is coupled to two leads 28, 29 to provide bilateral stimulation of spinal cord 44. Leads 28, 29 may be introduced into spinal cord 44 in the thoracic region, as shown in FIG. 2. In other examples, leads 28, 29 may be introduced into spinal cord 44 in the cervical or lumbar regions. Electrodes of leads 28, 29 may be positioned within an intrathecal space or epidural space of spinal cord 44, or, in some examples, adjacent nerves that branch off of spinal cord 44. In some examples, leads 28, 29 are implanted within patient 12 and positioned such that electrodes of leads 28, 29 deliver electrical stimulation to locations proximate to the T1 to T6 thoracic vertebrae of the patient's vertebral column. For example, electrodes of at least one of the leads 28, 29 may span the T3 to T6 thoracic vertebrae or deliver electrical stimulation to a tissue site proximate at least one of the T3 to T6 thoracic vertebrae. In other examples, leads 28, 29 may be implanted to deliver electrical stimulation to other regions proximate or within spinal cord 44, such as over or near other vertebrae.

Figure 3:
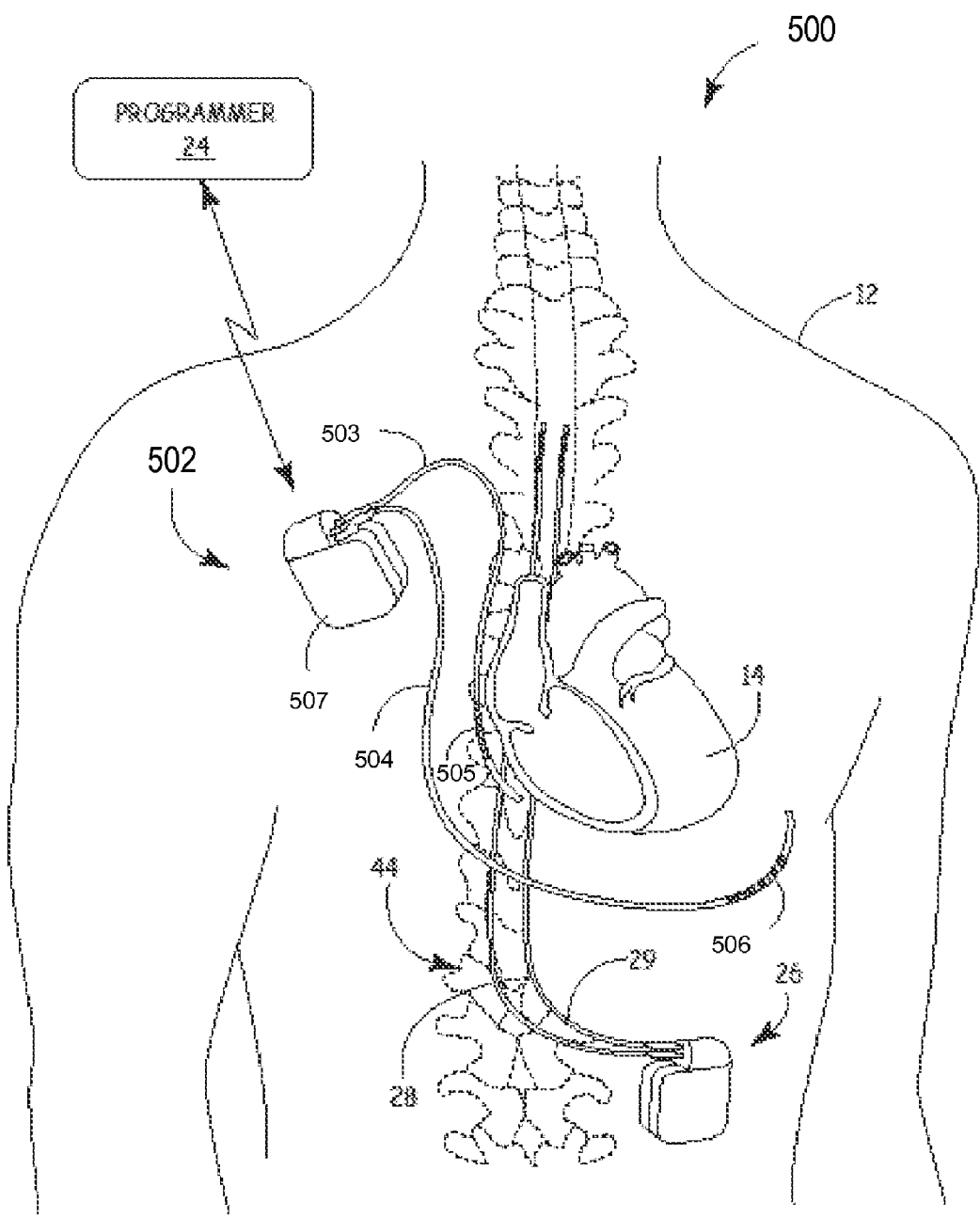
FIG. 3 is a conceptual diagram illustrating an example therapy system.

FIG. 3 is a conceptual diagram illustrating another example therapy system 500 that includes two medical devices to provide therapy to patient 12. In addition to INS 26, therapy system 500 includes ICD 502, which delivers electrical stimulation to heart 14 via extravascular leads 503, 504. Extravascular leads 503, 504 each include at least one electrode 505, 506, respectively. Electrodes 505, 506 may be subcutaneous coil electrodes, which may be positioned within a subcutaneous tissue layer of patient 12. In other examples, electrodes 505, 506 may comprise any other suitable type of extravascular electrode. For example, electrodes 505, 506 may include any other type of subcutaneous electrode, such as subcutaneous ring electrodes, subcutaneous plate electrodes, subcutaneous patch or pad electrodes, or an extrathoracic electrode, a submuscular electrode, an epicardial electrode or an intramural electrode.

Electrode 505 may be located within the right ventricular cavity of the patient's chest, on the patient's side or back, or any other portion of the body appropriate for providing electrical stimulation to heart 14. Electrode 506 may be located within the left ventricular cavity of the patient's chest, on the patient's side or back, or any other portion of the body appropriate for providing electrical stimulation to the heart. Similar extravascular electrodes are disclosed in commonly-assigned U.S. Pat. No. 5,261,400 to Bardy, which is entitled "DEFIBRILLATOR EMPLOYING TRANSVENOUS AND SUBCUTANEOUS ELECTRODES AND METHOD OF USE" and issued Nov. 16, 1993, and U.S. Pat. No. 5,292,338 to Bardy, which is entitled "ATRIAL DEFIBRILLATOR EMPLOYING TRANSVENOUS AND SUBCUTANEOUS ELECTRODES AND METHOD OF USE" and issued Mar. 8, 1994. U.S. Pat. Nos. 5,261,400 and 5,292,338 are incorporated herein by reference in their entireties.

Leads 503, 504 may be electrically coupled to a stimulation module, and, in some cases, a sensing module that are enclosed within housing 507 of ICD 502. Housing 507 may comprise a hermetic housing that substantially encloses the components of ICD 502, such as a sensing module, stimulation module, processor, memory, telemetry module, power source, and the like. Components of an example ICD 16 and ICD 502 are described with respect to FIG. 7. ICD 502 may deliver electrical stimulation (e.g., pacing, cardioversion or defibrillation pulses) to heart 14 between electrodes 505, 506, e.g., in a bipolar configuration. In other examples, ICD 502 may deliver electrical stimulation to heart 14 between electrodes 505 and housing 507, or between electrode 506 and housing 507, e.g., in a unipolar configuration.

Just as with ICD 16 (FIGS. 1 and 2) that delivers stimulation to heart 14 via intravascular electrodes, the delivery of electrical stimulation by INS 26 may interfere with the ability of ICD 502 to sense cardiac signals and deliver appropriate therapy upon the detection of an arrhythmia. ICD 502 may include a sensing module similar to that of ICD 16. In some cases, the sensing module may sense the electrical stimulation delivered by INS 26 and mischaracterize the signals as cardiac signals, which may cause ICD 502 to deliver inappropriate therapy to heart 14 of patient 12.

While the disclosure primarily refers to therapy system 10 including ICD 16 (FIGS. 1 and 2) and INS 26, the description of the techniques, systems, and devices herein are also applicable to therapy system 500 including ICD 502 and INS 26.

Figure 4:
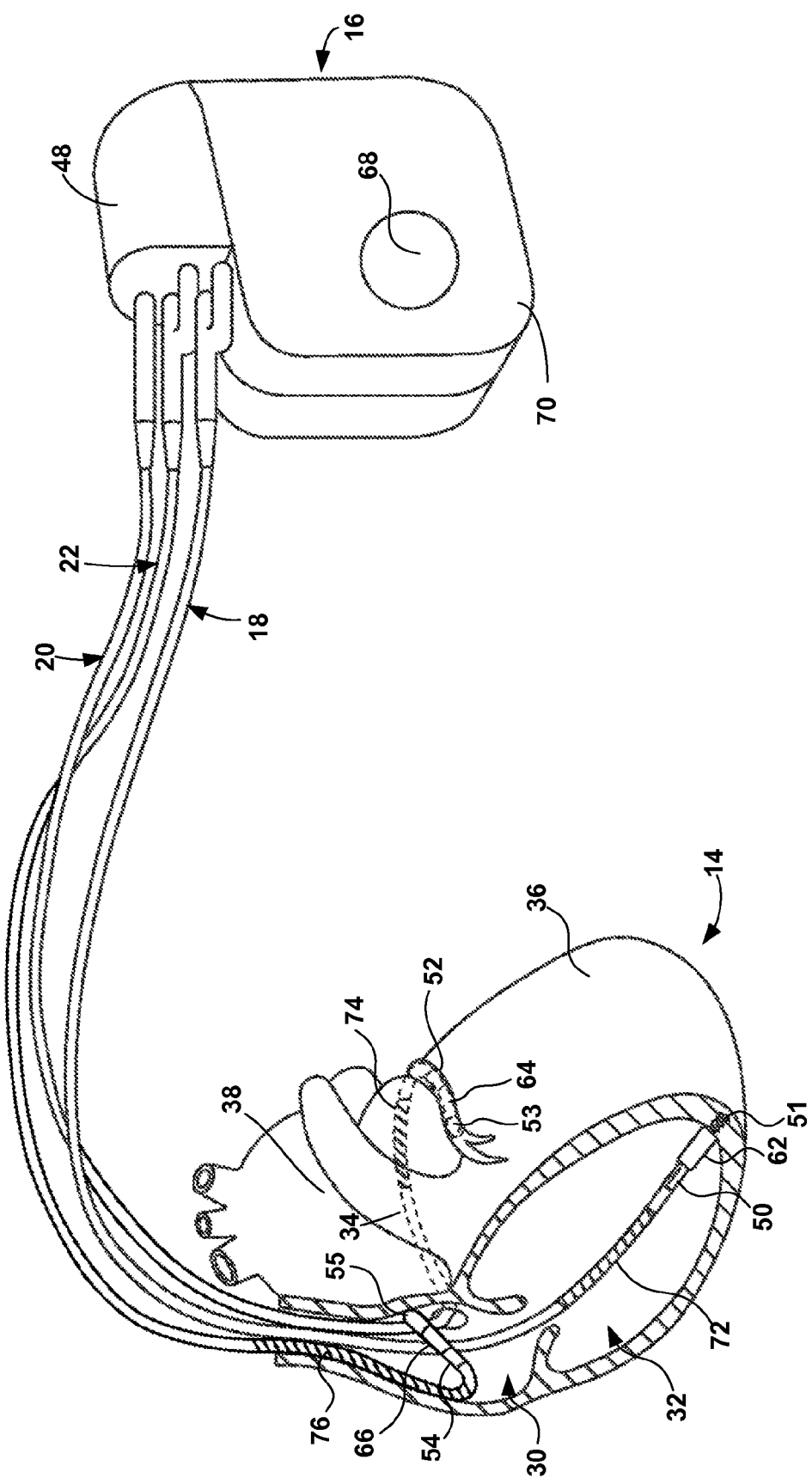
FIG. 4 is a conceptual diagram illustrating an example configuration of the ICD and leads attached to the ICD of FIG. 1 in greater detail.

FIG. 4 is a conceptual diagram illustrating ICD 16 and leads 18, 20, 22 of therapy system 10 in greater detail. Leads 18, 20, 22 may be electrically coupled to a stimulation generator, a sensing module, or other modules of ICD 16 via connector block 48. In some examples, proximal ends of leads 18, 20, 22 may include electrical contacts that electrically couple to respective electrical contacts within connector block 48. In addition, in some examples, leads 18, 20, 22 may be mechanically coupled to connector block 48 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 50 and 51 are located proximate to a distal end of lead 18. In addition, bipolar electrodes 52 and 53 are located proximate to a distal end of lead 20 and bipolar electrodes 54 and 55 are located proximate to a distal end of lead 22.

Electrodes 50, 52, and 54 may take the form of ring electrodes, and electrodes 51, 53, and 55 may take the form of extendable helix tip electrodes retractably mounted within insulative electrode heads 62, 64, and 66, respectively. Each of the electrodes 50-55 may be electrically coupled to a respective one of the conductors within the lead body of its associated lead 18, 20, 22, and thereby coupled to respective ones of the electrical contacts on the proximal end of leads 18, 20 and 22.

Electrodes 50-55 may sense electrical signals attendant to the depolarization and repolarization of heart 14. The electrical signals are conducted to ICD 16 via the respective leads 18, 20, 22. In some examples, ICD 16 also delivers pacing pulses via electrodes 50-55 to cause depolarization of cardiac tissue of heart 14. In some examples, as illustrated in FIG. 3, ICD 16 may include one or more housing electrodes, such as housing electrode 68, which may be formed integrally with an outer surface of hermetically-sealed housing 70 of ICD 16 or otherwise coupled to housing 70. In some examples, housing electrode 68 is defined by an uninsulated portion of an outward facing portion of housing 70 of ICD 16. Other division between insulated and uninsulated portions of housing 70 may be employed to define two or more housing electrodes. In some examples, housing electrode 68 comprises substantially all of housing 70. Any of the electrodes 50-55 may be used for unipolar sensing or pacing in combination with housing electrode 68. As described in further detail with reference to FIG. 7, housing 70 may enclose a stimulation generator that generates cardiac pacing pulses and defibrillation or cardioversion shocks, as well as a sensing module for monitoring electrical cardiac signals of heart 14.

Leads 18, 20, 22 also include elongated electrodes 72, 74, 76, respectively, which may take the form of a coil. ICD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

Figure 5:
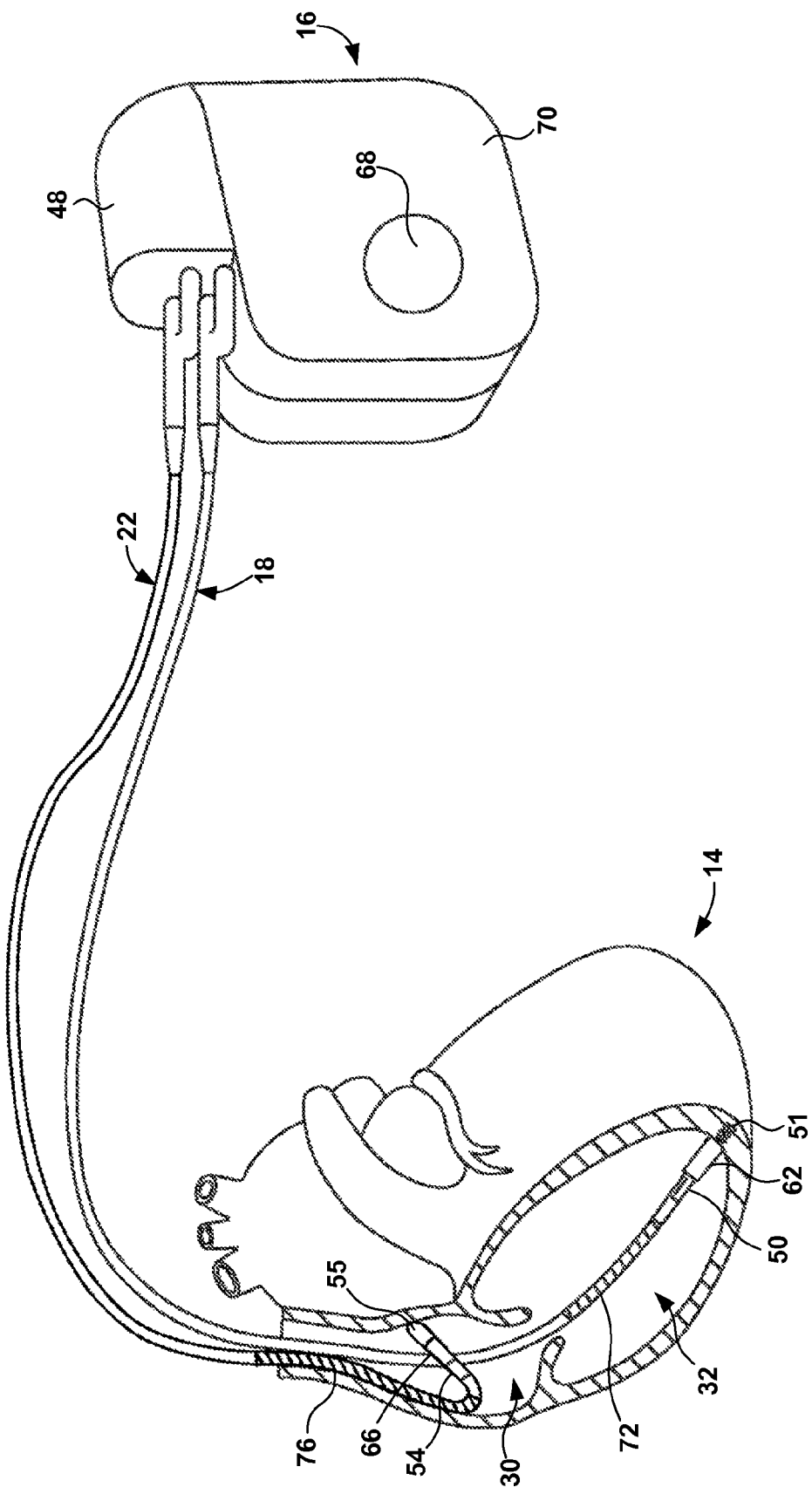
FIG. 5 is a conceptual diagram illustrating another example configuration of the ICD and attached leads in greater detail.

FIG. 5 is a conceptual diagram illustrating another example configuration of ICD 16 for use in therapy system 10. As shown in FIG. 5, ICD 16 may be configured to include two leads 18 and 22 in some examples, rather than three leads as illustrated in FIG. 4. In the two lead configuration shown in FIG. 5, leads 18, 22 are implanted within right ventricle 32 and right atrium 30, respectively, and may be useful for providing cardioversion, defibrillation, and pacing pulses to heart 14. Therapy system 10 may include ICD 16 as shown in FIG. 5 and INS 26 which is configured to deliver electrical stimulation therapy to a nonmyocardial or nonvascular cardiac tissue site within patient 14 in order to help prevent or mitigate an arrhythmia of patient 16, to treat heart failure or to provide other cardiac benefits to patient 12.

The configuration of therapy system 10 and ICD 16 illustrated in FIGS. 1, 2, 4, AND 5 are merely examples. In other examples, a therapy system may include epicardial leads and/or patch electrodes instead of or in addition to the transvenous leads 18, 20, 22 illustrated in FIG. 1. Further, ICD 16 and INS 26 need not be implanted within patient 12. In examples in which ICD 16 is not implanted in patient 12, ICD 16 may deliver defibrillation pulses and other therapies to heart 14 via percutaneous leads that extend through the skin of patient 12 to a variety of positions within or outside of heart 14 or via external electrodes. In examples in which INS 26 is not implanted in patient 12, INS 26 may deliver electrical stimulation to target tissue sites or sense stimulation delivered by ICD 16 within patient 12 via external electrodes or via percutaneous leads that extend through the skin of patient 12.

In other examples of therapy systems that provide electrical stimulation therapy to heart 14, a therapy system may include any suitable number of leads coupled to ICD 16, and each of the leads may extend to any location within or proximate to heart 14. For example, other examples of therapy systems may include three transvenous leads located as illustrated in FIGS. 1 and 2, and an additional lead located within or proximate to left atrium 38. As another example, other examples of therapy systems may include a single lead that extends from ICD 16 into right atrium 30 or right ventricle 32, or two leads that extend into a respective one of the right ventricle 32 and right atrium 30. In addition, in other examples, a therapy system may include extravascular electrodes for providing pacing, cardioversion or defibrillation pulses to heart 14, as described with respect to FIG. 3.

Figure 6:
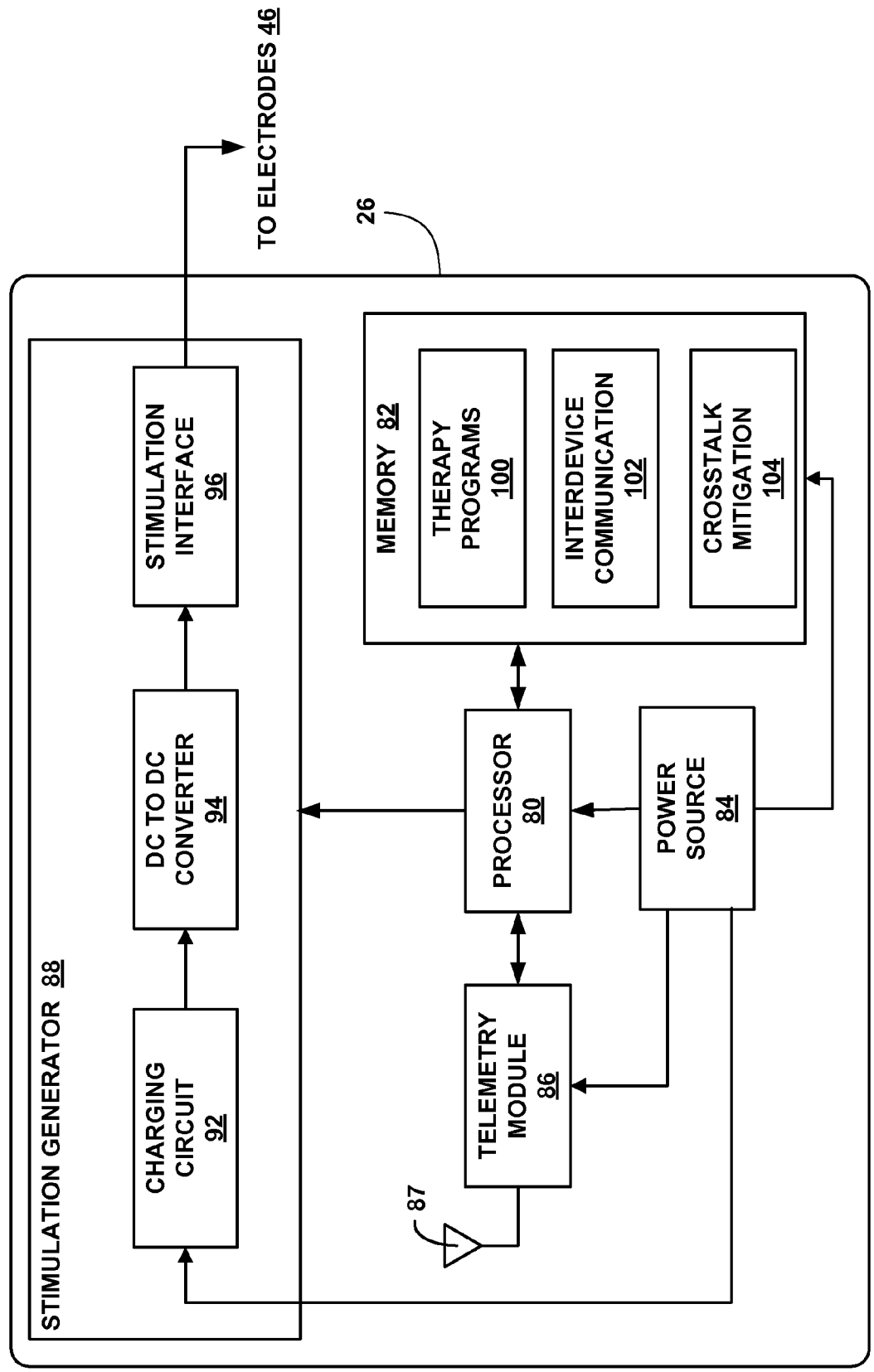
FIG. 6 is a functional block diagram of an example INS.

FIG. 6 is a functional block diagram of an example INS 26. INS 26 includes processor 80, memory 82, power source 84, telemetry module 86, and stimulation generator 88. In the example shown in FIG. 6, processor 80, memory 82, power source 84, telemetry module 86, and stimulation generator 88 are enclosed within the housing of INS 26 which may be, for example, a hermetic housing. As shown in FIG. 6, stimulation generator 88 is coupled to electrodes 46 carried by lead 28 either directly or indirectly (e.g., via a lead extension). In other examples, such as in the example shown in FIG. 2, stimulation generator 88 may be coupled to more than one lead directly or indirectly (e.g., via a lead extension such as a bifurcating lead extension that may electrically and mechanically couple to two leads) as needed to provide neurostimulation therapy to patient 12.

Processor 80 may include any one or more microprocessors, controllers, a digital signal processor (DSP), an application specific integrated circuit (ASIC), a field-programmable gate array (FPGA), or equivalent discrete or integrated digital or analog logic circuitry. The functions attributed to processor 80 herein may be embodied as software, firmware, hardware or any combination thereof. Processor 80 controls stimulation generator 88 to generate and deliver electrical stimulation signals to patient 12. Processor 80 may set and adjust stimulation parameter values with which stimulation generator 88 generates electrical stimulation signals, e.g., based on stored therapy programs 100 and other instructions stored in memory 82, as described in further detail below. In examples in which stimulation generator 88 generates electrical stimulation pulses, the stimulation parameters may include, for example, a slew rate, a pulse amplitude, pulse rate (frequency), pulse width (duration), phase, and duty cycle. In other examples, stimulation generator 88 may generate continuous electrical signals, e.g., a sine wave, in which case the stimulation parameters may include a signal amplitude, signal width, and signal frequency.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 stores computer-readable instructions that, when executed by processor 80, cause INS 26 to perform various functions. For example, memory 82 may stores instructions for execution by processor 80, including operational commands and programmable parameter settings. Example storage areas of memory 82 may include instructions associated with therapy programs 100, interdevice communication features 102, and crosstalk mitigation features 104.

Therapy programs 100 may be stored as individual therapy programs and/or organized into therapy program groups that include one or more therapy programs. The therapy programs may define a particular program of therapy in terms of respective values for electrical stimulation parameters. A therapy program group may comprise a plurality of therapy programs that may be delivered together on an overlapping or non-overlapping basis. The stored operating instructions may guide the general operation of INS 26 under control of processor 80.

Interdevice communication features 102 may include instructions for encoding information in a stimulation signal generated by stimulation generator 88 and decoding information received from ICD 16. The instructions may include instructions for selecting the information that is encoded and signal parameter variation instructions for encoding the selected information in the stimulation signal. As previously, information that processor 80 may encode in a stimulation signal include, but is not limited to, therapy information, such as the start and stop times for a therapy session in which stimulation generator 88 delivers stimulation therapy to patient 12, the duration of the therapy session, the time remaining in a current therapy session, the type of stimulation, and the stimulation parameter values of stimulation delivered by INS 26 in a particular therapy session, operational information, diagnostic information, and message information.

Crosstalk mitigation features 104 may include instructions that processor 80 may execute to control stimulation generator 88 to generate a stimulation signal that may minimize the neurostimulation artifact present in an electrical signal sensed by ICD 16. In one example, crosstalk mitigation features 104 include instructions for generating a stimulation signal with a predetermined signature. In an additional example, crosstalk mitigation features 104 include signal parameter instructions for generating a stimulation signal with a narrowband energy spectrum centered at a predetermined frequency. In another example, crosstalk mitigation features 104 may store instructions for generating a stimulation signal with a spread spectrum energy distribution.

It should be understood that although INS 26 is described as implementing the interdevice communication and crosstalk mitigation functions for reducing the neurostimulation signal artifact present in an electrical signal sensed by ICD 16, INS 26 may be configured to implement only one of these functions. Accordingly, memory 82 may include only one of interdevice communication 102 and crosstalk mitigation features 104.

Stimulation generator 88 generates stimulation signals, which may be pulses as primarily described herein, or continuous time signals, such as sine waves, for delivery to patient 12 via selected subset of electrodes 46. In particular, processor 80 may control stimulation generator 88 according to stored therapy programs 100, interdevice communication features 102, and/or crosstalk mitigation features 104 loaded from memory 82 to produce an electrical stimulation signal with particular stimulation parameter values, such as amplitude, frequency, phase, and duty cycle, and, in the case of stimulation pulses, pulse width and pulse rate. As shown in FIG. 6, stimulation generator 88 may include a charging circuit 92, a DC to DC converter 94, and a stimulation interface 96.

DC to DC converter 94 is primarily described as a capacitor module, but this disclosure is not limited to examples in which DC to DC converter 94 is a capacitor module. In other examples, DC to DC converter 94 may comprise, for example, an inductor-based charge pump, a capacitor-based charge pump, and/or any other type of DC to DC converter.

Charging circuit 92 selectively, e.g., based on signals from processor 80, applies energy from power source 84 to DC to DC converter 94 to charge the capacitor module for delivery of a stimulation signal, e.g., pulse. For delivery of pulses, charging circuit 92 may control the pulse rate by controlling the rate at which DC to DC converter 94 is recharged. Similarly, charging circuit 92 may also control the duty cycle. In addition to capacitors, DC to DC converter 94 may include switches. In this manner, capacitor module 94 may be configurable, e.g., based on signals from stimulation control module 90, to store a desired voltage for delivery of stimulation at a voltage or current amplitude specified by a program. For delivery of stimulation pulses, switches within capacitor module 94 may control the width of the pulses based on signals from processor 80.

Stimulation interface 96 conditions charge from capacitor module 94 to produce an electrical stimulation signal, e.g., a pulse, under control of processor 80 for application to a subset of electrodes 46 carried by lead 28. Stimulation interface 96 may control the voltage or current amplitude, or shape of the signal based on signals from stimulation control module 90. Stimulation generator 88 is coupled to electrodes 46 via stimulation interface 96 and conductors within leads 28. Stimulation interface 96 may control the subset of electrodes 46 that are selected to deliver the stimulation signal to patient 12 and the polarities of the selected electrodes based on signals from processor 80. For example, processor 80 may control stimulation interface 96 to apply the stimulation signals to selected combinations of electrodes 46. In particular, stimulation interface 96 may couple stimulation signals to selected conductors within lead 28, which may deliver the stimulation signals across the selected electrodes 46. Stimulation interface 96 may include a switch array, switch matrix, multiplexer, or any other type of switching device suitable to selectively couple stimulation energy to selected electrodes. In some examples, INS 26 does not include stimulation interface 96.

Stimulation generator 88 may be a single or multi-channel stimulation generator. In particular, stimulation generator 88 may be capable of delivering a single stimulation pulse, multiple stimulation pulses (as a series of pulses or as a burst/train of pulses) or a continuous signal at a given time via a single electrode combination or multiple stimulation pulses at a given time via multiple electrode combinations. In some examples, however, stimulation generator 88 and stimulation interface 96 may be configured to deliver stimulation signals to one or more channels on a time-interleaved basis. In this case, stimulation interface 96 serves to time division multiplex the stimulation signal across different electrode combinations at different times to deliver multiple programs or channels of stimulation energy to patient 12.

In one example, processor 80 may control operation of stimulation generator 88 to encode information in a stimulation signal that provides therapeutic benefits to patient 12. In another example, processor 80 may control operation of stimulation generator 88 to reduce crosstalk between INS 26 and ICD 16, e.g., by producing a stimulation signal having predetermined characteristics in order to facilitate removal of the resulting signal artifact by ICD 16, or by generating a stimulation signal comprising one or more characteristics that reduces the possibility that ICD 16 senses the electrical stimulation signal generated by INS 26 and mischaracterizes the signal as a cardiac signal. These examples are described in greater detail below.

In examples in which processor 80 controls stimulation generator 88 to encode information in a stimulation signal that provides therapy to patient 12, stimulation generator 88 may encode information in the stimulation signal by varying one or more stimulation signal parameters, such as a slew rate, pulse amplitude, pulse rate (frequency), pulse width (duration), phase, and duty cycle. One or more stimulation parameters may be varied at any given time. Example modulation schemes include amplitude modulation, frequency modulation, and on/off keying (OOK), which may be viewed as a form of amplitude modulation. Other modulation schemes are also contemplated, such as modulating a minimum value, a maximum value, or the rise/fall time of a soft start/stop signal. As previously described, the information to be encoded in the stimulation signal may be stored as interdevice communication features 102 in memory 82 and may include therapy information, such as the start and stop times for stimulation therapy, the duration of a particular therapy session, the time remaining for a current therapy session, and the type of stimulation or therapy programs delivered, operational information, diagnostic information, and message information.

In some examples, stimulation generator 88 generates stimulation signals that comprise bursts of pulses, where each burst includes a plurality of pulses. A burst of pulses may also be referred to as a pulse train. Stimulation generator 88 may encode information in a stimulation signal comprising a plurality of bursts by varying signal parameters on a burst-by-burst basis or on a pulse-by-pulse basis. Stimulation generator 88, and INS 26 in general, may be configured to encode information in a stimulation signal in this manner using well known techniques in the art of telecommunication. That is, stimulation generator 88 may employ various known encoding techniques to encode information in a stimulation signal for transmission to ICD 16. The encoding schemes may include, for example, amplitude modulation and/or frequency modulation.

For example, when encoding information on a burst-by-burst basis, stimulation generator 88 may generate each pulse in a burst of pulses using the same signal parameter values. Information may be encoded by associating a particular burst shape with an alphanumeric indicator. The multiple burst shapes may be configured such that the associated alphanumeric indicators form code words for transmitting the desired information or are otherwise associated with desired information. The code words may be assigned a unique predefined meaning or may be arranged to form a message that has a unique predefined message. ICD 16 may sense the stimulation signal and process the sensed electrical signal to identify the burst shapes, and, therefore, extract the encoded alphanumeric indicators from the sensed electrical signal. In other examples, burst shapes may be directly associated with a respective therapy modification instruction or other information that is stored in a memory of ICD 16.

Similarly, in some examples, stimulation generator 88 may encode information in a stimulation signal by associating a plurality of bursts of pulses, referred to herein as a burst pattern, with an alphanumeric indicator. The multiple burst patterns may be arranged to define code words or other alphanumeric codes in order to transmit the desired information to ICD 16. When using burst pattern encoding, stimulation generator 88 may encode information by varying the duty cycle for a burst pattern, or by varying the duty cycle between burst patterns. In other examples, burst pattern may be directly associated with a respective therapy modification instruction or other information that is stored in a memory of ICD 16. Again, ICD 16 may sense the stimulation signal and process the sensed electrical signal to identify the burst pattern, and, therefore, extract the encoded alphanumeric indicators from the sensed electrical signal. In other examples, burst patterns may be directly associated with a respective therapy modification instruction or other information that is stored in a memory of ICD 16.

When encoding information on a pulse-by-pulse basis, stimulation generator 88 may vary one or more signal parameter values for each pulse. That is, stimulation generator 88 may generate each pulse according to a different set of signal parameter values. This encoding technique may provide a greater information rate, i.e., may be used to transmit more information for a given period of time, but may require greater resolution at ICD 16.

Stimulation generator 88 may also encode information by varying one or more signal parameter values in a particular pattern, where the values are varied within an acceptable range of stimulation parameter values that provide efficacious therapy to patient 12. For example, stimulation generator 88 may encode therapy information by varying one or more signal parameters, such as a slew rate, pulse amplitude, pulse rate (frequency) and pulse width (rate), and may encode duration information by varying one or more other signal parameters, such as duty cycle. Varying specific types of signal parameters may permit stimulation generator 88 to encode different types of therapy information. ICD 16 may sense the stimulation signal and process the sensed electrical signal to identify the one or more signal parameter variation patterns, and, therefore, extract the encoded information from the sensed electrical signal. The signal parameter variation patterns may be associated with alphanumeric indicators or directly associated with a respective therapy modification instruction or other information that is stored in a memory of ICD 16.

In order to vary the signal parameters, processor 80 may load stimulation parameter values according to therapy programs 100 stored in memory 82. Therapy programs 100 may each define initial values for generating a stimulation signal. Processor 80 may also load stimulation variation parameter values stored in memory 82 as interdevice communication features 102. The stimulation variation parameter values may provide a range of values over which signal parameters may be varied and instructions for varying the signal parameters to encode the desired information. These stimulation variation parameter values may provide a range of values over which the signal parameter values may be modified without adversely affecting the efficacy of stimulation therapy delivered by INS 16.

In some examples, interdevice communication features 102 may store instructions that permit processor 80 to modify a pulse rate (frequency) for an electrical stimulation signal between approximately 10 Hertz (Hz) and approximately 100

Hz. The interdevice communication features 102 may also store instructions that permit processor 80 to modify a pulse width (duration) of an electrical stimulation signal between approximately 30 microseconds (μs) and approximately 480 μs. The interdevice communication features 102 may also store instructions that permit processor 80 to modify a duty cycle of an electrical stimulation signal between parameter values that indicate stimulation is delivered in a ratio of approximately 20% ON and 80% OFF to approximately 80% ON and 20% OFF.

Stimulation generator 88 may encode information in a stimulation signal in a predetermined order or sequence. Additionally, because INS 26 and ICD 16 may not necessarily be synchronized with each other and communication may be one-way, from INS 26 to ICD 16, the information may be encoded repeatedly in the stimulation signal. Repeating the encoded information may allow ICD 16 to reliably retrieve the encoded information by providing ICD 16 multiple opportunities to sense the stimulation signal and extract the therapy information therefrom.

In some examples, the information may be encoded in the stimulation signal in a sequence that includes a header marking the beginning of the sequence and a predefined sequence of information useful to INS 26, such as therapy information, operational information, and diagnostic information. The stimulation signal may also include a footer marking the end of the information sequence. Again, the header and footer may be referred to as message information. As an example, the predefined sequence may include in order, a header, one or more of therapy information, operational information, and diagnostic information, and a footer. Other orders of encoded information are contemplated, but the header and footer typically remain at the beginning and end, respectively, of the encoded information. The information located between the header and footer may require a variable number of "bits" or "bytes" to transmit the information. The bits or bytes refer to the number of pulses required to transmit the required information. However, in examples in which the number of bits or bytes is fixed for transmitting this information, a footer may not be needed. In other examples, the types of therapy information may be encoded in the stimulation signal in any particular order. In examples in which therapy information is transmitted, processor 80 may access a clock or other timing device within INS 26 to determine pertinent times.

ICD 16 may use the encoded information to modify its operation. For example, as described in further detail below, ICD 16 may blank its sensing circuitry while INS 26 delivers stimulation or may invoke additional signal processing to suppress crosstalk resulting from the stimulation signal output by INS 26.

The example modulation techniques described in this disclosure are not limiting of the scope of the systems, devices, and methods described herein. The purpose of the examples described herein is to provide functional examples and a framework for which more complex systems, that are contemplated within the score of this disclosure, Accordingly, the scope of this disclosure encompasses more any suitable encoding, decoding, and transmission techniques that are well known in the art of telecommunications.

In another example, processor 80 may control operation of stimulation generator 88 to reduce the possibility that ICD 16 may sense stimulation signals generated by INS 26 and mischaracterize the stimulation signals as cardiac signals. For example, processor 80 may control stimulation generator 88 to generate a stimulation signal in a way that facilitates filtering of the electrical stimulation signal generated by INS 26 from a signal sensed by ICD 16, or by producing stimulation signal in a way that reduces the impact of the resulting signal artifact at ICD 16.

Processor 80 may control operation of stimulation generator 88 based on information and/or instructions stored as crosstalk mitigation features 104 loaded from memory 82. As one example, processor 80 may control stimulation generator 88 to generate a stimulation signal with a predetermined signature, which may be stored as crosstalk mitigation features 104 in memory 82. Stimulation generator 88 may vary one or more signal parameters, e.g., a slew rate, pulse rate (frequency), pulse width (rate), phase, and duty cycle, to generate the stimulation signal with the predetermined signature. In particular, stimulation generator may vary one or more signal parameter values from the initial value specified in therapy programs 100 to generate the stimulation signal with the predetermined signature. When stimulation generator 88 generates the stimulation signal as a plurality of pulses, the signature may comprise a plurality of bursts of pulses. When stimulation generator 88 generates the stimulation signal as a continuous waveform, the signature may be characterized by a signal envelope that traces the outline of the stimulation signal for a given period of time. Stimulation generator 88 may generate the stimulation signal so that the predetermined signature repeats throughout the signal.

As an additional example, stimulation generator 88 may generate a stimulation signal that has a narrowband energy spectrum centered at a predetermined frequency. In such an example, crosstalk mitigation features 104 stored in memory 82 may specify signal parameter values that define a stimulation signal having an energy focused within the predetermined frequency band. The predetermined frequency may be selected by a clinician to be frequency that does not generally interfere with a cardiac signal. That is, the predetermined frequency may be selected as a frequency that contains little information for cardiac events.

As will be described in greater detail with respect to FIGS. 6 and 8, in examples in which INS 26 generates and delivers a stimulation signal includes a predetermined signature or a narrow band stimulation signal, ICD 16 may be configured to substantially remove the artifact present in a sensed electrical signal, where the artifact is attributable to a stimulation signal generated by INS 26. The known signature of the stimulation signal and narrowband energy spectrum may allow ICD 16 to relatively easily filter the artifact from a sensed electrical signal. For example, ICD 16 may sense an electrical signal with select electrodes of leads 18, 20, 22 or housing 70 (FIG. 4), and process the sensed electrical signal with a notch filter at the predetermined frequency band in order to filter the stimulation signals out of the sensed electrical signal.

In other examples, processor 80 of INS 26 may control stimulation generator 88 to generate a stimulation signal that has a spread spectrum energy distribution. In particular, stimulation generator 88 may randomly or pseudo-randomly vary one or more signal parameters, e.g., a slew rate, pulse rate (frequency), pulse width (rate), phase, and duty cycle, under the control of processor 80. When stimulation generator 88 outputs a pulse waveform, stimulation generator 88 may vary the one or more signal parameters for each burst, i.e., on a burst-by-burst basis, or for each pulses, i.e., on a pulse-by-pulse basis. Processor 80 may load instructions and/or signal parameters values from crosstalk mitigation features 104 stored in memory 82. The spread spectrum energy distribution of the stimulation signal may cause the signal artifact coupled to ICD 16 to appear as wideband noise in the sensed signal, as described in further detail below with reference to FIGS. 12A and 12B. In addition, as described below with respect to FIGS. 6 and 8, ICD 16 may be configured to suppress the resulting wideband noise or may be configured to remove the wideband noise via processing techniques.

Telemetry module 86 supports wireless communication between INS 26 and an external programmer 24 (FIG. 1) or another computing device under the control of processor 80. Processor 80 of INS 26 may receive, as updates to programs, values for various stimulation parameters such as amplitude and electrode combination, from programmer 24 via telemetry module 86. The updates to the therapy programs may be stored within memory 82. Telemetry module 86 may include an antenna 87, which may take on a variety of forms. Antenna 87 may comprise an internal antenna or an external antenna. For example, antenna 87 may be formed by a conductive coil or wire embedded in a housing associated with INS 26. Alternatively, antenna 87 may be mounted on a circuit board carrying other components of INS 26 or take the form of a circuit trace on the circuit board. In addition, in some examples, telemetry module 86 may support communication between INS 26 and another device (e.g., programmer 24) with the aid of more than one antenna, such as an external antenna and an internal antenna.

The various components of INS 26 are coupled to power supply 84, which may include a rechargeable or non-rechargeable battery. A non-rechargeable battery may be selected to last for several years, while a rechargeable battery may be inductively charged from an external device, e.g., on a daily or weekly basis. In other examples, power supply 84 may be powered by proximal inductive interaction with an external power supply carried by patient 12.

Figure 7:
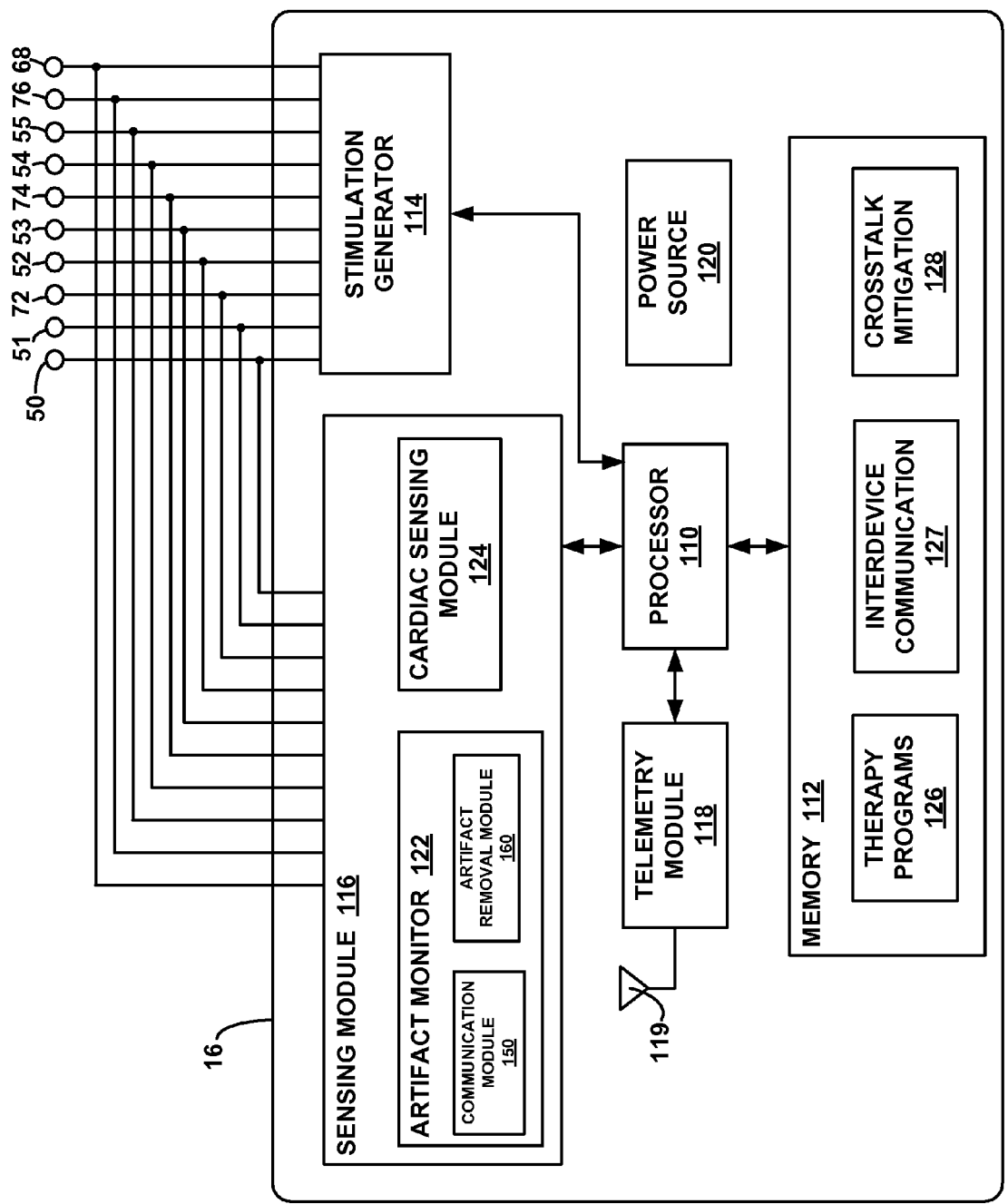
FIG. 7 is a functional block diagram of an example ICD.

FIG. 7 is a functional block diagram of an example configuration of ICD 16, which includes processor 110, memory 112, stimulation generator 114, sensing module 116, telemetry module 118, and power source 120. In general, ICD 16 may monitor electrical activity of heart 14 and deliver cardiac rhythm therapy to heart 14 in the form of pacing, cardioversion, and/or defibrillation pulses. Electrical signals sensed by ICD 16 may include a signal artifact attributable to stimulation delivery by INS 26. As previously described, the signal artifact may be used for communication purposes, i.e., INS 26 may encode information in a stimulation signal, in one example. In other examples, INS 26 may generate a stimulation signal that reduces the signal artifact at ICD 16.

In examples in which INS 26 encodes information in a stimulation signal, ICD 16 may be configured to analyze the sensed electrical signal to retrieve the encoded information. ICD 16 may then modify its operation based on the retrieved information. In examples in which INS 26 generates a stimulation signal to reduce the signal artifact, ICD 16 may be configured to process the sensed signal to substantially remove the signal artifact.

As shown in FIG. 7, sensing module 116 of ICD 16 includes artifact monitor 122 and cardiac sensing module 124. Cardiac sensing module 124 is configured to monitor electrical activity of heart 14 using techniques known in the art of cardiac therapy. Artifact monitor 122 may provide interdevice communication features and crosstalk mitigation features described herein. In particular, communication monitor 150 may be configured to provide interdevice communication features and artifact removal module 160 may be configured to provide crosstalk mitigation features. FIG. 8 provides a more detailed description of communication module 150 and artifact removal module 160. The following paragraphs provide a general description for the operation of ICD 16 with respect to the block diagram illustrated in FIG. 7.

Memory 112 includes computer-readable instructions that, when executed by processor 110, cause ICD 16 and to perform various functions attributed to ICD 16 herein. Memory 112 may include any volatile, non-volatile, magnetic, optical, or electrical media, such as a RAM, ROM, NVRAM, EEPROM, flash memory, or any other digital media. In the example illustrated in FIG. 7, memory 112 includes therapy programs 126, interdevice communication features 127, and crosstalk mitigation features 128. Therapy programs 126 may be stored as individual therapy programs or as therapy program groups. The therapy programs may define a particular program of therapy in terms of respective values for electrical stimulation parameters, such as electrode combination, electrode polarity, current or voltage amplitude, pulse width, and pulse rate. A program group may comprise a plurality of therapy programs that may be delivered together on an overlapping or non-overlapping basis. The stored operating instructions may guide the general operation of therapy delivery by ICD 16 under control of processor 110.

Interdevice communication features 127 may include instructions for analyzing a sensed electrical signal to extract information encoded in the sensed signal. As previously indicated, INS 26 may encode a stimulation signal with one or more alphanumeric identifiers or other therapy information indicators. Interdevice communication features 127 may provide instructions executable by processor 110 to decode information encoded in a sensed signal. In this way, the stimulation signal generated and delivered by INS 26 may also be used to support wireless communication between ICD 16 and INS 26. Processor 110 may also load instructions from interdevice communication features 127 to modify its operation based on the retrieved information. For example, interdevice communication features 127 may provide instructions that, when executed by processor 110, cause processor 110 to time the blanking of sensing circuitry of cardiac sensing module 124 or selectively apply modified signal processing techniques. An example modified signal processing technique may involve applying a matched filter to the sensed signal. In this example, the matched filter may be matched to the stimulation signal or, more particularly, the signal artifact in the sensed signal. ICD 16 may then disregard portions of the sensed signal that are detected by the matched filter. These instructions may be, for example, associated with the alphanumeric identifiers encoded in the sensed stimulation signal or one or more signal characteristics of the sensed stimulation signal.

In some examples, processor 110 may load instructions from crosstalk mitigation features 128 in order to minimize the crosstalk resulting from stimulation therapy delivered by INS 26. In particular, crosstalk mitigation features 128 may provide instructions that guide processor 110 to implement signal processing techniques for filtering out at least some of the neurostimulation artifact from a sensed electrical signal. As an example, the stored instructions may cause processor 110 to load addresses of registers that store the one or more signal parameter values that characterize a predefined electrical stimulation signal signature. As an additional example, instructions stored within crosstalk mitigation features 128 may include instructions for loading addresses of registers that store values for digital filter used for filtering the received signal at a predetermined frequency.

As previously described, ICD 16 may generally be configured to analyze a sensed electrical signal in order to retrieve information encoded in the signal artifact. In addition or instead of decoding a sensed electrical signal to retrieve information communicated by INS 26, ICD 16 may be configured to at least partially remove the signal artifact from a sensed electrical signal. Thus, it should be understood that in some examples, memory 112 may include only one of interdevice communication features 127 or crosstalk mitigation features 128.

Processor 110 may include any one or more of a microprocessor, a controller, a DSP, an ASIC, an FPGA, or equivalent discrete or integrated logic circuitry. In some examples, processor 110 may include multiple components, such as any combination of one or more microprocessors, one or more controllers, one or more DSPs, one or more ASICs, or one or more FPGAs, as well as other discrete or integrated logic circuitry. The functions attributed to processor 110 herein may be embodied as software, firmware, hardware or any combination thereof. Processor 110 controls stimulation generator 114 to deliver stimulation therapy to heart 14 according to a selected one or more of therapy programs 126, which may be stored in memory 112. Specifically, processor 110 may control stimulation generator 114 to deliver therapy to heart 14 in the form of electrical pulses with the amplitudes, pulse widths, frequency, or electrode polarities specified by the selected one or more therapy programs stored as therapy programs 126.

Stimulation generator 114 is electrically coupled to electrodes 50-55, 68, 72, 74, and 76, e.g., via conductors of the respective lead 18, 20, 22, or, in the case of housing electrode 68, via an electrical conductor disposed within housing 70 of ICD 16. Stimulation generator 114 is configured to generate and deliver electrical stimulation therapy to heart 14. For example, stimulation generator 114 may deliver defibrillation shocks to heart 14 via at least two electrodes 68, 72, 74, 76. Stimulation generator 114 may deliver pacing pulses via ring electrodes 50, 52, 54 coupled to leads 18, 20, and 22, respectively, and/or helical electrodes 51, 53, 55 of leads 18, 20, and 22, respectively. In some examples, stimulation generator 114 delivers pacing, cardioversion, or defibrillation stimulation in the form of electrical pulses. In other examples, stimulation generator 114 may deliver one or more of these types of stimulation in the form of other signals, such as sine waves, square waves, or other substantially continuous time signals.

Stimulation generator 114 may include a switch module and processor 110 may use the switch module to select, e.g., via a data/address bus, which of the available electrodes are used to deliver the stimulation pulses. The switch module may include a switch array, switch matrix, multiplexer, or any other type of switching device suitable to selectively couple stimulation energy to selected electrodes. In other examples, however, stimulation generator 114 may independently deliver stimulation to electrodes 50-55, 68, 72, 74, and 76.

As shown in FIG. 7, sensing module 116 includes artifact monitor 122 and cardiac sensing module 124. Generally, sensing module 116 monitors electrical signals from at least two electrodes 50-55, 68, 72, 74, and 76 in order to monitor electrical activity of heart 14, e.g., via EGM signals. In one example, artifact monitor 122 and, more particularly, communication module 150, may process a voltage signal between two or more of electrodes 50-55, 68, 72, 74, and 76 to retrieve information encoded in a stimulation signal output by INS 26. In such an example, artifact monitor 122 (communication module 150) may provide the retrieved information to processor 110 which may then modify operation of ICD 16 based on the retrieved information. For example, processor 110 may reference memory 112 to determine the instruction that is associated with the retrieved information, which may be in the form of, for example, an alphanumeric indicator or another symbolic indicator. Operation of artifact monitor 122 (communicate module 150) and ICD 16 in accordance with such an example is described in greater detail with respect to FIG. 8.

In another example, artifact monitor 122 and, more particularly, artifact removal module 160, may be configured to substantially remove the signal artifact caused by the delivery of stimulation by INS 26 from the sensed electrical signal. In such an example, artifact monitor 122 (artifact removal module 160) may process a voltage signal between two or more of electrodes 50-55, 68, 72, 74, and 76 by applying a filter. The filter may be designed based on a predetermined signature used by INS 26 to generate a stimulation signal. Alternatively, the filter may be designed with a predetermined center frequency that is used by INS 26 to generate a stimulation signal. A more detailed description of artifact monitor 122 (artifact removal module 160) configured for substantially removing crosstalk is provided with respect to FIG. 9.

Artifact monitor 122 may preprocess the voltage signal and output the processed signal to cardiac sensing module 124. In this way, cardiac sensing module 124 may apply signal processing techniques known in the art to monitor the activity of heart 14, such as the amplification techniques described below for sensing R-waves and P-waves of electrical cardiac signals. Sensing module 116 may include a switch module to select which of the available electrodes are used to sense the electrical cardiac activity. In some examples, processor 110 may select the electrodes that function as sense electrodes via the switch module within sensing module 116, e.g., by providing signals via a data/address bus. In some examples, sensing module 116 may include one or more sensing channels, each of which may comprise an amplifier. In response to the signals from processor 110, the switch module within sensing module 116 may couple the outputs from the selected electrodes to one of the sensing channels.

In some examples, one channel of cardiac sensing module 124 may include an R-wave amplifier that receives signals from electrodes 50 and 51, which are used for pacing and sensing in right ventricle 32 of heart 14. Another channel may include another R-wave amplifier that receives signals from electrodes 52 and 53, which are used for pacing and sensing proximate to left ventricle 36 of heart 14. In some examples, the R-wave amplifiers may take the form of an automatic gain controlled amplifier that provides an adjustable sensing threshold as a function of the measured R-wave amplitude of the heart rhythm.

In addition, in some examples, one channel of cardiac sensing module 124 may include a P-wave amplifier that receives signals from electrodes 54 and 55, which are used for pacing and sensing in right atrium 30 of heart 14. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of cardiac sensing module 124 may be selectively coupled to housing electrode 68, or elongated electrodes 72, 74, or 76, with or instead of one or more of electrodes 50-55, e.g., for unipolar sensing of R-waves or P-waves in any of chambers 30, 32 or 36 of heart 14.

In some examples, cardiac sensing module 124 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 112 as an electrogram (EGM). In some examples, the storage of such EGMs in memory 112 may be under the control of a direct memory access circuit. Processor 110 may employ digital signal analysis techniques to characterize the digitized signals stored in memory 112 to detect and classify the patient's heart rhythm from the electrical signals. Processor 110 may detect and classify the heart rhythm of patient 12 by employing any of the numerous signal processing methodologies known in the art.

If ICD 16 is configured to generate and deliver pacing pulses to heart 14, processor 110 may include pacer timing and control module, which may be embodied as hardware, firmware, software, or any combination thereof. The pacer timing and control module may comprise a dedicated hardware circuit, such as an ASIC, separate from other processor 110 components, such as a microprocessor, or a software module executed by a component of processor 110, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided. When "D" is used with the third letter in the code, it may indicate that the signal is used for tracking purposes.

Intervals defined by the pacer timing and control module within processor 110 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals to cardiac sensing module 124 to blank one or more channels, e.g., amplifiers, for a period during and after delivery of electrical stimulation to heart 14. The durations of these intervals may be determined by processor 110 in response to stored data in memory 112. The pacer timing and control module of processor 110 may also determine the amplitude of the cardiac pacing pulses.

In an example in which ICD 16 is configured to retrieve information that has been encoded in a stimulation signal output (e.g., delivered to tissue) by INS 26, ICD 16 may modify its operation based on the retrieved information. For example, artifact monitor 122 may decode a sensed electrical signal in order to determine whether the blanking period of sensing module 116 should be modified. Thus, information that may be extracted from the sensed stimulation signal may include information that specifies the timing of therapy delivered by INS 26. Processor 110 may use the retrieved information to define a blanking period and provide signals to cardiac sensing module 124 to blank one or more channels during stimulation delivered by INS 26 and for a period following the therapy.

During pacing, escape interval counters within the pacer timing/control module of processor 110 may be reset upon sensing of R-waves and P-waves. Stimulation generator 114 may include pacer output circuits that are coupled, e.g., selectively by a switching module, to any combination of electrodes 50-55, 68, 72, 74, and 76 appropriate for delivery of a bipolar or unipolar pacing pulse to one of the chambers of heart 14. Processor 110 may reset the escape interval counters upon the generation of pacing pulses by stimulation generator 114, and thereby control the basic timing of cardiac pacing functions, including anti-tachyarrhythmia pacing.

The value of the count present in the escape interval counters when reset by sensed R-waves and P-waves may be used by processor 110 to measure the durations of R-R intervals, P-P intervals, P-R intervals and R-P intervals, which are measurements that may be stored in memory 112. Processor 110 may use the count in the interval counters to detect a tachyarrhythmia event, such as ventricular fibrillation event or ventricular tachycardia event. Upon detecting a threshold number of tachyarrhythmia events, processor 110 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, processor 110 may not meet the requirements for triggering a therapeutic response, and, thus, processor 110 may continue normal operation.

In some examples, processor 110 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 110 and any updating of the values or intervals controlled by the pacer timing and control module of processor 110 may take place following such interrupts. A portion of memory 112 may be configured as a plurality of recirculating buffers, capable of holding series of measured intervals, which may be analyzed by processor 110 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 110 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND GREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 110 in other examples.

In the examples described herein, processor 110 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 112 of ICD 16. In addition, the number of tachyarrhythmia events that are detected to confirm the presence of a tachyarrhythmia episode may be stored as a number of intervals to detect (NID) threshold value in memory 112. In some examples, processor 110 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 110 may determine that the tachyarrhythmia is present.

If processor 110 detects an atrial or ventricular tachyarrhythmia based on signals from sensing module 116, and an anti-tachyarrhythmia pacing regimen is desired, timing intervals for controlling the generation of anti-tachyarrhythmia pacing therapies by stimulation generator 114 may be loaded by processor 110 into the pacer timing and control module to control the operation of the escape interval counters therein and to define refractory periods during which detection of R-waves and P-waves is ineffective to restart the escape interval counters.

If ICD 16 is configured to generate and deliver defibrillation pulses to heart 14, stimulation generator 114 may include a high voltage charge circuit and a high voltage output circuit. In the event that generation of a cardioversion or defibrillation pulse is required, processor 110 may employ the escape interval counter to control timing of such cardioversion and defibrillation pulses, as well as associated refractory periods. In response to the detection of atrial or ventricular fibrillation or tachyarrhythmia requiring a cardioversion pulse, processor 110 may activate a cardioversion/defibrillation control module, which may, like pacer timing and control module, be a hardware component of processor 110 and/or a firmware or software module executed by one or more hardware components of processor 110. The cardioversion/defibrillation control module may initiate charging of the high voltage capacitors of the high voltage charge circuit of stimulation generator 94 under control of a high voltage charging control line.

Processor 110 may monitor the voltage on the high voltage capacitor, e.g., via a voltage charging and potential (VCAP) line. In response to the voltage on the high voltage capacitor reaching a predetermined value set by processor 110, processor 110 may generate a logic signal that terminates charging. Thereafter, timing of the delivery of the defibrillation or cardioversion pulse by stimulation generator 114 is controlled by the cardioversion/defibrillation control module of processor 110. Following delivery of the fibrillation or tachycardia therapy, processor 110 may return stimulation generator 114 to a cardiac pacing function and await the next successive interrupt due to pacing or the occurrence of a sensed atrial or ventricular depolarization.

Stimulation generator 114 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of stimulation generator 114.

Telemetry module 118 includes any suitable hardware, firmware, software or any combination thereof for communicating with another device, such as programmer 24 (FIG. 1). Under the control of processor 110, telemetry module 118 may receive downlink telemetry from and send uplink telemetry to programmer 24 with the aid of antenna 119. Antenna 119 may be similar to antenna 87 coupled to telemetry module 86 (FIG. 6). For example, antenna 119 may be internal or external to the housing of ICD 16. Processor 110 may provide the data to be uplinked to programmer 24 and the control signals for the telemetry circuit within telemetry module 98, e.g., via an address/data bus. In some examples, telemetry module 118 may provide received data to processor 110 via a multiplexer.

In some examples, processor 110 may transmit atrial and ventricular heart signals (e.g., EGM signals) produced by atrial and ventricular sense amp circuits within cardiac sensing module 124 to programmer 24. Programmer 24 may interrogate ICD 16 to receive the heart signals. Processor 110 may store heart signals within memory 112, and retrieve stored heart signals from memory 112. Processor 110 may also generate and store marker codes indicative of different cardiac episodes that cardiac sensing module 124 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of ICD 16 are coupled to power source 120, which may include a rechargeable or non-rechargeable battery. A non-rechargeable battery may be selected to last for several years, while a rechargeable battery may be inductively charged from an external device, e.g., on a daily or weekly basis.

The configuration of the functional blocks in FIG. 7 is merely one example. Other configurations are contemplated. For example, although FIG. 7 illustrates artifact monitor 122 and cardiac sensing module 124 are being part of sensing module 116, in other examples, processor 110 may include artifact monitor 122 and cardiac sensing module 124.

Figure 8:
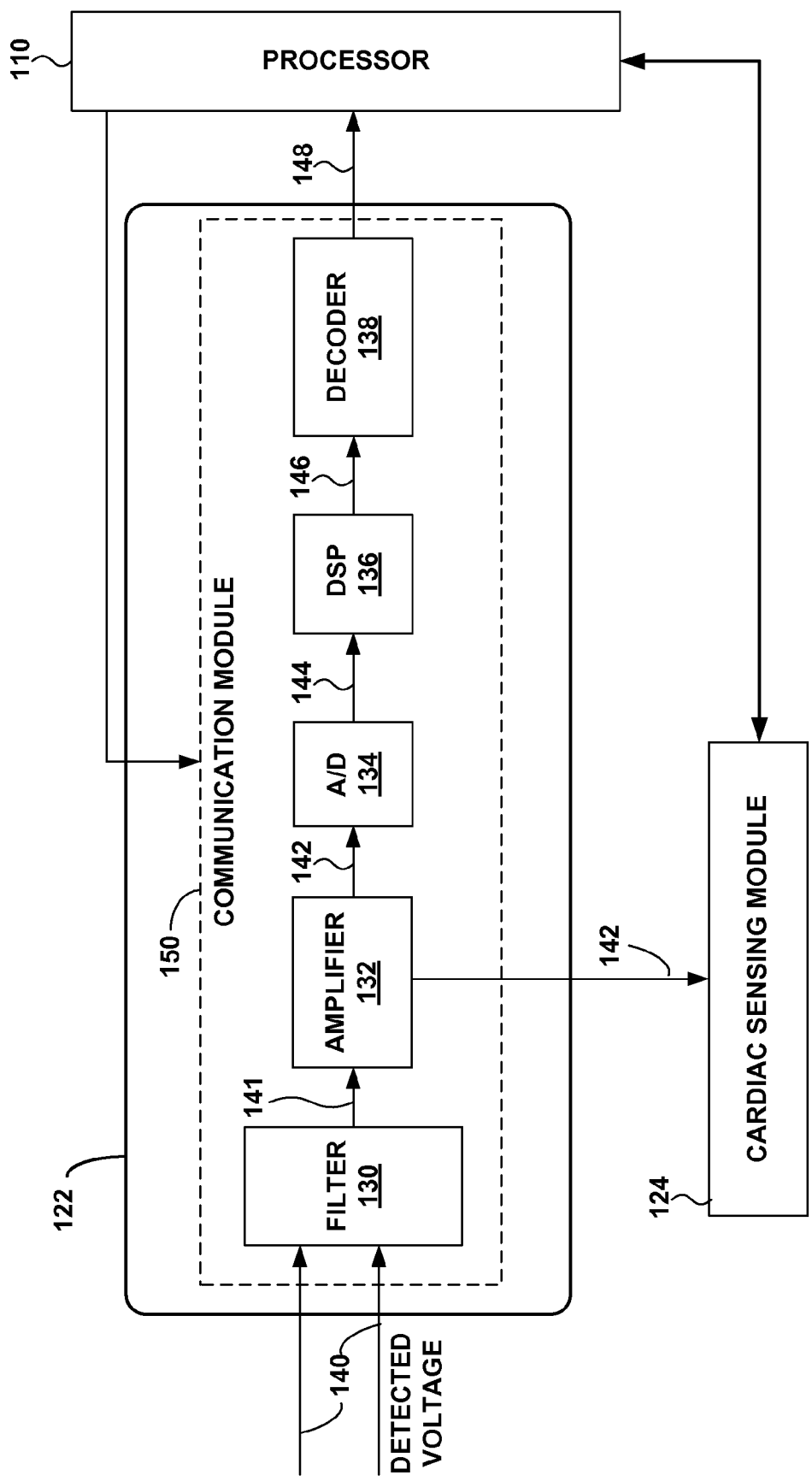
FIG. 8 is a functional block diagram illustrating an example configuration of the artifact monitor of an ICD.

FIG. 8 is a functional block diagram of an example configuration of artifact monitor 122 and illustrates communication module 150 in greater detail. As shown in the illustrated example of FIG. 8, communicate module 150 may include filter 130, amplifier 132, analog to digital converter (A/D) 134, DSP 136, and decoder 138. As previously described, INS 26 may encode information in a stimulation signal that provides therapeutic effects. The stimulation signal or, more specifically, a signal artifact of the stimulation signal, may be transmitted to ICD 16 by electrical conduction through tissue of patient 12.

In the illustrated example of FIG. 8, communication module 150 senses electrical activity within patient 12 by sensing a voltage 140, i.e., a voltage difference, across two or more of electrodes 50-55, 68, 70, 72, and 76 (FIG. 3) coupled to sensing module 116 of ICD 16. In particular, voltage 140 is sensed across inputs to filter 130. Voltage 140 may comprise signal components from one or more of a signal artifact resulting from a stimulation signal output by INS 26 and electrical activity of heart 14. Filter 130 may remove high frequency signals from the sensed wideband signal and output a narrowband filtered signal, i.e., signal 141. As an example, filter 130 may have a pass band of approximately 2.5 Hz to approximately 100 Hz.

Amplifier 132 amplifies filtered signal 141 to produce amplified signal 142 as an input to A/D 134. Amplified signal 142 may also be supplied to cardiac sensing module 124, which may process amplified signal 142 in accordance with the description provided in FIG. 7. For example, cardiac sensing module 124 may amplify signal 142, which may help processor 110 identify R-waves and P-waves of electrical cardiac signals.

A/D 134 may convert amplified signal 142 to a digital signal 144 for processing by DSP 136.

DSP 136 may be configured to employ various techniques for retrieving the information encoded in digital signal 144. In particular, DSP 136 may include hardware and/or software for measuring the pulse rate (frequency), pulse width (duration), phase, and duty cycle of digital signal 144. DSP 136 may output a signal 146 based on the measurement. For example, DSP 136 may employ peak detection techniques to determine a pattern in the pulse rate, pulse width or duty cycle of the stimulation signal generated by INS 26 in order to retrieve the encoded information. Additionally or alternatively, DSP 136 may be configured to operate as a matched filter. When INS 26 encodes information in the stimulation signal, INS 26 may prepend the information with a predetermined header. DSP 136 may be configured as a correlator for locating the header in digital signal 144. After locating the header, DSP 136 may apply additional processing, such as peak detection or other signal processing techniques, to retrieve the encoded information that may follow the header.

The output of DSP 136 is a processed digital signal 146 that represents the encoded information. Decoder 138 may analyze the series of digital values that form digital signal 146 in order to retrieve the encoded information. For example, each digital value may correspond to a particular signal characteristic, such as an amplitude value or a frequency value. Decoder 138 may output electrical signal 148 based on the retrieved information. Electrical signal 148 may be a control signal that conveys the encoded information to processor 110. For example, decoder 138 may be capable of outputting a number of predefined electrical signals that are associated with corresponding information in memory 112 (FIG. 7) of ICD 16. The predefined electrical signals may correspond to alphanumeric identifier or another type of symbolic identifier. Decoder 138 may match the digital values provided by DSP 136 to one or more corresponding identifiers and output electrical signal 148 accordingly.

Processor 110 may modify operation of ICD 16 based on electrical signal 148. For example, processor 110 may reference stored instructions within memory 112 to determine the instructions that are associated with electrical signal 148 from decoder 138. As previously indicated, memory 112 of ICD 16 may store a plurality of alphanumeric identifiers and associated instructions. The instructions may, for example, cause processor 110 to blank sensing circuitry, e.g., sensing module 116, at specified times. In this way, the specified times may be ultimately conveyed from INS 26 to ICD 16 by electrical signal 140.

As shown in FIG. 8, processor 110 may also provide control signals to communication module 150. For example, processor 110 may activate and deactivate communication module 150. Processor 110 may deactivate communication module 150 when INS 26 is not actively delivering therapy to patient 12 (e.g., when the delivery of stimulation by INS 26 is suspended). Processor 110 may determine when INS 26 delivers therapy based on information received from communication module 150. If communication module 150 is deactivated, processor 110 may periodically and temporarily reactivate communication module 150 to determine whether INS 26 has started to deliver therapy again. If communication module 150 determines that INS 26 is not delivering therapy, then processor 110 may deactivate communication module 150 for a given period of time. In this way, one-way communication between INS 26 and ICD 16 may be performed in an energy efficient manner.

Other configurations of communication module 150 are contemplated. For example, in other examples, communication module 150 may not include at least one of the components 130, 132, 134, 136, 138 or a single component may provide the functions attributed to the separate components 130, 132, 134, 136, 138 shown in FIG. 8. It should be understood that the modules shown illustrated in FIG. 8 illustrate logical functions and, thus, certain features of the modules may be provided by shared or common circuitry. For example, decoder 138 may share at least some circuitry with processor 110. Moreover, the order of the components 130, 132, 134, 136, 138 of communication module 150 shown in FIG. 8 is merely one example. For example, in other examples, amplifier 132 may amplify a signal prior to filtering by filter 130.

Figure 9:
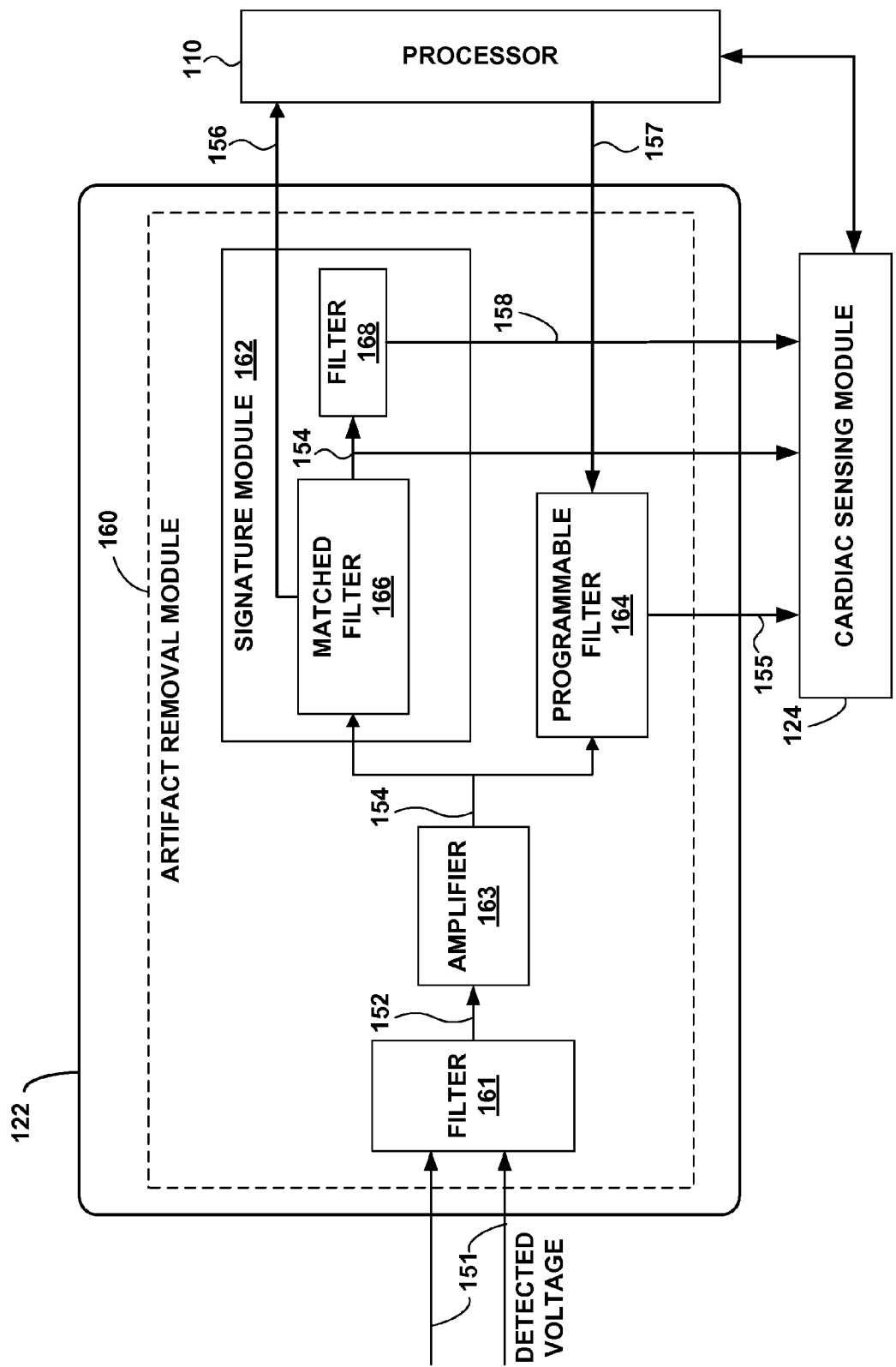
FIG. 9 is a functional block diagram illustrating another example configuration of the artifact monitor of an ICD.

FIG. 9 is a functional block diagram of an example configuration of artifact monitor 122 that shows artifact removal module 160 in greater detail. As shown in FIG. 9, artifact removal module 160 may include signature module 162 and programmable filter 164 for removing the signal artifact from a sensed electrical signal. In particular, signature module 162 may detect and remove a signal artifact having a predetermined signature from the sensed signal, and programmable filter 154 may remove a signal artifact with a narrowband energy spectrum centered at a predetermined frequency from the sensed signal. Although artifact removal module 160 is shown in FIG. 9 as including both signature module 162 and programmable filter 164, artifact removal module 160 may generally include one or both of signature module 162 and programmable filter 164. Artifact removal module 160 may include signature module 162 in examples in which INS 26 is configured to generate a stimulation signal with a predetermined signature. Artifact removal module 160 may include programmable filter 164 in examples in which INS 26 is configured to generate a stimulation signal with a narrowband energy spectrum centered at a predetermined frequency.

Just as with communication module 150 in FIG. 8, artifact removal module 160 may sense a voltage 151, i.e., a voltage difference across two or more of electrodes 50-55, 68, 70, 72, and 76 (FIG. 4). Again, voltage 151 may include a signal artifact of the stimulation signal output by INS 26 and electrical cardiac signals. Voltage 151 is sensed across inputs to filter 161, which may remove high frequency signals. Thus, filter 161 may filter the electrical signal generated by voltage 151 at its inputs to output a narrowband signal 152 to amplifier 163. In some examples, filter 161 may have a passband of approximately 2.5 Hz to approximately 100 Hz, although other frequency ranges are contemplated. Amplifier 163 amplifies narrowband signal 152 to produce amplified signal 154. Filter 161 and amplifier 163 in FIG. 9 may be substantially similar to filter 130 and amplifier 132 in FIG. 8. Filters 161, 130 and amplifiers 163, 132 may generally used to condition a sensed signal for processing by additional circuitry. Accordingly, amplified signal 154 is provided as an input to both signature module 162 and programmable filter 164.

In FIG. 9, signature module 162 includes matched filter 166 and filter 168. In general, matched filter 166 may be used to detect a predetermined signature in amplified signal 154 and filter 168 may be used to remove the predetermined signature from amplified signal 154. As shown in FIG. 9, matched filter 166 outputs control signal 156 to processor 110. Control signal 156 may be a logic signal that is high when the predetermined signature is detected and is low when the predetermined signature is not detected. Matched filter 166 also outputs amplified signal 154 to filter 168 and cardiac sensing module 124. In particular, matched filter may output amplified signal 154 to filter 168 when the predetermined signature is detected and output amplified signal 154 to cardiac sensing module 124 when the predetermined signature is not detected. When the predetermined signature is detected, filter 168 filters amplified signal 154 to substantially remove the predetermined signature, i.e., the signal artifact, from the signal. The filtered signal 158 is output to cardiac sensing module 124 to monitor the heart rhythm of patient 12. However, when matched filter 166 does not detect the predetermined signature, amplified signal 154 is output directly to cardiac sensing module 124 because a signal artifact is determined not to be present in the sensed signal.

Matched filter 166 may be implemented as an analog matched filter or a digital matched filter. When implemented as a digital matched filter, signature module 162 may also include an A/D to convert analog signal 154 to a digital signal suitable for input to the digital matched filter. In other examples, signature module 162 may be implemented using other components for analyzing amplified signal 154 for a predetermined signature.

In an example in which INS 26 is configured to generate a stimulation signal with a narrowband energy spectrum, amplifier 163 applies amplified signal 154 to programmable filter 164. Programmable filter 164 may be an analog or digital filter that passes frequencies outside of a stop band centered at a center frequency, e.g., a notch filter. Thus, programmable filter 164 may substantially remove a signal artifact with a narrowband energy spectrum centered at the predetermined frequency from amplified signal 154. Thus, programmable filter 164 outputs signal 155 to cardiac sensing module 124, and cardiac sensing module 124 may reliably process filtered signal 155 to monitor the heart of patient 12 while INS 26 delivers neurostimulation to patient 12.

In particular, programmable filter 164 may have a variable center frequency that is controlled by processor 110 via control signal 157. Processor 110 may select the center frequency of programmable filter 164 based on pre-programmed information or based on information received from INS 26. INS 26 may transmit the information to ICD 16 via RF communication or via stimulation signals output by INS 26 in as described in this disclosure. When the center frequency is a pre-selected parameter, programmable filter 164 need not be programmable and, thus, may be implemented as a filter with a fixed center frequency. In a similar manner, processor 110 may also use control signal 157 to control the bandwidth of programmable filter 164, i.e., the range of frequency for the stop band.

Figure 10:
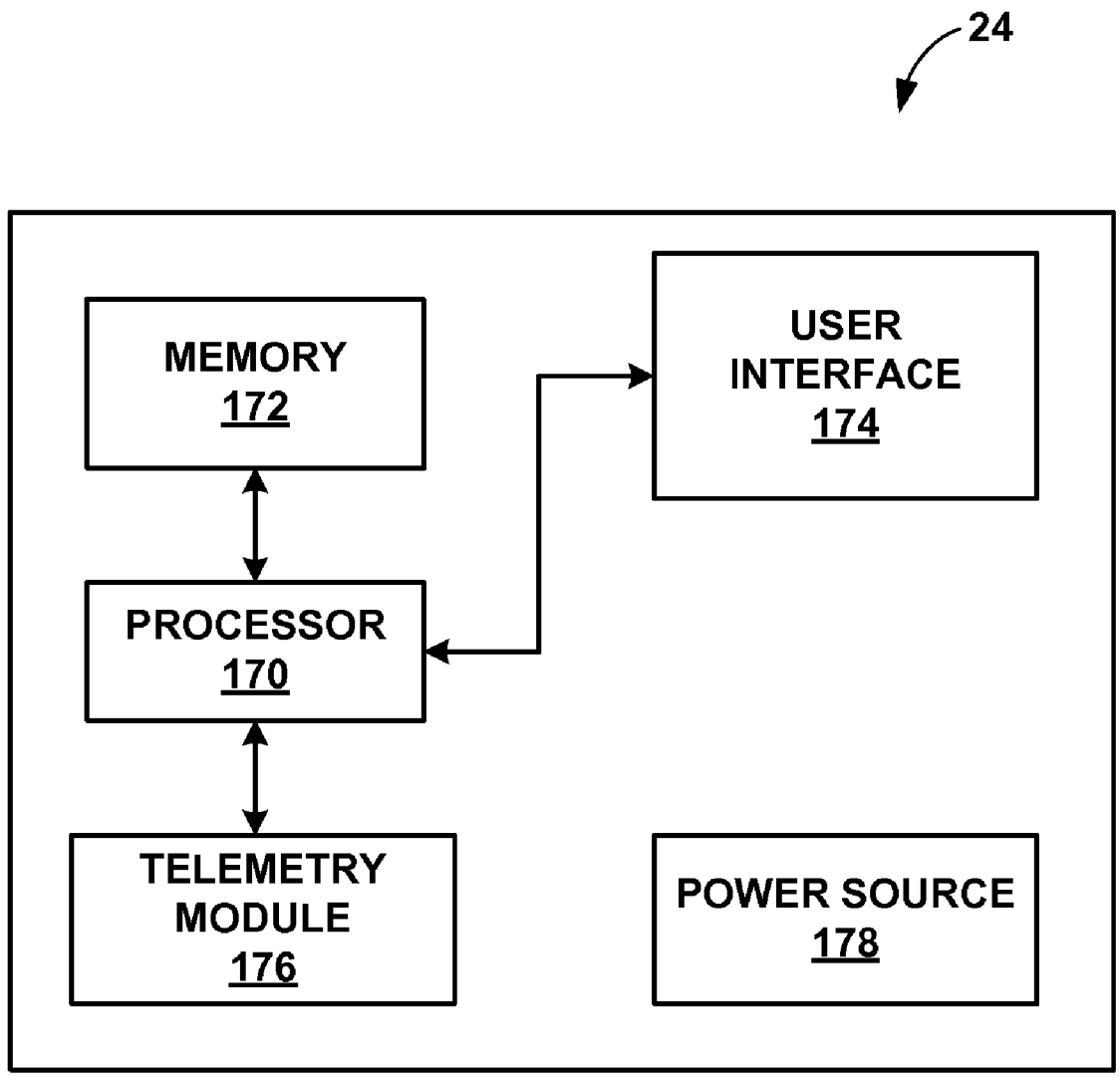
FIG. 10 is a functional block diagram illustrating an example external programmer.

FIG. 10 is block diagram of an example programmer 24. As shown in FIG. 10, programmer 24 includes processor 170, memory 172, user interface 174, telemetry module 176, and power source 178. Programmer 24 may be a dedicated hardware device with dedicated software for programming of ICD 16 and INS 26. Alternatively, programmer 24 may be an off-the-shelf computing device running an application that enables programmer 24 to program ICD 16 and INS 26. In some examples, separate programmers may be used to program ICD 16 and INS 26. However, a common programmer 24 that is configured to program both ICD 16 and INS 26 may provide a more streamlined programming process for a user, such as a clinician or patient 12.

A user may use programmer 24 to select therapy programs (e.g., sets of stimulation parameters), generate new therapy programs, modify therapy programs through individual or global adjustments or transmit the new programs to a medical device, such as ICD 16 or INS 26 (FIG. 1). The clinician may interact with programmer 24 via user interface 174, which may include display to present graphical user interface to a user, and a keypad or another mechanism for receiving input from a user.

Processor 170 can take the form one or more microprocessors, DSPs, ASICs, FPGAs, programmable logic circuitry, or the like, and the functions attributed to processor 102 herein may be embodied as hardware, firmware, software or any combination thereof. Memory 172 may store instructions that cause processor 170 to provide the functionality ascribed to programmer 24 herein, and information used by processor 170 to provide the functionality ascribed to programmer 24 herein. Memory 172 may include any fixed or removable magnetic, optical, or electrical media, such as RAM, ROM, CD-ROM, hard or floppy magnetic disks, EEPROM, or the like. Memory 172 may also include a removable memory portion that may be used to provide memory updates or increases in memory capacities. A removable memory may also allow patient data to be easily transferred to another computing device, or to be removed before programmer 24 is used to program therapy for another patient. Memory 172 may also store information that controls therapy delivery by ICD 16 and INS 26, such as stimulation parameter values.

Programmer 24 may communicate wirelessly with ICD 16 and INS 24, such as using RF communication or proximal inductive interaction. This wireless communication is possible through the use of telemetry module 176, which may be coupled to an internal antenna or an external antenna. An external antenna that is coupled to programmer 24 may correspond to the programming head that may be placed over heart 14, as described above with reference to FIG. 1. Telemetry module 176 may be similar to telemetry module 98 of ICD 16 (FIG. 6) or telemetry module 118 of INS 26 (FIG. 7).

Telemetry module 176 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 178 delivers operating power to the components of programmer 24. Power source 178 may include a battery and a power generation circuit to produce the operating power. In some examples, the battery may be rechargeable to allow extended operation. Recharging may be accomplished by electrically coupling power source 178 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 178 may include circuitry to monitor power remaining within a battery. In this manner, user interface 174 may provide a current battery level indicator or low battery level indicator when the battery needs to be replaced or recharged. In some cases, power source 178 may be capable of estimating the remaining time of operation using the current battery.

Figure 11A:
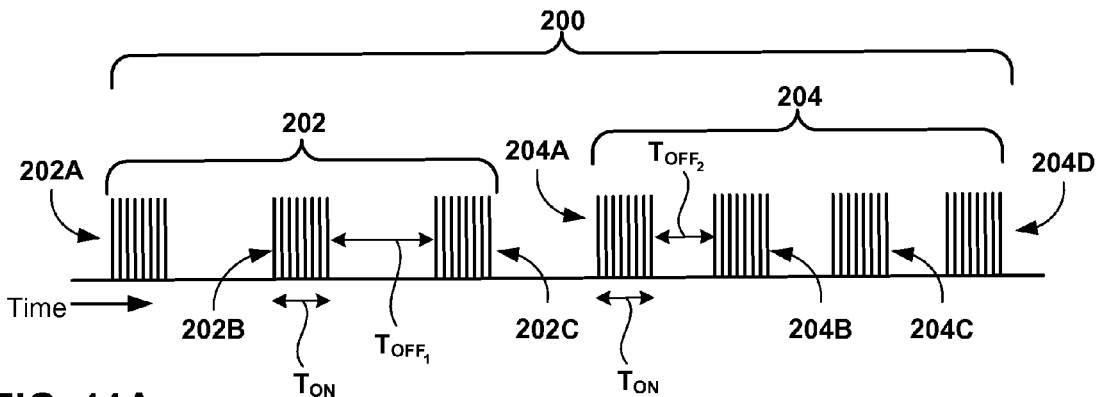
FIGS. 11A-11D illustrate example stimulation waveforms for communication between the INS and the ICD.

FIGS. 11A-11D illustrate example waveforms that stimulation generator 88 of INS 26 (FIG. 6) may generate and deliver to a tissue site within patient 12 in order to provide therapeutic benefits to patient 12. The example waveforms shown in FIGS. 11A-11D are encoded with information. In particular, FIGS. 11A-11D illustrate example pulse waveforms that may be generated by INS 26 and encoded with information by varying one or more signal parameters, e.g., pulse rate (frequency), pulse width (duration), phase, and duty cycle. It should be understood that the pulse waveforms illustrated in FIGS. 11A-1D are merely exemplary and should not be considered limiting of the disclosure. Rather, the purpose of pulse waveforms in FIGS. 11A-11D is to show various examples for encoding information by varying one or more signal parameter values.

As shown in FIGS. 11A-11D, INS 26 may generate a stimulation signal as a series of bursts of pulses, where each burst of pulses includes a plurality of pulses. The number of pulses for each burst of pulses may be a predefined parameter for a selected therapy program, which may be stored in memory 82 of INS 26 (FIG. 6). As previously described, INS 26 may generate the waveforms shown in FIGS. 11A-11D in accordance with one or more selected therapy programs and may encode information in the stimulation signal by varying the values one or more of the signal parameters, e.g., pulse rate (frequency), pulse width (duration), phase, and duty cycle, in a predetermined manner. ICD 16 extract the information from the stimulation signals shown in FIGS. 11A-11D based on the pattern with which the stimulation parameters are varied. For example, INS 26 and ICD 16 may share a set of instructions that associate different patterns in stimulation signal parameter values with certain types of information (e.g., instructions relating to the modification to the sensing parameters of ICD 16).

Figure 11B:
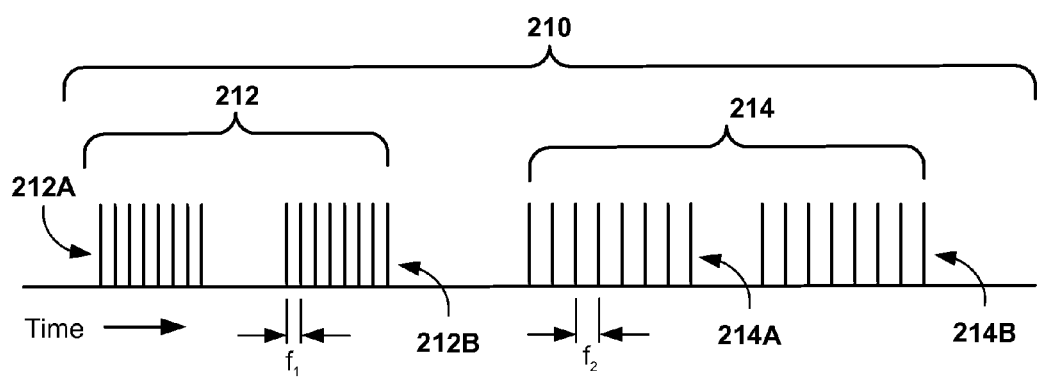
Figure 11C:
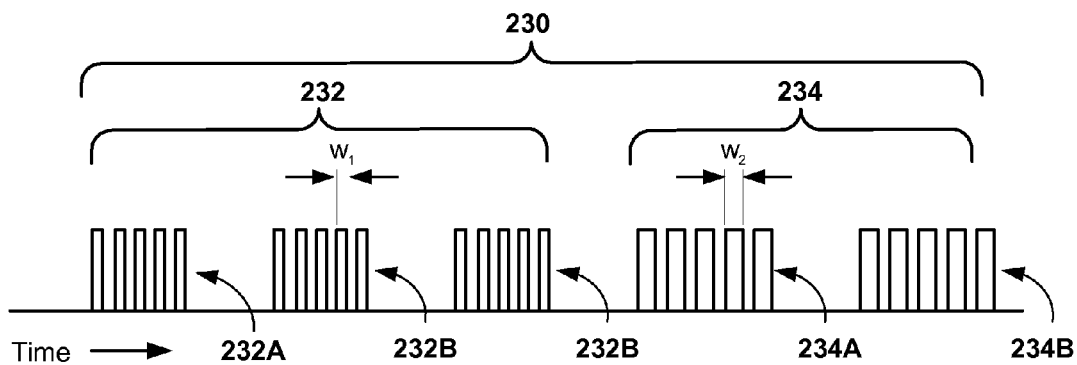

Information is encoded in the waveforms in FIGS. 11A-11C by varying one signal parameter on a burst-by-burst basis. In other examples, information may be encoded in the stimulation signals by varying more than one signal parameter at any given time. Each pulse for a particular burst in the waveforms in FIGS. 11A-11C is generated with the same signal parameter values, but the signal parameter values may vary between bursts. In this way, each burst or group of bursts may be associated with an alphanumeric identifier or another type of identifier. In examples in which the bursts or group of bursts are associated with alphanumeric identifiers, the burst or group of bursts may be may be arranged such that the associated alphanumeric identifiers to form alphanumeric code words that can be used to transmit messages to the receiving device, e.g., ICD 16. These messages may contain information regarding the therapy delivered by INS 26, such as the type of therapy and duration of a current therapy session. The current therapy session may be, for example, the therapy session in which INS 26 is delivering therapy to patient 12 when ICD 16 senses the stimulation signal artifact. The type of therapy may be encoded by specifying the selected therapy program(s) or by specifying the therapy parameter values. In addition, as previously indicated, the duration of therapy may be encoded by specifying a stop time, by specifying a start and a stop time, by specifying the total duration of time or by specifying the time remaining.

Figure 11D:
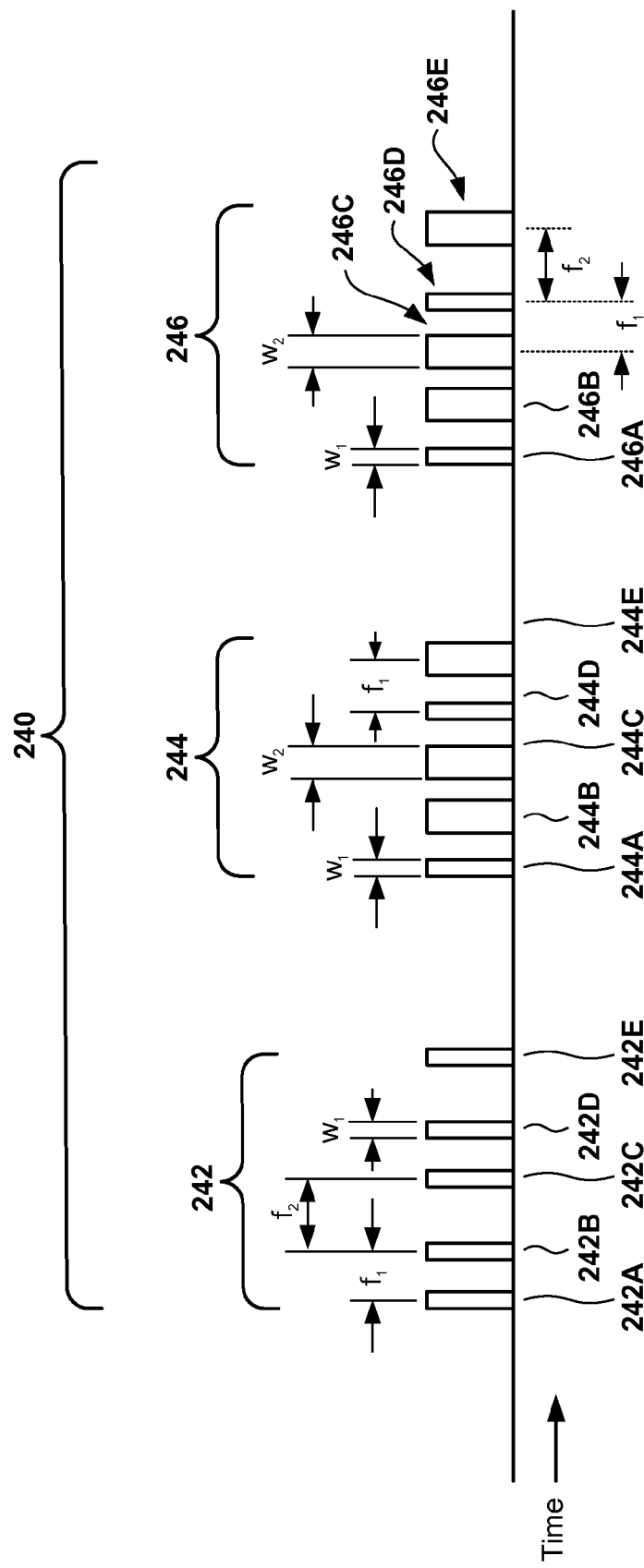

Information is encoded in the waveform in FIG. 11D by varying one or more signal parameters on a pulse-by-pulse basis. Thus, at least two pulses in a particular burst of pulses may be generated with different signal parameter values. This technique may also be used to encode information by associating each burst of pulses or group of bursts with a symbol from a predefined alphanumeric code. Alternatively, this method may also be used to encode information by associating each pulse with an alphanumeric identifier in order to provide a greater information transmission rate.

In general, the purpose of the waveforms shown in FIGS. 11A-11D is not to illustrate a stimulation waveform encoded with particular information. Instead, the purpose of the waveforms is to provide an example that shows how information may be encoded in a stimulation waveform by varying one or more signal parameters, such as duty cycle (FIG. 11A, frequency (FIG. 11B), pulse width (FIG. 11C), and frequency and pulse width (FIG. 11D).

With respect to FIG. 11A, stimulation generator 88 of INS 26 varies the duty cycle of pulse waveform 200 in order to transmit information to ICD 16. Waveform 200 includes bursts of pulses 202A-202C (collectively bursts of pulses "202" or "bursts 202") and 204A-204D (collectively "bursts of pulses 204" or "bursts 204"). Bursts of pulses 202 are delivered in accordance with a first duty cycle and bursts of pulses 204 are delivered in accordance with a second duty cycle that is different than the first duty cycle.

In FIG. 11A, $T_{ON}$ is the duration of time during which stimulation generator 88 delivers pulses of waveform 200, and $T_{OFF1}$ and $T_{OFF2}$ are the durations of times during which stimulation generator 88 is not delivering pulses. The duty cycle of bursts of pulses 202 and 204 may be the ratio of $T_{ON}$ to a total cycle time including $T_{ON}$ and $T_{OFF1}$ or $T_{OFF2}$, respectively. In the following description, $T_{ON}$ is a constant value so the total cycle time for is different for the first and second duty cycles, and the values for $T_{OFF1}$ and $T_{OFF2}$ are selected to encode information. However, in other examples, that first and second duty cycles may be selected by using a constant value for $T_{OFF}$ and using different values for $T_{ON}$. Additionally, it is contemplated that the total cycle time be a constant value and different $T_{ON}$ and $T_{OFF}$ values be selected for each of the different duty cycles used for encoding information.

In any case, with respect to FIG. 11A, the duty cycle of bursts 202 and 204 are generally selected to be different from each other and may be selected anywhere between 0% and 100% ON. In a 0% ON, $T_{ON}$ is substantially equal to zero, such that stimulation generator 88 does not deliver any pulses in the burst having the duty cycle of approximately 0% ON. In a 100% ON duty cycle, $T_{OFF}$ is substantially equal to zero, such that the burst of pulses is substantially one continuous pulse. In some examples, a duty cycle may typically be selected to be less than 50% ON and more than 50% OFF, such that the duration of times $T_{OFF1}$ or $T_{OFF2}$ between bursts 202, 204, respectively, is greater than the duration of each burst 202, 204. Accordingly, the duty cycle for bursts 202 and 204 may each be selected to be less than 50% ON, but with different values, such as 25% ON for bursts 202 and 50% ON for bursts 204. In a duty cycle of approximately 25% ON, $T_{ON}$ may be approximately one third the value of $T_{OFF1}$ or $T_{OFF2}$. In a duty cycle of approximately 50% ON, $T_{ON}$ may be approximately equal to the value of $T_{OFF1}$ or $T_{OFF2}$. As another example, the duty cycle for one of bursts 202 and 204 maybe selected to be more than 50% ON and the duty cycle for the other may be selected to be less than 50% ON.

Waveform 200 in FIG. 11A includes bursts 202 and bursts 204. More specifically, bursts 202 and 204 comprise bursts of pulses that each include the same number of pulses and in which the pulses are generated with substantially equal pulse rates (frequency) and pulse width (rate). The number, frequency, and pulse width for the pulses is merely exemplary and may be selected according to a particular therapy program, which may depend on the patient's condition or the desired therapeutic results. The duty cycle for bursts 202 and 204, however, is varied to encode information in waveform 200. In particular, bursts 202 are generated using a duty cycle defined as the ratio of $T_{ON}$ to $T_{OFF1}$, and bursts 204 are generated using a duty cycle defined as the ratio of $T_{ON}$ to $T_{OFF2}$.

In general, stimulation generator 88 encodes information in pulse waveform 200 by selectively generating the bursts of pulses using the different duty cycle values. For example, stimulation generator 88 may encode binary information, i.e., a sequence of "0" and "1" values that correspond to predefined therapy information, by selectively generating bursts of pulses using the different duty cycle values. In this example, the first duty cycle value may correspond to a "0" value and the second duty cycle value may correspond to a "1" value. In this way, each burst of pulses may be viewed as a digital bit and groups of bursts may be arranged to form digital words that correspond to predefined messages. Encoding information on a burst-by-burst basis may be referred to as "burst encoding."

In another example, stimulation generator may encode binary information by selectively generating groups of bursts using the different duty cycle values or combination of the duty cycle values. In this example, each burst of the group may be generated using the same duty cycle value, or bursts in the group may be generated using more than duty cycle value. If each group is generated using the same duty cycle value, the information rate decreases, but may allow for increased system performance, i.e., increased reliability because there may be a higher probability that ICD 16 will properly sense the stimulation artifact and decode the information encoded therein. Communication module 150 (FIG. 8) of ICD 16 may extract the pattern in the duty cycles from a sensed electrical signal and retrieve the information contained in an artifact signal.

FIG. 11B illustrates an example stimulation waveform 210 in which stimulation generator 88 may vary the frequency of pulses to encode information in a stimulation signal. In FIG. 11B, stimulation waveform 210 includes bursts of pulses 212A and 212B (collectively "bursts 212") and bursts of pulses 214A and 214B (collectively "bursts of pulses 214"). Stimulation generator 88 generates the pulses in bursts 212 with a frequency $f_1$ and the pulses in bursts 214 with frequency $f_2$. Generally, frequencies $f_1$ and $f_2$ may be predetermined values and selected to be different than one another. The value for frequency $f_1$ is selected to be smaller than the value for frequency $f_2$ in FIG. 11B. The predetermined frequencies may be selected within a range of approximately 10 Hz to approximately 100 Hz.

Stimulation generator 88 may encode information in pulse waveform 210 by selectively generating the bursts of pulses using the different frequencies. For example, stimulation generator 88 may encode binary information, i.e., a sequence of "0" and "1" values that correspond to predefined therapy information, by selectively generating bursts of pulses having different pulse frequencies. In this example, a burst having a first pulse frequency value may correspond to a "0" value and a burst having a second pulse frequency value may correspond to a "1" value. Communication module 150 (FIG. 8) of ICD 16 may extract the different pulse frequency values from a sensed electrical signal and retrieve the information contained in an artifact signal.

It may be important to select the pulse frequency for the bursts of pulses to minimize the possibility of different bursts of pulses from being confused with each other. For example, in some cases, it may be undesirable to select the frequency, $f_1$, for bursts 212 to be about 50 Hz and select the frequency, $f_2$ for bursts 214 to be about 100 Hz because undersensing every other pulse for bursts 214 may result in bursts 214 and burst 212 appearing the same. For this reason, it may be beneficial to select, for example, $f_1$ and $f_2$ as 50 Hz and 55 Hz, respectively.

FIG. 11C illustrates an example stimulation waveform 230 in which stimulation generator 88 may vary the pulse width to encode information in a stimulation signal. In FIG. 11C, stimulation waveform 230 includes bursts of pulses 232A-232C (collectively "bursts of pulses 232") and bursts of pulses 234A and 234B (collectively "bursts of pulses 234"). Stimulation generator 88 generates the pulses in bursts 232A-232C with a width $W_1$, and the pulses in bursts 234 with a width $W_2$. The pulse width or pulse duration may be selected within a range of approximately 30 μs to approximately 480 μs, although other pulse widths are contemplated and may depend upon the pulse widths that provide therapeutic stimulation therapy to patient 12. In the example shown in FIG. 11C, width $W_1$ is selected to be smaller than width $W_2$.

Just as with the other stimulation parameter value modulations, stimulation generator 88 may encode information in pulse waveform 230 by selectively generating the bursts of pulses having the different pulse widths. For example, stimulation generator 88 may encode binary information, i.e., a sequence of "0" and "1" values that correspond to predefined therapy information, by selectively generating bursts of pulses having different pulse widths. In this example, a burst having a first pulse width value may correspond to a "0" value and a burst having a second pulse width value may correspond to a "1" value. Communication module 150 (FIG. 8) of ICD 16 may extract the different pulse frequency values from a sensed electrical signal and retrieve the information contained in an artifact signal.

FIG. 11D illustrates an example pulse waveform 240 in which stimulation generator 88 may vary a signal parameter on a pulses-to-pulse basis to encode information in a stimulation signal. Moreover, stimulation generator 88 may encode information in pulse waveform 240 by varying the value of more than one type of signal parameter on a pulse-to-pulse basis. In FIG. 11D, stimulation waveform 240 includes bursts of pulses 242, 244, and 246. Burst 242 includes pulses 242A-242E. Burst 244 includes pulses 244A-244E. Burst 246 includes pulses 246A-246E. For each of bursts 242, 244, and 246, the value of at least one stimulation parameter is varied to encode information.

With respect to burst 242, pulses 242A-242E have substantially the same pulse width $W_1$, but are generated with varying frequency to encode information. In particular, pulses 242B, and 242D are generated with a frequency $f_1$ relative to respective pulses 242A and 242C, and pulses 242C and 242E are generated with a frequency $f_2$ relative to respective pulses 242B and 242D. With respect to burst 244, pulses 244B-244E have substantially the same frequency, $f_1$, but are generated to have different pulse widths. The pattern in the pulse widths may be modified in order to encode information in the stimulation waveform 240. In particular, pulses 243A and 243D have a pulse width $W_1$, and pulses 243B, 243C, and 243E have a pulse width $W_2$.

With respect to burst 246, the value of more than one type of signal parameter is varied to encode information in pulses 246A-246E. Pulse 246A and pulse 246D have a pulse width $W_1$ with pulse 246D having a frequency $f_1$. Pulses 246B and 246C have a frequency $f_1$ relative to respective pulses 246A and 246B, and a pulse width $W_2$, which is different than pulse width $W_1$. Pulse 246E has a frequency $f_2$ relative to pulse 246D, and pulse width $W_2$.

FIGS. 12A and 12B and FIGS. 13A and 13B illustrate example stimulation waveforms with a predetermined signature that may be generated by stimulation generator 88 (FIG. 6) of INS 26. Generally, the predetermined signature may be uniquely characterized by one or more of frequency content, duty cycle, and/or signal envelope. Because the signature is known by both INS 26 and ICD 16, ICD 16 may be configured to include signal processing components specifically configured to remove the stimulation signals generated by INS 26 from a sensed electrical signal. The processing components may include, for example, such as envelope detectors, correlators, and filters to substantially remove the corresponding signal artifact (crosstalk) from the sensed signal.

FIG. 12A illustrates an example stimulation waveform 300 that stimulation generator 88 may generate and deliver in order to reduce interference with the sensing of cardiac signals by ICD 16. Stimulation generator 88 may generate example stimulation waveform 300 including a plurality of pulses that follow a predetermined signal envelope 302. Signal envelope 302 traces the outline of example stimulation waveform 300 and is characterized by three substantially equal amplitudes and three substantially equal duration peaks. Stimulation generator 88 may generate stimulation waveform 300 by outputting bursts of pulses and alternating the amplitude of the pulses in successive bursts of pulses between two different values. With respect to FIG. 12A, each pulses in burst of pulses 304A, 304C, and 304E have a first amplitude value, and each pulse in bursts of pulses 304B, 304D, and 304F have a second amplitude value that is greater than the first amplitude value. As a result, signal envelope 302 may appear similar to a square wave.

FIG. 12B illustrates another example stimulation waveform 310 that stimulation generator 88 may generate and deliver to patient 12 in order to reduce interference with the sensing of cardiac signals by ICD 16. As shown in FIG. 12B, stimulation waveform 310 includes bursts of pulses 314A-314F (collectively "bursts of pulses 314"). Each of bursts of pulses 314 includes pulses that increase in amplitude and then decrease in amplitude over time to define a rising edge, falling edge, and peak. With respect to FIG. 12B, bursts 314A and 314B, 314C and 314D, and 314E and 314F form closely spaced pairs of amplitude peaks. Consequently, signal envelope 312 is characterized by closely spaced pairs of amplitude peaks where each pair of amplitude peaks are spaced from each other.

Figure 13A:
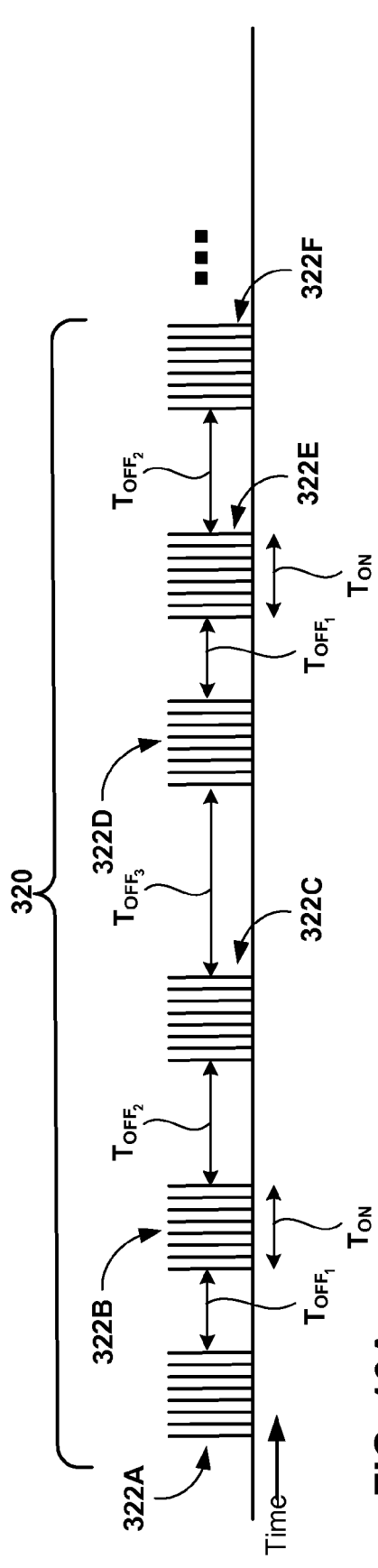
Figure 13B:
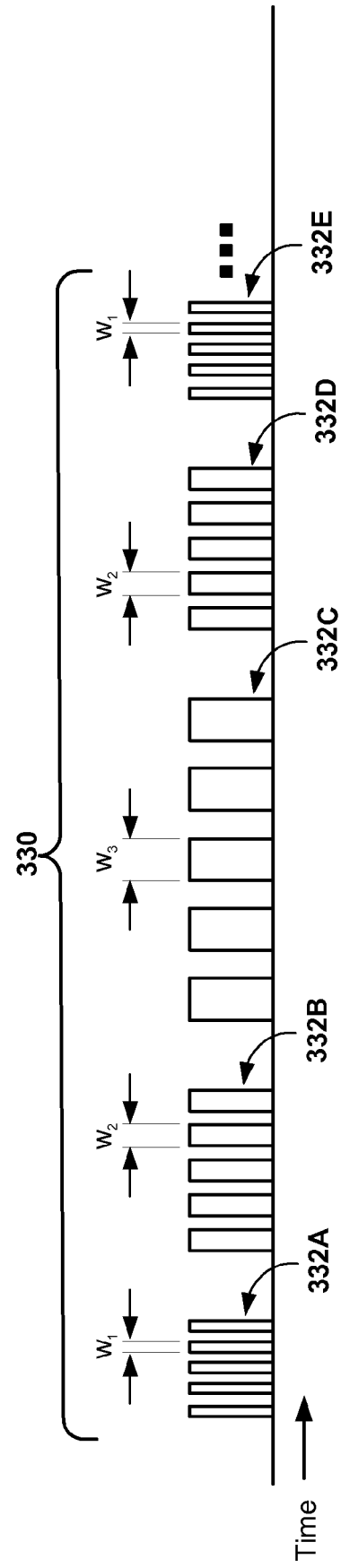

FIGS. 13A and 13B illustrate example stimulation waveforms that may be generated by INS 26 with a predetermined signature by varying values of one or more signal parameters. In particular, FIG. 13A illustrates an example stimulation waveform 320 with a predetermined signature for facilitating the removal of resulting crosstalk at ICD 16. Stimulation waveform 320 includes bursts of pulses 322A-322F (collectively "bursts of pulses 322") that each includes seven pulses of substantially equal amplitude and duration. The signature of waveform 320 is characterized by generating bursts 322 with progressively decreasing duty cycle values that reach a minimum value, and then repeat the progression from the initial maximum duty cycle value to the minimum duty cycle value.

In FIG. 13A, stimulation generator 88 (FIG. 6) of INS 26 generates waveform 320 with the predetermined signature by generating bursts 322 using three different duty cycle values, i.e., first, second, and third duty cycle values. The first, second, and third duty cycle values are defined as the ratio of $T_{ON}$ to $T_{OFF1}$, $T_{OFF2}$, and $T_{OFF3}$, respectively. The first, second, and third duty cycle values decrease in value over time. More specifically, INS 26 generates stimulation waveform 320 by generating burst 322A using the first duty cycle value, burst 322B using the second duty cycle value, and burst 322C using the third duty cycle value, where the first duty cycle value is larger than the second and third duty cycle values, and the second duty cycle value is larger than the third duty cycle value. INS 26 then repeats the pattern by generating bursts 322D-322F using the first, second, and third duty cycle values. In this way, INS 26 may generates stimulation waveform 320 with a signature characterized by a progressively descending duty cycle that reaches a minimum value and then repeats the descent from the initial maximum value to the minimum value.

The minimum duty cycle value may indicate, for example, the minimum duty cycle value that provides therapeutic efficacy to patient 12. Thus, although the duty cycles vary in stimulation waveform 320, the delivery of waveform 320 to tissue of patient 12 may provide efficacious therapy to patient 12, e.g., to provide cardiac benefits.

FIG. 13B illustrates another example stimulation waveform 330 that may be generated by INS 26 with a predetermined signature. In FIG. 13B, stimulation waveform 330 includes bursts of pulses 332A-323E (collectively "bursts of pulses 332") that each include five pulses. The signature of waveform 330 is characterized by bursts 332 that each include pulses having progressively increasing pulse width values followed by bursts including pulses having progressively decreasing pulse width values. The pulse width values may be varied between a maximum value and a minimum value, where the minimum and maximum pulse width values indicate the range of pulse width values that provide efficacious therapy to patient 12.

As shown in FIG. 13B, INS 26 generates each of bursts 332 using one of three different pulse width values, i.e., $W_1$, $W_2$, and $W_3$, in accordance with the predetermined signature or pattern. In particular, stimulation generator 88 may generate waveform 320 by generating burst 332A including pulses having a first pulse width value $W_1$, followed by burst 332B including pulses having a second pulse width value $W_2$, and followed by burst 332C including pulses having a third pulse width value $W_3$. Thereafter, stimulation generator 88 may generate bursts 332D and 332E using pulses having pulse width values $W_2$ and $W_1$, respectively.

In general, INS 26 may deliver therapy to patient 12 by continuously repeating waveforms 300, 310, 320, and 330 in FIGS. 12A, 12B, 13A, and 13B, respectively. By repeating the predetermined signature in this way, ICD 16 may not be required to be synchronized with INS 26. Rather, ICD 16 may continuously analyze a sensed signal and remove the signal artifact when the predetermined signature is detected.

In general, the waveforms shown in FIGS. 12A, 12B, 13A, and 13B are merely examples and should not be considered limiting of the disclosure as described herein. Rather, the purpose of FIGS. 12A, 12B, 13A, and 13B are to provide examples for using a predetermined signature to facilitate removal of a signal artifact by ICD 16. Other signatures that may be characterized by varying the values of one or more signal parameters are contemplated and, thus, within the scope of this description. It is recognized that the complexity of the signature may be restricted by the processing capabilities of ICD 16, and that a system designer may be responsible for balancing the tradeoff between performance and complexity. However, as processors utilized by ICD 16 improve, increasingly complex signal processing techniques may be used.

Figure 14A:
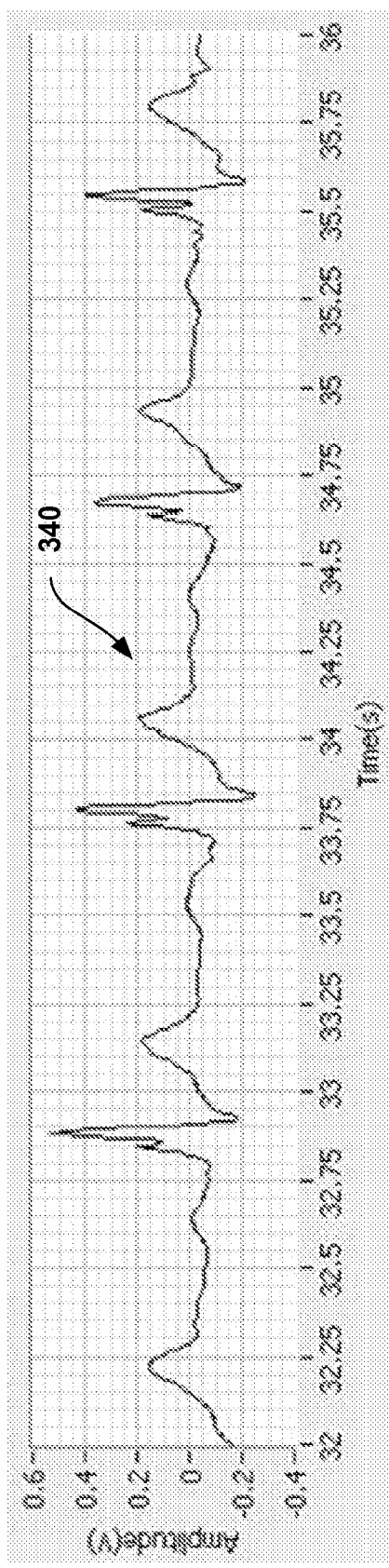
FIG. 14A illustrates an example EGM waveform generated by the ICD when the INS is not delivering therapy to the patient.
Figure 14B:
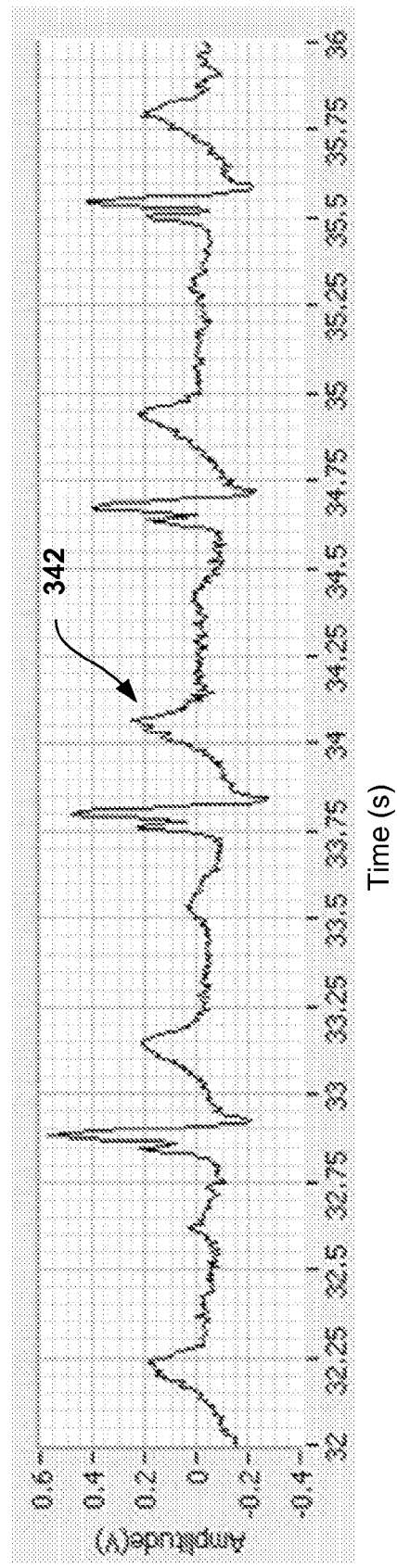
FIG. 14B illustrates an example EGM waveform generated by the ICD when the INS is configured to deliver therapy by generating stimulation signals that have a spread spectrum energy distribution.

FIGS. 14A and 14B illustrate example EGM waveforms that represent an electrical signal sensed by sensing module 116 (FIG. 7) of ICD 16 when INS 26 is configured to generate stimulation signals with a spread spectrum energy distribution. In particular, EGM waveform 340 in FIG. 14A may be generated by ICD 16 when INS 26 is not delivering therapy. Accordingly, EGM waveform 340 is substantially void of an artifact attributable to the stimulation delivery by INS 26. Waveform 340 is a relatively smooth signal.

FIG. 14B illustrates EGM waveform 342 indicative of an electrical signal sensed by sensing module 116 of by ICD 16 while INS 26 is delivering therapy to patient 12. Consequently, a stimulation artifact is present in EGM waveform 342. In the example shown in FIG. 14B, stimulation generator 88 (FIG. 6) of INS 26 is generating and delivering a stimulation signal having one or more randomly or pseudo-randomly varied signal parameters while sensing module 116 senses an electrical signal. The signal parameters may include, for example, a current amplitude, a voltage amplitude, a pulse width, duty cycle and/or a pulse rate.

In FIG. 14B, the stimulation artifact appears as wideband noise in ECG waveform 342 because the random or pseudo-random variation of the values of one or more signal parameters of the stimulation signal by INS 26 produces a spread spectrum energy distribution. Because the energy of the stimulation signal is spread substantially across the frequency spectrum, rather than concentrated in a relatively narrow frequency band, crosstalk between INS 26 and ICD 16 may be mitigated. In other words, the energy of the stimulation signal is spread out in such a way that the crosstalk does not adversely interfere with the electrical signal sensed by ICD 16 or the ability of ICD 16 to monitor cardiac events using the EGM waveform generated via the sensed electrical signal.

When INS 26 generates a stimulation signal with a spread spectrum energy distribution, ICD 16 may utilize techniques well known in the art for analyzing the ECG waveform and may not require additional processing to suppress the wideband noise. Alternatively, ICD 16 may use wideband filters or filtering techniques to substantially remove or mitigate the wideband noise. In some examples, a filter may be applied to a time domain signal. In other examples, ICD 16 may convert the received analog signal to a digital signal and use digital signal processing techniques, such as performing a frequency analysis and apply digital filters to the digital signal.

Figure 15:
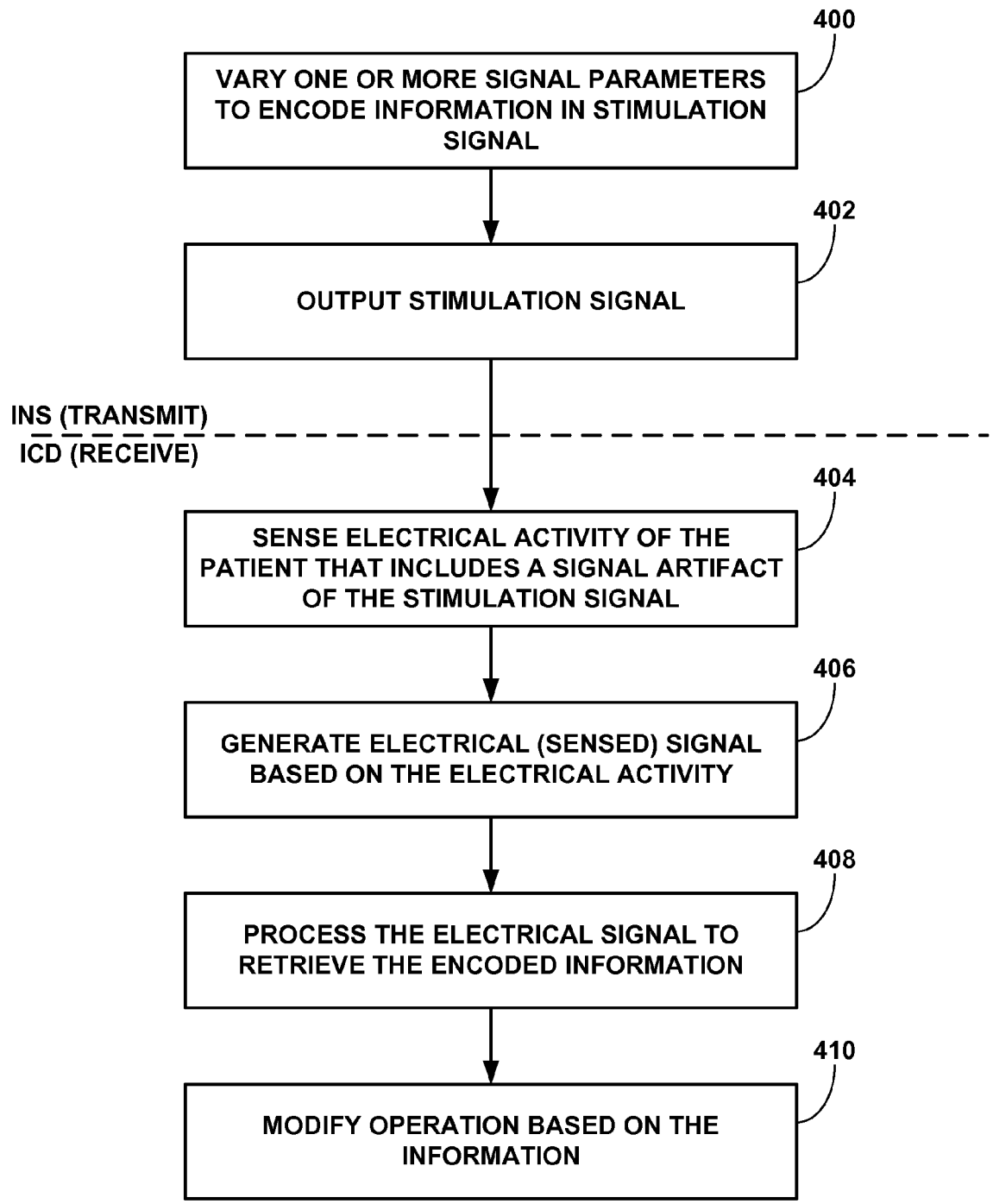
FIG. 15 is a flow diagram illustrating an example technique that either the INS or ICD may use to communicate with the ICD or INS, respectively.

FIG. 15 is a flow diagram of an example technique INS 26 and ICD 16 may implement in order to communicate. In the example method of FIG. 15, the communication is one-way from INS 26 to ICD 16. Stimulation generator 88 (FIG. 6) of INS 26 generates an electrical stimulation signal that provides therapeutic benefits to patient 12, and varies the value of one or more signal parameters of the stimulation signal in order to encode information in the stimulation signal (400). Processor 80 (FIG. 6) may load an initial set of signal parameter values (or stimulation parameter values) for generating the stimulation signal according to one or more selected therapy programs and encode information by varying one or more of the signal parameters defined by the one or more selected therapy programs. That is, the therapy programs may provide initial values for generating the stimulation signal, and processor 80 may control stimulation generator 88 to vary one or more of the signal parameters from the initial value to encode the information. The variation may be restricted to a predefined range from the initial value. The signal parameters may include, for example, a slew rate, pulse rate (frequency), pulse width (rate), voltage/current amplitude, phase, and duty cycle. As previously described, the encoded information may include therapy information, operational information, diagnostic information, and message information. For example, the encoded therapy information may include information regarding the type and duration of therapy by specifying one or more of the selected therapy program(s), the therapy parameters, a stop time for the therapy, a start time for the therapy, the duration of the therapy, or the remaining time that therapy will be delivered.

INS 26 outputs the stimulation signal (402) which may, at least partially, be coupled to ICD 16 by electrical conduction through tissue of patient 12. As previously described, the stimulation signal output by INS 26 may result in a signal artifact, i.e., crosstalk, in the electrical signal sensed by ICD 16.

ICD 16 senses electrical activity of patient 12 that includes the signal artifact of the stimulation signal (404) and generates an electrical signal based on the electrical activity (406). This electrical signal may be referred to as a sensed electrical signal because it is generated based on electrical activity sensed by ICD 16. As previously described with respect to FIGS. 7 and 8, ICD 16 may be configured to generate the sensed signal by sensing a voltage difference between two or more of electrodes 50-55, 68, 72, 74, and 76 (FIG. 4). ICD 16 is also configured to process the sensed signal to retrieve the encoded information (408). Sensing module 116 and/or processor 110 (FIG. 7) of ICD 16 may utilize various signal processing techniques well known in the art of telecommunications to retrieve the encoded information. For example, as described above with respect to FIGS. 7-9, ICD 16 may be configured to process the sensed signal with peak detectors, correlators, comparators, frequency analysis components, decoders, and other signal processing techniques.

Finally, ICD 16 may modify its operation based on the retrieved information (410). For example, if the retrieved information specifies the duration of the therapy, ICD 16 may suspend the delivery of cardiac rhythm therapy in order to prevent delivering unnecessary stimulation therapy to heart 14. In other examples, ICD 16 may blank sensing channels while INS 26 delivers therapy. This may effectively also prevent ICD 16 from delivering therapy to patient 12. In another example, ICD 16 may apply additional signal processing to remove the signal artifact from the sensed signal. In this way, ICD 16 may pre-process the sensed signal to retrieve information and substantially remove the signal artifact from the sensed signal before processing the sensed signal (that now has the signal artifact substantially removed) to monitor cardiac activity and detect an arrhythmia.

Figure 16:
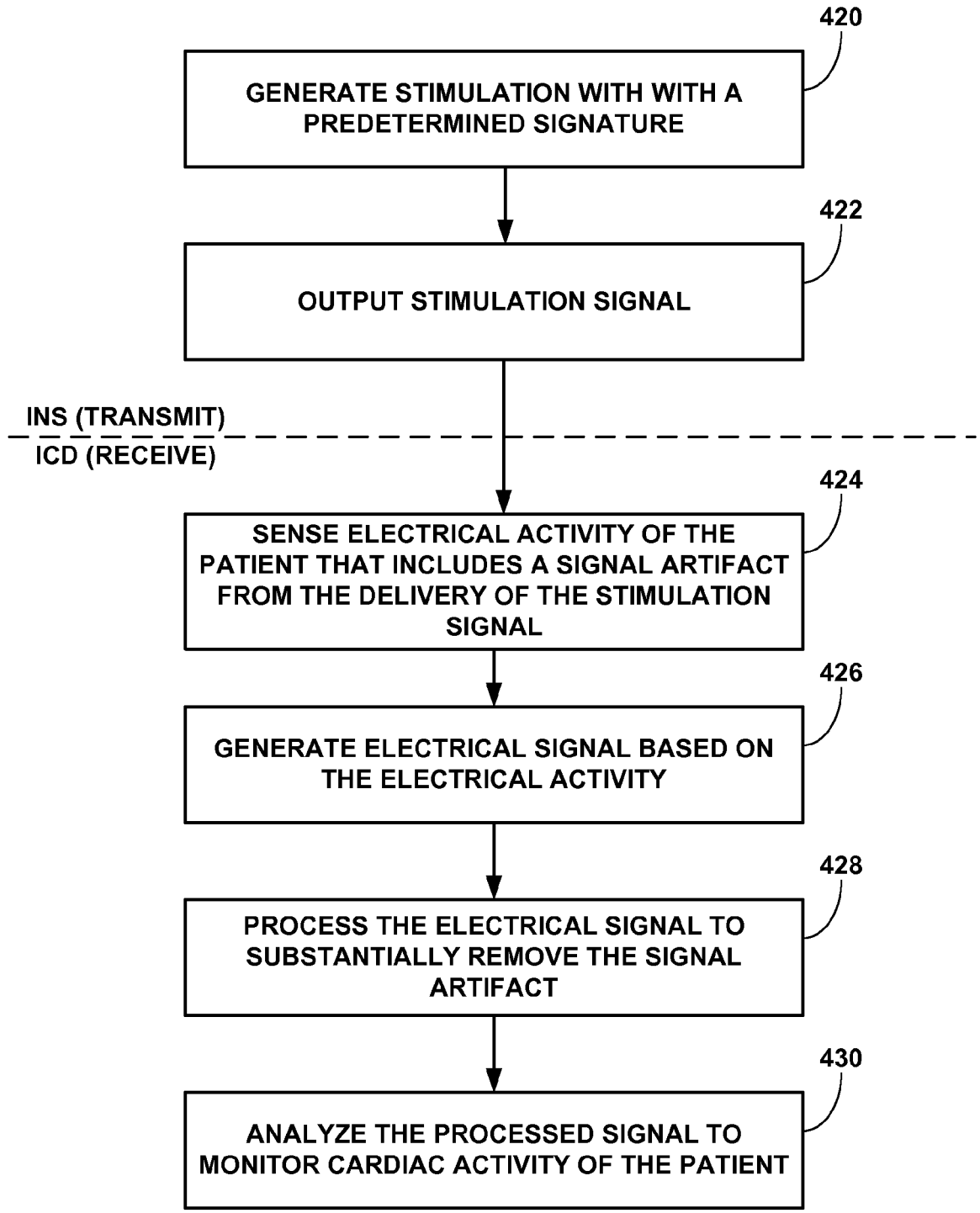
FIGS. 16-18 are flow diagrams illustrating example techniques for reducing the effects of electrical crosstalk on sensing performed by the ICD.

FIG. 16 is a flow diagram of an example technique that may be implemented in order to substantially remove at least some of the stimulation artifact present in an electrical signal sensed by ICD 16. Stimulation generator 88 of INS 26 may generate a stimulation signal having a predetermined signature (420). The predetermined signature may be uniquely characterized by one or more of the frequency (pulse rate), duty cycle, or signal envelope, as described with respect to FIGS. 12A and 12B and 13A and 13B. Moreover, the predetermined signature may be designed to facilitate removal of the resulting signal artifact at ICD 16, such as the use of different notch filters or bandpass filters specifically designed to remove the signal artifact having the predetermined signature. Example stimulation waveforms having predetermined signatures are illustrated and described in greater detail in FIGS. 12A, 12B, 13A, and 13B.

In some examples, INS 26 may generate the stimulation signal with the predetermined signature by initially loading one or more therapy programs from memory 82 (FIG. 6). Processor 80 may control stimulation generator 88 to vary the initial values for one or more the signal parameters, e.g., amplitude, frequency, pulse width, duty cycle, to generate the stimulation signal with the predetermined signature. The values of one or more stimulation parameters may be varied based on a set of rules stored in memory 82, which may, for example, indicate minimum and maximum values for the stimulation parameter values. Stimulation generator 88 may output (i.e., deliver) the stimulation signal (422) in order to provide therapy to patient 12.

Similar to the method in FIG. 15, sensing module 116 (FIG. 7) of ICD 16 may sense electrical activity of patient 12 that includes the signal artifact of the stimulation signal (424). ICD 16 may generates an electrical (sensed) signal based on the electrical activity (426), e.g., by sensing a voltage difference between two or more of electrodes 50-55, 68, 72, 74, and 76. ICD 16 may, for example, generate the sensed signal as an ECG signal or an EGM signal. In such an example, the ECG or EGM signal includes the signal artifact. Sensing module 116 and/or processor 110 of ICD 16 may process the sensed electrical signal to substantially remove the signal artifact (428).

As an example, ICD 16 may be configured to process the sensed signal using a matched filter, comparators, and other signal process components to identify the signal artifact in the sensed signal, and to filter the signal to substantially remove the signal artifact, as described above with respect to FIGS. 7-9. Finally, ICD 16 may analyze the processed signal, i.e., the sensed signal with the signal artifact substantially removed, to monitor the cardiac activity of patient 12 (430). That is, in some examples ICD 16 may analyze an ECG or EGM signal that has been processed to remove the signal artifact to monitor cardiac activity of patient 12. In this way, ICD 16 may reliably analyze an ECG or EGM signal while INS 26 delivers neurostimulation to patient 12. Processor 110 may detect an arrhythmia based on the processed signal (ECG/EGM signal with signal artifact substantially removed), e.g., based on R-R or P-P intervals of the processed signal or the morphology of the ECG/EGM signal. Consequently, the processed (ECG/EGM) signal may be used to control the delivery of cardiac rhythm management therapy to patient 12 while INS 26 delivers neurostimulation to patient 12.

Figure 17:
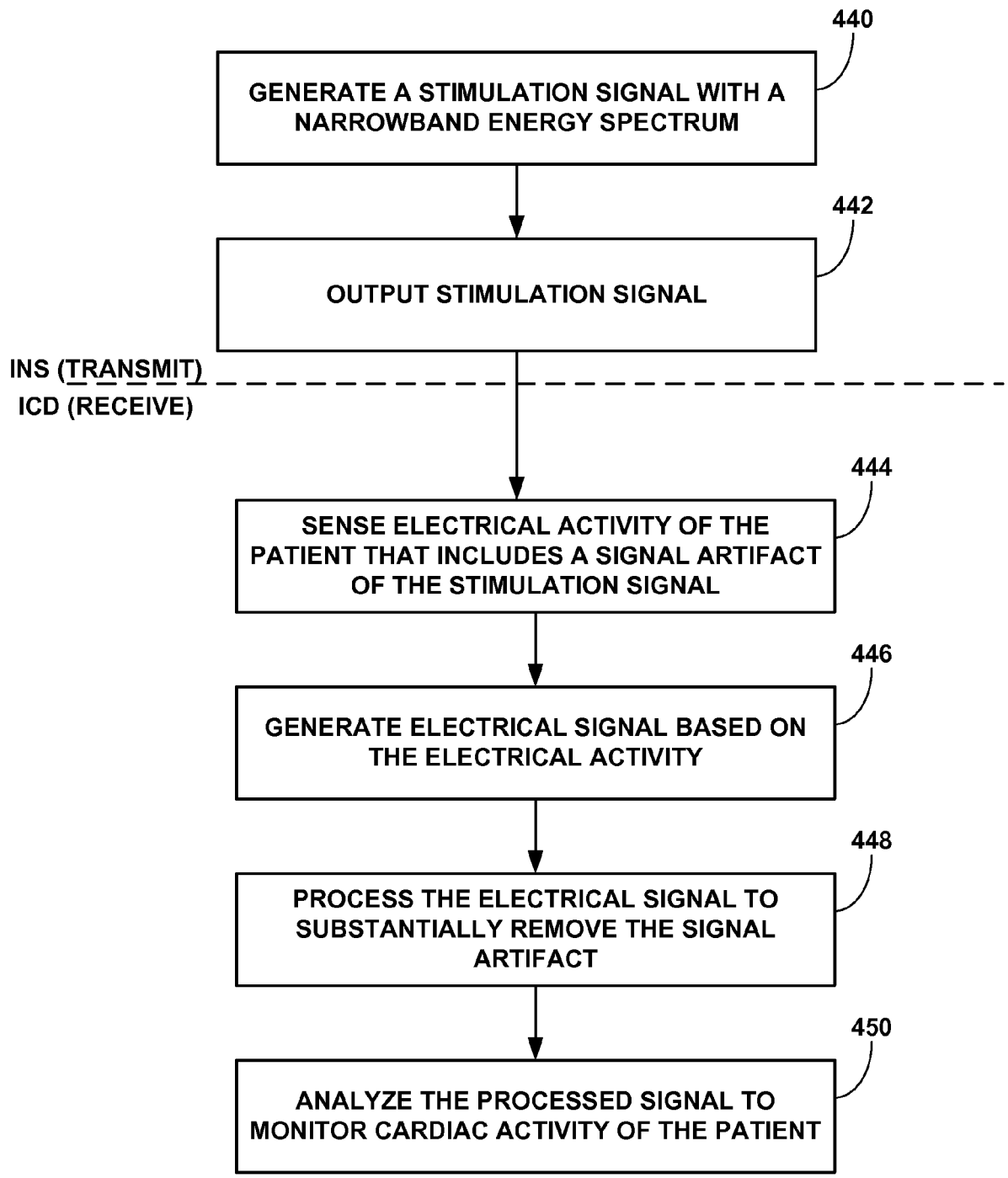

FIG. 17 is a flow diagram of another example technique that may be implemented in order to substantially remove at least some of the stimulation artifact present in an electrical signal sensed by ICD 16. In the method illustrated in FIG. 17, INS 26 generates a stimulation signal with a narrowband energy spectrum (440). In order to generate the stimulation signal with a narrowband energy spectrum, processor 80 (FIG. 6) of INS 26 may load one or more therapy programs from memory 82 (FIG. 6). The therapy programs may define a set of stimulation parameter values for generating the stimulation signal. INS 26 may selectively vary the values of one or more signal parameters from the respective initial value to produce the stimulation signal with the narrowband energy spectrum. For example, INS 26 may change the initial value for one or more of the frequency, pulse width, phase, and duty cycle to produce the stimulation signal with a narrowband energy spectrum.

Generating the stimulation signal with a narrowband energy spectrum may help focus the energy of the stimulation signal at a particular frequency or a particular frequency band. The frequency may be predetermined so that it is known by INS 26 and ICD 16, and selected as a frequency that may not substantially interfere with a cardiac signal. INS 26 outputs the stimulation signal (442) to provide therapy to patient 12.

Sensing module 116 (FIG. 7) of ICD 16 may sense electrical activity of patient 12 that includes the signal artifact from the stimulation signal output by INS 26 (444). ICD 16 then generates an electrical (sensed) signal based on the electrical activity (446), e.g., by sensing a voltage difference between two or more of electrodes 50-55, 68, 72, 74, and 76 (FIG. 4). Processor 110 may process the sensed electrical signal to substantially remove the signal artifact (448). Because the stimulation signal generated and delivered by INS 26 has a narrowband energy spectrum, the energy of the signal artifact is also focused in the same band of the frequency spectrum. Accordingly, ICD 16 may apply a notch filter centered at the predetermined frequency to substantially remove the signal artifact from the sensed signal. Processor 110 may analyze the processed signal, i.e., the sensed signal with the signal artifact substantially removed, to monitor the cardiac activity of patient 12 (450), e.g., to control the delivery of cardiac rhythm management therapy to patient 12.

Figure 18:
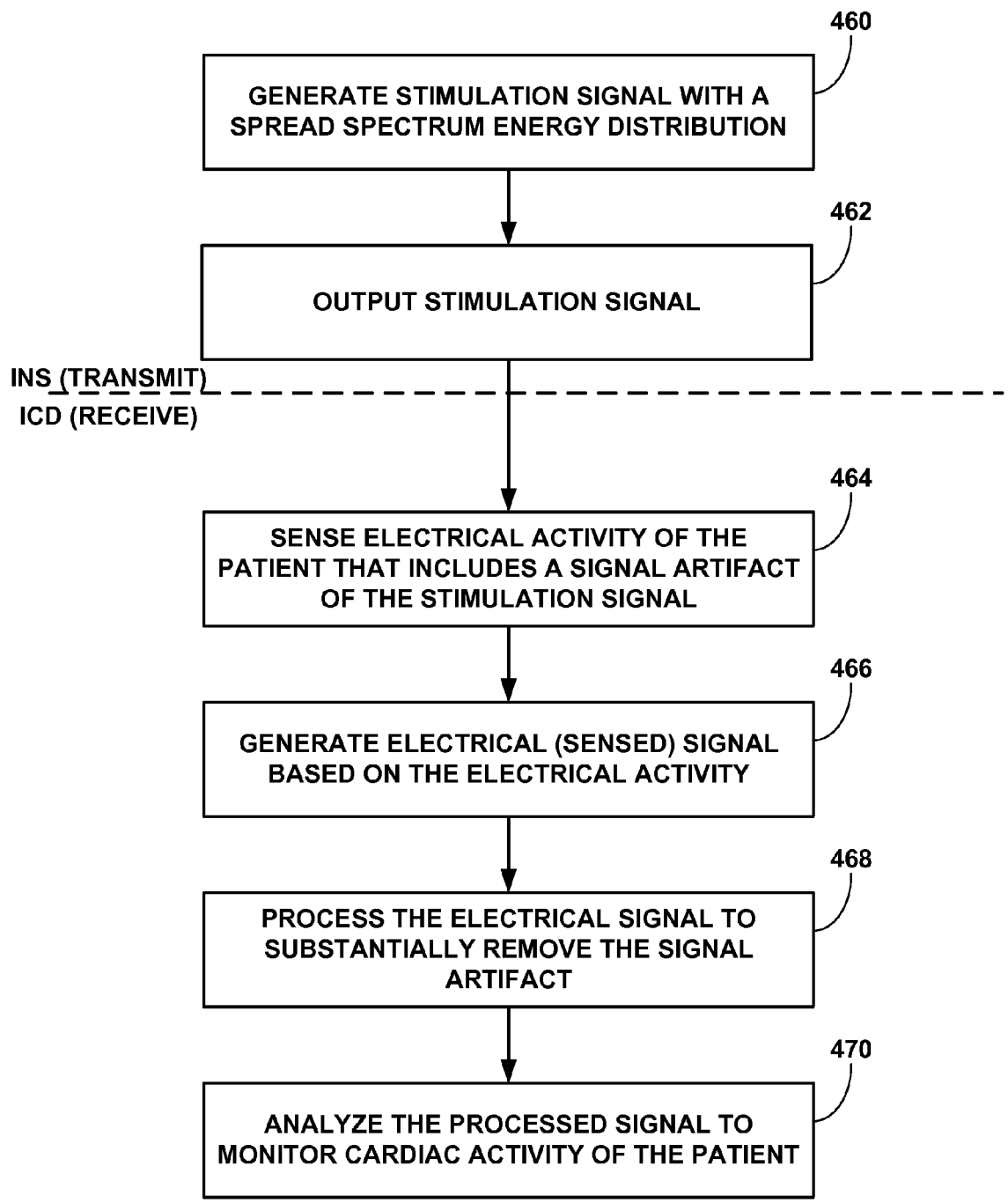

FIG. 18 is a flow diagram of an example technique that may be implemented in order to reduce the impact of crosstalk between INS 26 and ICD 16 on the sensing of cardiac signals by ICD 16. Stimulation generator 88 (FIG. 7) of INS 26 may generate a stimulation signal having a spread spectrum energy distribution (460). In order to generate the stimulation signal with a spread spectrum energy distribution, processor 80 (FIG. 6) of INS 26 may load one or more therapy programs from memory 82 (FIG. 6). INS 26 may then randomly or pseudo-randomly vary the values of one or more signal parameters defined by the therapy programs. The signal parameters may include, for example, one or more of frequency, pulse width, phase, and duty cycle. By randomly or pseudo-randomly varying one or more of the signal parameters, the energy of the stimulation signal may be spread over a wide frequency spectrum. Because the energy of the stimulation signal is spread substantially over a wide frequency spectrum, the resulting signal artifact may not substantially interfere with the cardiac signal sensed by ICD 16 and, more particular, may not adversely interfere with the cardiac signal at frequencies that contain critical cardiac information for detecting an arrhythmia.

INS 26 outputs the stimulation signal (462) to provide therapy to patient 12. ICD 16 may senses electrical activity of patient 12, and inadvertently sense an artifact of the stimulation signal output by INS 26 (464). ICD 16 may generate an electrical signal based on the electrical activity (466), e.g., by sensing a voltage difference between two or more of electrodes 50-55, 68, 72, 74, and 76. The signal artifact may appear as wideband noise in the sensed electrical signal because it has a spread spectrum energy distribution.

In some examples, processor 110 (FIG. 7) of ICD 16 may process the sensed electrical signal to substantially remove the signal artifact (468). For example, processor 110 may filter the sensed electrical signal, e.g., by applying a wideband filter or otherwise process the signal to remove wideband noise. In other examples, however, the signal artifact may not substantially interfere with the cardiac signal because it may appear as a relatively low level wideband noise. Thus, ICD 16 may not apply additional processing to the sensed signal. In either case, processor 110 of ICD 16 may analyze the sensed signal, which may or may not be processed to remove wideband noise, to monitor the cardiac activity of patient 12 (470).

The techniques described in this disclosure are described with reference to therapy systems 10, 11, 500 (FIGS. 1-3) including physically separate devices 16, 26. In some examples, the techniques described herein may also be applicable to a single medical device including an electrical stimulation module that generates and delivers electrical stimulation to one or more tissue sites, e.g., proximate a nerve and/or an extravascular tissue site (which may or may not be proximate a nerve), and a cardiac therapy module that senses electrical cardiac activity of patient 12 and delivers cardiac rhythm management therapy to heart 14 of patient 12.

Figure 19:
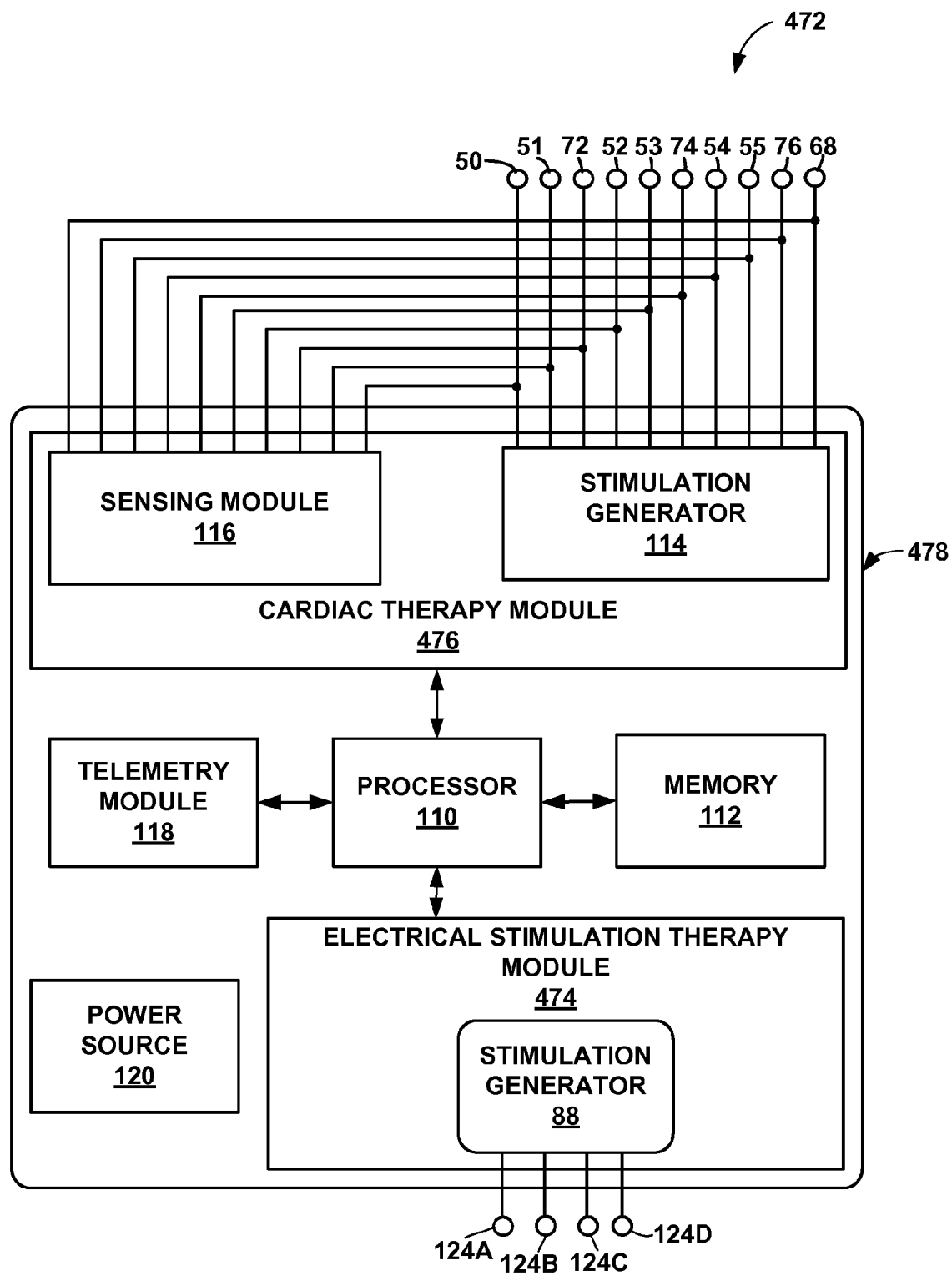
FIG. 19 is a functional block diagram of an implantable medical device that includes an electrical stimulation module that generates and delivers electrical stimulation to a tissue site within a patient and a cardiac therapy module that generates and delivers cardiac rhythm management therapy to a heart of the patient.

FIG. 19 is a functional block diagram illustrating an example IMD 472 that includes an electrical stimulation module 474 and a cardiac therapy module 476 in a common housing 478. Electrical stimulation therapy module 474 includes stimulation generator 88, which is described above with respect to FIG. 6. Similarly, cardiac therapy module 476 includes stimulation generator 114 and sensing module 116, which are described above with respect to FIG. 7. IMD 472 also includes processor 110, memory 112, telemetry module 118, and power source 120, which are described above with respect to FIG. 7.

Electrical stimulation therapy module 474 may deliver electrical stimulation to a nonmyocardial tissue site or a nonvascular cardiac tissue site. As previously discussed with respect to INS 26, the stimulation may be delivered to the nerve via an intravascular lead or an extravascular lead. In other examples, electrical stimulation therapy module 474 may deliver electrical stimulation to an extravascular tissue site that may or may not be proximate a nerve. Cardiac therapy module 476 may sense electrical cardiac signals of patient 12 and deliver cardiac rhythm management therapy to heart 14, such as pacing, cardioversion or defibrillation therapy.

Processor 110 may control electrical stimulation therapy module 474 and cardiac therapy module 476 according to any of the techniques described above to minimize the possibility that cardiac therapy module 476 delivers electrical stimulation to heart 14 in response to detecting electrical signals generated and delivered by electrical stimulation therapy module 474 that resemble an arrhythmic cardiac signal. For example, processor 110 may implement any of the techniques described with respect to FIGS. 16-18 in order to control stimulation generator 88 of electrical stimulation therapy module 474 to generate an electrical stimulation signal that is either easily filtered by sensing module 116 or processor 110, or that has a spread spectrum energy distribution that minimizes the interference with sensing of true cardiac signals by sensing module 116.

For example, with respect to the technique shown in FIG. 16, processor 110 may control electrical stimulation therapy module 474 to generate and deliver a stimulation signal having a predetermined signature to patient 12 (420, 422). As discussed above, the predetermined signature may be designed to facilitate removal of the resulting signal artifact by sensing module 116 or processor 110.

Sensing module 116 of IMD 472 may sense electrical activity of patient 12 that includes the signal artifact of the stimulation signal and generate an electrical signal based on the electrical activity (424, 426). Sensing module 116 and/or processor 110 of IMD 472 may process the sensed electrical signal to substantially remove the signal artifact (428). Processor 110 may analyze the processed signal, i.e., the sensed signal with the signal artifact substantially removed, to monitor the cardiac activity of patient 12 (430).

The techniques described in this disclosure, including those attributed to ICD 16, INS 26, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following example statements.

The invention claimed is:

1. A method comprising:
    generating an electrical stimulation signal that has a predetermined signature with a first therapy module that delivers electrical stimulation therapy to a patient, wherein the predetermined signature is characterized by at least one of a varying duty cycle or a signal envelope of the electrical stimulation signal;
    delivering the electrical stimulation signal to tissue of the patient via a first set of electrodes connected to the first therapy module;
    sensing electrical activity within the patient with a second set of electrodes electrically connected to a second therapy module, wherein the electrical activity includes a physiological signal of the patient and a signal artifact from the delivery of the electrical stimulation signal by the first therapy module;
    generating a sensed electrical signal based on the sensed electrical activity; and
    processing the sensed electrical signal to remove at least part of the signal artifact based on the predetermined signature.

2. The method of claim 1, wherein the first and second therapy modules are enclosed within a common housing of an implantable medical device.

3. The method of claim 1, wherein the first and second therapy modules are enclosed within respective housings of physically separate implantable medical devices.

4. The method of claim 1, wherein the physiological signal comprises an electrical cardiac signal.

5. The method of claim 1, wherein generating the electrical stimulation signal that has the predetermined signature comprises generating the electrical stimulation signal comprising a repeating predetermined signature.

6. The method of claim 1, wherein the predetermined signature is characterized by a signal parameter that progressively increases in value from a minimum value to a maximum value, and subsequently progressively decreases in value to the minimum value, the signal parameter comprising at least one of the duty cycle, a slew rate, a frequency, a pulse rate, a pulse width or amplitude.

7. The method of claim 1, wherein the predetermined signature is characterized by a signal parameter that progressively decreases in value from a maximum value to a minimum value, and subsequently progressively increases in value to the maximum value, the signal parameter comprising at least one of the duty cycle, a slew rate, a frequency, a pulse rate, a pulse width or amplitude.

8. The method of claim 1, wherein the predetermined signature is characterized by a signal parameter that progressively increases in value from a minimum value to a maximum value, the signal parameter comprising at least one of the duty cycle, a slew rate, a frequency, a pulse rate, a pulse width or amplitude.

9. The method of claim 1, wherein the predetermined signature is characterized by a signal parameter that progressively decreases in value from a maximum value to a minimum value, the signal parameter comprising at least one of the duty cycle, a slew rate, a frequency, a pulse rate, a pulse width or amplitude.

10. The method of claim 1, wherein processing the sensed electrical signal to remove at least part of the signal artifact comprises applying at least one of a notch filter or a bandpass filter to the sensed electrical signal.

11. A method comprising:
sensing electrical activity within a patient with a second therapy module, wherein the electrical activity includes a physiological signal of the patient and a signal artifact from a delivery of an electrical stimulation signal to the patient by an implantable medical device, the electrical stimulation signal comprising a predetermined signature that is characterized by at least one of a varying duty cycle or a signal envelope of the electrical stimulation signal;
generating a sensed electrical signal based on the sensed electrical activity; and
processing the sensed electrical signal to remove at least part of the signal artifact based on the predetermined signature of the electrical stimulation signal.

12. The method of claim 11, wherein processing the sensed electrical signal comprises applying at least one of a notch filter or a bandpass filter to the sensed electrical signal.

13. The method of claim 11, wherein the physiological signal comprises an electrical cardiac signal.

14. A system comprising:
a first set of electrodes;
a second set of electrodes;
a first therapy module that generates and delivers an electrical stimulation signal having a predetermined signature to tissue of a patient via the first set of electrodes, wherein the predetermined signature is characterized by at least one of a varying duty cycle or a signal envelope of the electrical stimulation signal;
a second therapy module that senses electrical activity within the patient via the second set of electrodes, wherein the electrical activity includes a physiological signal and a signal artifact from the delivery of the electrical stimulation signal by the first therapy module, wherein the second therapy module generates a sensed electrical signal based on the electrical activity; and
a processor that processes the sensed electrical signal to remove at least part of the signal artifact based on the predetermined signature.

15. The system of claim 14, further comprising an implantable medical device comprising a housing, wherein the first and second therapy modules are enclosed within the housing.

16. The system of claim 14, further comprising a first implantable medical device and a second implantable medical device physically separate from the first implantable medical device, wherein the first implantable medical device comprises the first therapy module and the second implantable medical device comprises the second therapy module and the processor.

17. The system of claim 14, wherein the physiological signal comprises an electrical cardiac signal.

18. The system of claim 14, wherein the predetermined signature is characterized by a signal parameter that progressively increases in value from a minimum value to a maximum value, and subsequently progressively decreases in value to the minimum value, the signal parameter comprising at least one of the duty cycle, a slew rate, a frequency, a pulse rate, a pulse width or amplitude.

19. The system of claim 14, wherein the predetermined signature is characterized by a signal parameter that progressively decreases in value from a maximum value to a minimum value, and subsequently progressively increases in value to the maximum value, the signal parameter comprising at least one of the duty cycle, a slew rate, a frequency, a pulse rate, a pulse width or amplitude.

20. The system of claim 14, wherein the predetermined signature is characterized by a signal parameter that progressively increases in value from a minimum value to a maximum value, the signal parameter comprising at least one of the duty cycle, a slew rate, a frequency, a pulse rate, a pulse width or amplitude.

21. The system of claim 14, wherein the predetermined signature is characterized by a signal parameter that progressively decreases in value from a maximum value to a minimum value, the signal parameter comprising at least one of the duty cycle, a slew rate, a frequency, a pulse rate, a pulse width or amplitude.

22. The system of claim 14, wherein the processor processes the sensed electrical signal to remove at least part of the signal artifact based on the predetermined signature by applying at least one of a notch filter or a bandpass filter to the sensed electrical signal.

23. A system comprising:
means for generating an electrical stimulation signal that has a predetermined signature, wherein the predetermined signature is characterized by at least one of a varying duty cycle or a signal envelope of the electrical stimulation signal;
means for delivering the electrical stimulation signal to tissue of the patient via a first set of electrodes electrically connected to the first therapy module;
means for sensing electrical activity within the patient with a second set of electrodes electrically connected to a second therapy module, wherein the electrical activity includes a physiological signal of the patient and a signal artifact from the delivery of the electrical stimulation signal by the first therapy module;
means for generating a sensed electrical signal based on the sensed electrical activity; and
means for processing the sensed electrical signal to remove at least part of the signal artifact based on the predetermined signature.

24. The system of claim 23, wherein the means for processing the sensed electrical signal to remove at least part of the signal artifact based on the predetermined signature comprises means for applying at least one of a notch filter or a bandpass filter to the sensed electrical signal.

* * * * *